US012661502B2

(12) United States Patent
Sano et al.

(10) Patent No.: US 12,661,502 B2
(45) Date of Patent: Jun. 23, 2026

(54) METHODS AND APPARATUS FOR MODIFYING OR KILLING CELLS BY MANIPULATING THE CELL MEMBRANE CHARGING TIME

(71) Applicant: North Carolina State University, Raleigh, NC (US)

(72) Inventors: Michael Benjamin Sano, Cary, NC (US); Christopher Fesmire, Cary, NC (US); Ross A. Petrella, Richmond, VA (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 1242 days.

(21) Appl. No.: 17/536,355

(22) Filed: Nov. 29, 2021

(65) Prior Publication Data

US 2022/0080192 A1    Mar. 17, 2022

Related U.S. Application Data

(63) Continuation-in-part of application No. PCT/US2020/035146, filed on May 29, 2020, and a (Continued)

(51) Int. Cl.
*A61N 1/30* (2006.01)
*A61N 1/32* (2006.01)
(Continued)

(52) U.S. Cl.
CPC ............. *A61N 1/306* (2013.01); *A61N 1/325* (2013.01); *C12M 35/04* (2013.01); *C12N 15/87* (2013.01)

(58) Field of Classification Search
None
See application file for complete search history.

(56) References Cited

U.S. PATENT DOCUMENTS 5,385,544 A    1/1995  Edwards et al.
6,022,316 A *  2/2000  Eppstein .............. A61N 1/0416
                                              604/290

(Continued)

FOREIGN PATENT DOCUMENTS

CN        87100574 A     8/1987
CN        105283143 A    1/2016

(Continued)

OTHER PUBLICATIONS

"Cell membrane", Wikipedia, retrieved from https://en.wikipedia.org/w/index.php?title=Cell_membrane&oldid=899062612 (6 pages) (May 27, 2019).

(Continued)

*Primary Examiner* — Mallika D Fairchild
(74) *Attorney, Agent, or Firm* — Myers Bigel, P.A.

(57)    ABSTRACT

A method of treatment includes modifying and/or killing cells by changing the cell membrane charging time to make the cells more susceptible to the influence of electric fields. The method may further include inserting one or more electrodes into tissue, acquiring a temperature of the tissue, delivering electrical energy to the tissue by electrical pulses, determining a rate of energy delivery of the electrical energy such that the temperature rises above a first critical temperature but remains below a second critical temperature, and delivering the electrical energy until a specific dose is achieved.

20 Claims, 37 Drawing Sheets

Related U.S. Application Data continuation-in-part of application No. PCT/US2020/035168, filed on May 29, 2020.

(60) Provisional application No. 62/855,509, filed on May 31, 2019, provisional application No. 62/855,480, filed on May 31, 2019.

(51) Int. Cl.
  *C12M 1/42* (2006.01)
  *C12N 15/87* (2006.01)

(56) References Cited

U.S. PATENT DOCUMENTS

| | | | |
|---|---|---|---|
| 2003/0225331 | A1 | 12/2003 | Diederich et al. |
| 2005/0096584 | A1 | 5/2005 | Ferek-Petric |
| 2012/0215213 | A1 | 8/2012 | Juzkiw et al. |
| 2012/0215218 | A1 | 8/2012 | Lipani |
| 2013/0253415 | A1* | 9/2013 | Sano ...................... A61B 18/14 606/41 |
| 2014/0025064 | A1 | 1/2014 | Collins et al. |
| 2015/0150618 | A1 | 6/2015 | Onik et al. |
| 2016/0166310 | A1 | 6/2016 | Stewart et al. |
| 2016/0166312 | A1 | 6/2016 | Johnston |
| 2016/0184003 | A1 | 6/2016 | Srimathveeravalli et al. |
| 2016/0324575 | A1 | 11/2016 | Panescu et al. |
| 2016/0331441 | A1 | 11/2016 | Konings |
| 2016/0367310 | A1 | 12/2016 | Onik et al. |
| 2017/0035499 | A1 | 2/2017 | Stewart et al. |
| 2017/0065343 | A1 | 3/2017 | Mickelsen |
| 2017/0245928 | A1 | 8/2017 | Xiao et al. |
| 2017/0266438 | A1* | 9/2017 | Sano ........................ A61N 1/40 |
| 2017/0348525 | A1 | 12/2017 | Sano et al. |
| 2017/0348539 | A1 | 12/2017 | Schwarz et al. |
| 2018/0071014 | A1 | 3/2018 | Neal et al. |
| 2018/0263685 | A1 | 9/2018 | Onik et al. |
| 2018/0303543 | A1* | 10/2018 | Stewart .............. A61B 18/1492 |
| 2021/0212753 | A1 | 7/2021 | Sano et al. |

FOREIGN PATENT DOCUMENTS

| | | |
|---|---|---|
| CN | 105792883 A | 7/2016 |
| WO | 2007014003 A2 | 2/2007 |
| WO | 2018005511 A1 | 1/2018 |
| WO | 2019232358 A1 | 12/2019 |

OTHER PUBLICATIONS

Al-Sakere et al. "Tumor ablation with irreversible electroporation" PloS One 2(11):e1135-e1135 (Nov. 2007).

Arena et al. "High-frequency irreversible electroporation (H-FIRE) for non-thermal ablation without muscle contraction" Biomed. Eng. Online 10:102-102 (2011).

Dong et al. "First Human Trial of High-Frequency Irreversible Electroporation Therapy for Prostate Cancer" Technol. Cancer Res. Treat. 17:1533033818789692-1533033818789692 (Jul. 2018).

El-Shabouri "Positively charged nanoparticles for improving the oral bioavailability of cyclosporin-A" Int. J. Pharm. 249(1):101-108 (Dec. 2002).

Hickey et al. "Control of polymeric nanoparticle size to improve therapeutic delivery" J. Control. Release Off. J. Control. Release Soc. 219:536-547 (Dec. 2015).

Kamaly et al. "Degradable Controlled-Release Polymers and Polymeric Nanoparticles: Mechanisms of Controlling Drug Release" Chem. Rev. 116(4):2602-2663 (Feb. 2016).

Notification of Transmittal of the International Search Report and the Written Opinion of the International Searching Authority, or the Declaration, in corresponding PCT Application No. PCT/US2020/035146 (11 pages) (Oct. 16, 2020).

Notification of Transmittal of the International Search Report and the Written Opinion of the International Searching Authority, or the Declaration, in corresponding PCT Application No. PCT/US2020/035168 (22 pages) (Oct. 8, 2020).

O'Brien et al. "Effects of internal electrode cooling on irreversible electroporation using a perfused organ model" Int. J. Hyperthermia 35:44-55 (2019).

Rogers et al. "Strength-duration curve for an electrically excitable tissue extended down to near 1 nanosecond" IEEE Transactions on Plasma Science 32(4):1587-1599 (2004).

Sano et al. "Burst and continuous high frequency irreversible electroporation protocols evaluated in a 3D tumor model" Phys. Med. Biol. 63(13):35022 (2018).

Sano et al. "Bursts of Bipolar Microsecond Pulses Inhibit Tumor Growth" Sci. Rep. 5:14999 (Oct. 2015).

Sano et al. "In-vitro bipolar nano- and microsecond electro-pulse bursts for irreversible electroporation therapies" Bioelectrochemistry 100:69-79 (2014).

Sano et al. "Production of Spherical Ablations Using Nonthermal Irreversible Electroporation: A Laboratory Investigation Using a Single Electrode and Grounding Pad" Spec. Issue Interv. Oncol. 27(9):1432-1440.e3 (Sep. 2016).

Sano et al. "Reduction of Muscle Contractions during Irreversible Electroporation Therapy Using High Frequency Bursts of Alternating Polarity Pulses: A Laboratory Investigation in an Ex Vivo Swine Model" J Vasc Interv Radiol. 29(6):893-898.e4 (2018).

Smith et al. "Active mechanisms are needed to describe cell responses to submicrosecond, megavolt-per-meter pulses: cell models for ultrashort pulses" Biophysical Journal 95:1547-1563 (2008).

Weaver et al. "A brief overview of electroporation pulse strength-duration space: a region where additional Intracellular effects are expected" Bioelectrochemistry 87:236-243 (2012).

Xia et al. "Salt-Induced Charge Screening and Significant Conductivity Enhancement of Conducting Poly(3,4-ethylenedioxythiophene):Poly(styrenesulfonate)" Macromolecules 42(12):4141-4147 (Jun. 2009).

Extended European Search Report Corresponding to European Application No. 20812651.6 (13 pages) (Jun. 1, 2023).

Fesmire et al. "Irreversible electroporation is a thermally mediated ablation modality for pulses on the order of one microsecond" Bioelectrochemistry (May 5, 2020).

Pucihar et al. "Equivalent Pulse Parameters for Electroporation" IEEE Transactions on Biomedical Engineering 58 (11) (Nov. 2011).

Retelj et al. "Electroporation of Intracellular Liposomes Using Nanosecond Electric Pulses—A Theoretical S" IEEE Transactions on Biomedical Engineering 60(9) (Sep. 2013).

"Chinese Office Action in Corresponding Application No. 2019800362501, mailed Mar. 30, 2024, 7 pages".

* cited by examiner

FIG. 1C

Cytoplasm Permittivity[0.01 – 10,000]

Time [s]

TMP [V]

Modified Charging Time By Modifying Electrical Properties of Cell & Tissue

FIG. 5B          FIG. 5C

METHODS AND APPARATUS FOR MODIFYING OR KILLING CELLS BY MANIPULATING THE CELL MEMBRANE CHARGING TIME

RELATED APPLICATIONS

This application is a continuation-in-part and claims priority to PCT Application No. PCT/US2020/035168, filed May 29, 2020, and PCT Application No. PCT/US2020/035146, filed May 29, 2020, both of which claim priority to U.S. Provisional Application No. 62/855,509, filed May 31, 2019, and U.S. Provisional Application No. 62/855,480, filed May 31, 2019, the entire contents of which are hereby incorporated by reference.

BACKGROUND

The present invention relates pulsed electric field therapies.

The ablation of unwanted soft tissue can be achieved by many means, including surgical excision, application of excessive amount of ionizing radiation or other forms of energy (excessive heating and cooling), exposure to cytotoxic chemicals, or by a combination of these means. It is common to use these means to destroy neoplasms. Treatments known in the art involve surgical intervention to physically remove the aberrant cell mass, radiation to kill the cells of the aberrant cell mass, exposure of aberrant cells to toxic chemicals (i.e., chemotherapy), or a combination of such techniques. While each treatment modality has shown significant effectiveness in treatment of various cell proliferative diseases, no one technique has been shown to be highly effective at treating all types of cell proliferative diseases and disorders.

While surgical intervention is effective at removal of solid tumors on tissues and organs that are physically accessible and capable of sustaining physical damage or capable of regeneration, surgical intervention can be difficult to perform on tumors that are not readily accessible or on organs that do not regenerate. In these cases, surgical intervention can often involve substantial physical damage to the patient, requiring extensive recuperation times and follow-on treatments. At other times, the extensive growth of the neoplasm prevents removal, since attempts at removal would likely kill the patient. Likewise, treatment with radiation can result in collateral damage to tissue surrounding the tumor, and can cause long-lasting side-effects, which can lower the quality of life of the patient. Chemotherapeutic treatments can cause systemic damage to the patient and can result in significant side effects that might require a long recuperation period or cause permanent damage to tissues and organs.

Recent work by the inventors has focused on the ablation of unwanted soft tissue (malignant tumors) by application of excessive electrical energy, which may involve placing electrodes within or near the targeted region to deliver a series of low energy, microsecond electric pulses. These pulses permanently destabilize the cell membranes of the targeted tissue (e.g., tumor), thereby killing the cells. Pulsed electric field therapies may also include treatments such as electro-chemotherapy and electro-gene therapy which aim to enhance the transport of extrinsic molecules into cells by administering a series of electrical pulses which make the cell membrane more permeable to these molecules.

The application of long duration electrical pulses to cells in vitro is commonly used to enhance the permeability of the cell membrane to large membrane-impermeable molecules through a process known as electroporation. In this process, cells must be exposed to an electric field sufficient to increase the transmembrane potential above a critical threshold for a duration substantially longer than the native charging time of the cell membrane. Electroporation is discussed, for example, in Weaver, J. C., Smith, K. C., Esser, A. T., Son, R. S. & Gowrishankar, T. R., "A brief overview of electroporation pulse strength-duration space: a region where additional intracellular effects are expected," *Bioelectrochemistry* 87, 236-243, doi:10.1016/j.bioelechem.2012.02.007 (2012). These pulses typically have durations between 100 μs and is with magnitudes on the order of 100 to 1000 V/cm. A high degree of experimental validation may be required for nearly every individual cell type to identify the combination of pulse duration, pulse number, pulse repetition rate, and pulse magnitude that results in optimal permeabilization of the cell membrane without disrupting viability.

Unfortunately, in the vast majority of cases, only a very small proportion of cells exposed to the electric fields survive. Additionally, not all surviving cells successfully absorb the target material. In the case of genetic engineering only a proportion will integrate the desired material correctly into their genome. The low survival rates and intense induced muscle contractions associated with these electrical pulses precludes their use in most in vivo electro-chemotherapy and electro-gene therapy applications. Shorter electrical pulses, with durations on the order of, or shorter than, the native cell membrane charging time may be associated with improved cell survival (see, e.g., Sano, M. B., Arena, C. B., DeWitt, M. R., Saur, D. & Davalos, R. V., "In-vitro bipolar nano- and microsecond electro-pulse bursts for irreversible electroporation therapies," *Bioelectrochemistry* 100, 69-79, doi:10.1016/j.bioelechem.2014.07.010 (2014)) and less intense muscle contractions (see, e.g., Sano, M. B. et al., "Reduction of Muscle Contractions during Irreversible Electroporation Therapy Using High Frequency Bursts of Alternating Polarity Pulses: A Laboratory Investigation in an Ex Vivo Swine Model," (2018) *Journal of Vascular and Interventional Radiology,* 29 (6), pp. 893-898.e4 (2018) and Rogers, W. R. et al., "Strength-duration curve for an electrically excitable tissue extended down to near 1 nanosecond," *IEEE Transactions on Plasma Science,* 32(4), 1587-1599 (2004)), but also lower degrees of permeabilization to large molecules (see, e.g., Smith, K. C. et al., "Active mechanisms are needed to describe cell responses to submicrosecond, megavolt-per-meter pulses: cell models for ultrashort pulses," *Biophysical Journal* 95, 1547-1563 (2008)).

As exposure to high intensity pulsed electric fields is associated with a substantial degree of cell death, there is growing interest in the use of these fields for tissue ablation and the non-surgical removal or destruction of tissue to treat a wide variety of disease states including cancer. In these procedures, cells must be exposed to even greater electric fields to ensure that sufficient damage occurs to the cell membrane. Under certain conditions it is not possible to induce either permeabilization or cell death when pulses are shorter than the native charging time of the cell membrane.

SUMMARY

According to some embodiments of the present invention, a method of treatment comprising modifying and/or killing a cell by changing a cell membrane charging time to make the cell more susceptible to an influence of an electric field.

In some embodiments, the cell membrane charging time is changed by modifying electrical properties of an extracellular environment, an intracellular environment, components of the intracellular environment, a cell membrane, or components of the cell membrane.

In some embodiments, the cell membrane charging time is changed by modifying molecular and/or chemical properties of an extracellular environment, an intracellular environment, components of the intracellular environment, a cell membrane, or components of the cell membrane.

In some embodiments, components of the cell membrane includes hydrophilic head groups, hydrophobic tail groups, carbohydrates, cholesterols, receptors, protein channels, surface proteins, globular proteins, transmembrane proteins, integral proteins, lipid anchored proteins, peripheral proteins, voltage gated proteins, ion channels, proton pumps, guanine nucleotide-binding protein-coupled receptors, hydrophilic pores, hydrophobic pores, phospholipid molecules, a cytoskeleton, enzymes, hormones, focal adhesion groups, cell junctions, integrins, cadherins, cilia, filopoidia, and/or microvilli.

In some embodiments, components of the extracellular environment include blood, blood plasma, extracellular fluid, cerebrospinal fluid, extracellular matrix, interstitial matrix, basement membrane, connective tissue, bone, tendon, ligament, proteins, collagen, elastin, fibronectin, laminin, enzymes, glycoproteins, fibrous proteins, and/or polysaccharides.

In some embodiments, components of the intracellular environment include the cytoskeleton, organelles, a nucleus, a cytoplasm, proteins, DNA, and RNA.

In some embodiments, electric, magnetic, electromagnetic, thermal, radiation, ultrasound, and/or optical energy is used to modify the cell membrane charging time.

In some embodiments, chemicals or molecules are used to modify the cell membrane charging time including molecules for fatty acid supplementation (e.g., oleic acid, myristoleic acid, sapienic acid, vaccenic acid, linoleic acid, linolenic acid, alpha linolenic acid, linoelacidic acid, palmitic acid, palmitoleic acid, lauric acid, arachidonic acid, arachidic acid, stearic acid, myristic acid, elaidic acid, erucic acid, eicosapentaenoic acid, docosahexaenoic acid, hexanoic acid, acrylic acid, caprylic acid, capric acid, behenic acid, lignoceric acid, cerotic acid, cholesterol, cholesterol esterase, cholesterol transferase, cholesterol oxidase, cholesteryl ester transfer protein, sterol, beta-sitosterol, sigmasterol, lanosterol, coprostanol, or lecithin), cholesterol or fatty acid synthesis and transport affecters (e.g., decarestrictine D, U1866A, sulfosuccinimidyl oleate sodium, sulfosuccinimidyl myristate), phospholipids (e.g., phosphatitic acid, phosphatidylethanolamine, phosphatidylcholine, phosphatidylserine, phosphatidylinositol, phosphatidylinositol phosphate, phosphatidylinositol biphosphate, phosphatidylinositol trisphosphate, sphingomyelin, cardiolipin, filipin), cholesterol effecting drugs (e.g., probucol, gemfibrozil, fenofibrate, nicotinic acid, hyodeoxycholic acid, GW 590735, cyclandelate), cyclodextrins (e.g., beta cyclodextrin, beta cyclodextrin hydrate, hydroxypropyl beta cyclodextrin, methyl beta cyclodextrin, 2-hydroxypropyl beta cyclodextrin, heptakis(2,6-di-O-methyl) beta cyclodextrin, triacetyl beta cyclodextrin, succinyl-(2-hydroxypropyl) beta cyclodextrin, acetyl beta cyclodextrin, succinyl beta cyclodextrin, betadex), and/or other lipophilic or amphiphilic small molecules (e.g., curcumin, perllic acid, melatonin, ibuprofen, acetaminophen, acetylsalicylic acid) that affect the cell membrane charging time.

In some embodiments, changing the cell membrane charging time of the cell membrane comprises changing an electric field distribution in an extracellular environment, an intracellular environment, and/or a cell membrane.

In some embodiments, changing the cell membrane charging time of the cell membrane comprises changing a response of a transmembrane potential due to an external stimulus (e.g., electric pulse, chemical gradient).

In some embodiments, an application of the electric field results in immediate or delayed cell death.

In some embodiments, the cell membrane charging time is changed by adding extrinsic molecules to an extracellular environment, a cell membrane, and/or an intracellular environment.

In some embodiments, modifying the cell comprises modifying a genome and/or a gene expression of the cell.

In some embodiments, modifying the cell comprises making it easier for drugs, nucleic acids, and/or molecules to cross the cell membrane.

In some embodiments, modifying the cell comprises making the cell a target of an immune system of a host of the cell.

In some embodiments, modifying the cell comprises stimulating a local and/or systemic immune response.

In some embodiments, modifying the cell comprises altering a structure and/or function of a cytoskeleton, a nucleus, a mitochondria, an endoplasmic reticulum, and/or other organelles.

In some embodiments, killing the cell comprises rupturing a cell membrane and/or causing immediate cell death.

In some embodiments, killing the cell comprises inducing apoptosis and/or delayed cell death.

In some embodiments, killing the cell comprises making the cell a target for immune cells.

In some embodiments, a tissue under treatment is heated to modify the cell membrane charging time then pulsed electric fields are delivered to induce immediate or delayed cell death.

In some embodiments, control algorithms are used to maintain a temperature above a first critical threshold.

In some embodiments, control algorithms are used to maintain a temperature below a second critical threshold.

In some embodiments, the method further includes inserting one or more electrodes into tissue; acquiring a temperature of the tissue; delivering electrical energy to the tissue by electrical pulses; determining a rate of energy delivery of the electrical energy such that the temperature rises above a first critical temperature and remains below a second critical temperature; and delivering the electrical energy until a specific dose is achieved.

In some embodiments, the electrical energy is delivered between a single electrode and a grounding pad.

In some embodiments, the electrical energy is delivered between multiple electrodes and a grounding pad.

In some embodiments, the electrical energy is delivered between two or more electrodes sequentially or simultaneously.

In some embodiments, the electrical energy is delivered by electrodes that are internally cooled.

In some embodiments, the electrical energy is delivered by electrodes that are internally heated.

In some embodiments, the electrical pulses are between 1 ns and 1000 μs in duration, optionally between 100 ns and 10 μs.

In some embodiments, the electrical pulses are between 1V and 100,000V in amplitude, optionally between 250V and 10,000V.

In some embodiments, the electrical pulses comprise positive polarity pulses and/or negative polarity pulses.

In some embodiments, the electrical pulses alternate between positive and negative polarity.

In some embodiments, a positive polarity electrical pulse is delivered, followed by a first delay, then a negative polarity pulse is delivered followed by a second delay.

In some embodiments, the first delay is equal to the second delay and is between 10 ns and 100 ms in duration, optionally between 100 ns and 100 μs.

In some embodiments, the first delay is shorter than the second delay, and wherein the first delay is between 10 ns and 100 μs and the second delay is between 10 μs and 10 s.

In some embodiments, the first delay is constant, and wherein the second delay is changed based on an algorithm.

In some embodiments, the temperature is measured internally to the one or more electrodes.

In some embodiments, the temperature is measured at one or more locations along a surface of the one or more electrodes.

In some embodiments, the temperature is measured at a location within the tissue under treatment.

In some embodiments, the temperature is measured at a tumor margin and/or adjacent to structures such as nerves, vasculature, vessels, and/or healthy tissue.

In some embodiments, the temperature is a plurality of temperatures acquired at multiple locations.

In some embodiments, the first critical temperature is between 36° C. and 65° C., optionally between 37° C. and 55° C.

In some embodiments, the second critical temperature is between 37° C. and 120° C., optionally between 45° C. and 95° C.

In some embodiments, the rate of energy delivery is controlled by adjusting a duty cycle of the electrical pulses.

In some embodiments, the rate of energy delivery is controlled by adjusting a width of the electrical pulses.

In some embodiments, the rate of energy delivery is controlled by adjusting a delay between electrical pulses between 0.1 Hz and 10,000 Hz, optionally between 1 Hz and 1000 Hz.

In some embodiments, the rate of energy delivery is controlled by adjusting an amount of time that the electrical energy is delivered per second between 1 ns/s and 1 s/s, optionally between 1 μs/s and 500 μs/s.

In some embodiments, the specific dose is calculated as a total number of electrical pulses delivered, and the specific dose is between 1 and 100,000,000 pulses, optionally between 100 and 100,000.

In some embodiments, the specific dose is calculated as a number of electrical pulses times a duration of each electrical pulse, and the duration of each electrical pulse is between 1 μs and 10 s and the specific dose is between 0.000001 s and 10 s.

In some embodiments, a pulse width, pulse amplitude, or rate of energy delivery is changed based on a clinical observation or measurement.

In some embodiments, a pulse duration is increased or decreased in response to muscle contractions or patient discomfort.

In some embodiments, an energy delivery rate is increased or decreased in response to muscle contractions or patient discomfort.

In some embodiments, the specific dose is modified based on changes to the pulse width, rate or energy delivery, or pulse amplitude.

In some embodiments, the specific dose is increased when a pulse width is decreased or a pulse amplitude is decreased.

In some embodiments, the specific dose is decreased when a pulse width is increased or a pulse amplitude is increased.

According to some embodiments of the present invention, an apparatus for preventing, mitigating, and/or reducing tissue damage during a pulsed electric field therapy comprising a plurality of electrical pulses, the apparatus comprising circuitry configured to modify and/or kill a cell by changing a cell membrane charging time to make the cell more susceptible to an influence of an electric field.

In some embodiments, the cell membrane charging time is changed by modifying electrical properties of an extracellular environment, an intracellular environment, components of the intracellular environment, a cell membrane, or components of the cell membrane.

In some embodiments, the cell membrane charging time is changed by modifying molecular and/or chemical properties of an extracellular environment, an intracellular environment, components of the intracellular environment, a cell membrane, or components of the cell membrane.

In some embodiments, the apparatus is further configured to use control algorithms that maintain a temperature above a first critical threshold.

In some embodiments, the apparatus is further configured to use control algorithms that maintain a temperature below a second critical threshold.

In some embodiments, the apparatus is further configured to acquire a temperature of tissue under treatment, deliver electrical energy to the tissue by electrical pulses, determine a rate of energy delivery of the electrical energy such that the temperature rises above a first critical temperature and remains below a second critical temperature, and deliver the electrical energy until a specific dose is achieved.

In some embodiments, the electrical energy is delivered by electrodes that are internally heated.

In some embodiments, the electrical pulses are between 1 ns and 1000 μs in duration, optionally between 100 ns and 10 μs.

In some embodiments, the electrical pulses are between 1V and 100,000V in amplitude, optionally between 250V and 10,000V.

In some embodiments, the electrical pulses comprise positive polarity pulses and/or negative polarity pulses.

In some embodiments, electric, magnetic, electromagnetic, thermal, radiation, ultrasound, and/or optical energy is used to modify the cell membrane charging time.

In some embodiments, changing the cell membrane charging time of the cell membrane comprises changing an electric field distribution in an extracellular environment, an intracellular environment, and/or a cell membrane.

In some embodiments, changing the cell membrane charging time of the cell membrane comprises changing a response of a transmembrane potential due to an external stimulus (e.g., electric pulse, chemical gradient).

In some embodiments, the cell membrane charging time is changed by adding extrinsic molecules to an extracellular environment, a cell membrane, and/or an intracellular environment.

In some embodiments, modifying the cell comprises making the cell a target of an immune system of a host of the cell.

In some embodiments, modifying the cell comprises stimulating a local and/or systemic immune response.

In some embodiments, modifying the cell comprises modifying a genome and/or a gene expression of the cell.

According to some embodiments of the present invention, a computer program product for preventing, mitigating, and/or reducing tissue damage during a pulsed electric field therapy comprising a plurality of electrical pulses, the computer program product comprising: a tangible non-transitory computer readable storage medium comprising computer readable program code embodied in the computer readable storage medium that when executed by at least one processor causes the at least one processor to perform operations comprising modifying and/or killing a cell by changing a cell membrane charging time to make the cell more susceptible to an influence of an electric field In some embodiments, the operations further comprise acquiring a temperature of tissue under treatment; delivering electrical energy to the tissue by electrical pulses; determining a rate of energy delivery of the electrical energy such that the temperature rises above a first critical temperature and remains below a second critical temperature; and delivering the electrical energy until a specific dose is achieved In some embodiments, the cell membrane charging time is changed by modifying electrical properties of an extracellular environment, an intracellular environment, components of the intracellular environment, a cell membrane, or components of the cell membrane In some embodiments, the cell membrane charging time is changed by modifying molecular and/or chemical properties of an extracellular environment, an intracellular environment, components of the intracellular environment, a cell membrane, or components of the cell membrane.

BRIEF DESCRIPTION OF THE DRAWINGS

Other features of embodiments of the present disclosure will be more readily understood from the following detailed description of specific embodiments thereof when read in conjunction with the accompanying drawings, in which:

FIGS. 1A-1D illustrate modeled responses of a single cell in response to a pulsed electric field, according to embodiments of the present invention;

FIGS. 5B and 5C illustrate custom ring and pin electrodes that were used for the in vitro experiments, according to embodiments of the present invention;

DETAILED DESCRIPTION

Various embodiments will be described more fully hereinafter with reference to the accompanying drawings. Other embodiments may take many different forms and should not be construed as limited to the embodiments set forth herein. Like numbers refer to like elements throughout.

The present invention relates to systems and methods for altering the native cell membrane charging time. In some embodiments, altering the native cell membrane charging time may make the cell more susceptible to electroporation techniques including tissue ablation and/or permeabilization of the cell membrane. This application is related to U.S. Provisional Application Ser. No. 62/678,554, entitled "ELECTRO-THERMAL THERAPY FOR THE TREATMENT OF DISEASED OR UNWANTED TISSUE," filed in the U.S.

Patent and Trademark Office on May 31, 2018, and International Patent Application Serial No. PCT/US2019/034886, entitled "ELECTRO-THERMAL THERAPY FOR THE TREATMENT OF DISEASED OR UNWANTED TISSUE" filed in the U.S. Patent and Trademark Office on May 31, 2019, the contents of all of which are incorporated herein by reference in their entireties.

Numerical Simulation of Cell Membrane Charging Time

Axial symmetric finite element simulations of a single circular cell in a homogeneous medium were created in COMSOL multiphysics by simultaneously calculating the electric field distribution internally and externally to the cell membrane while simulating the membrane as an impedance boundary condition. The time domain response of the cell membrane was calculated in response to a 1 μs positive electrical pulse followed by a 1 μs delay and finally a 1 μs negative polarity electrical pulse.

Figure 1A:
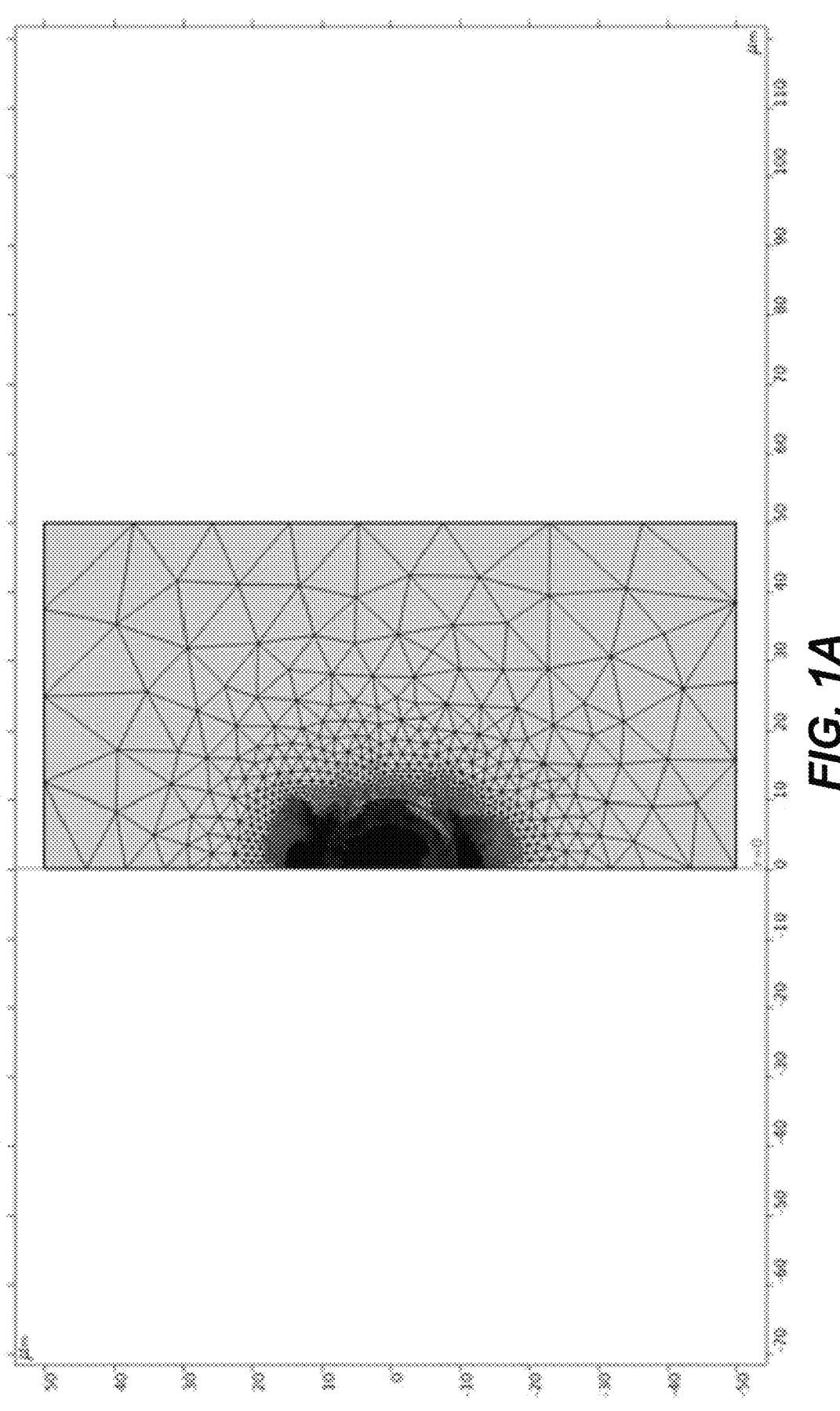
Figure 1B:
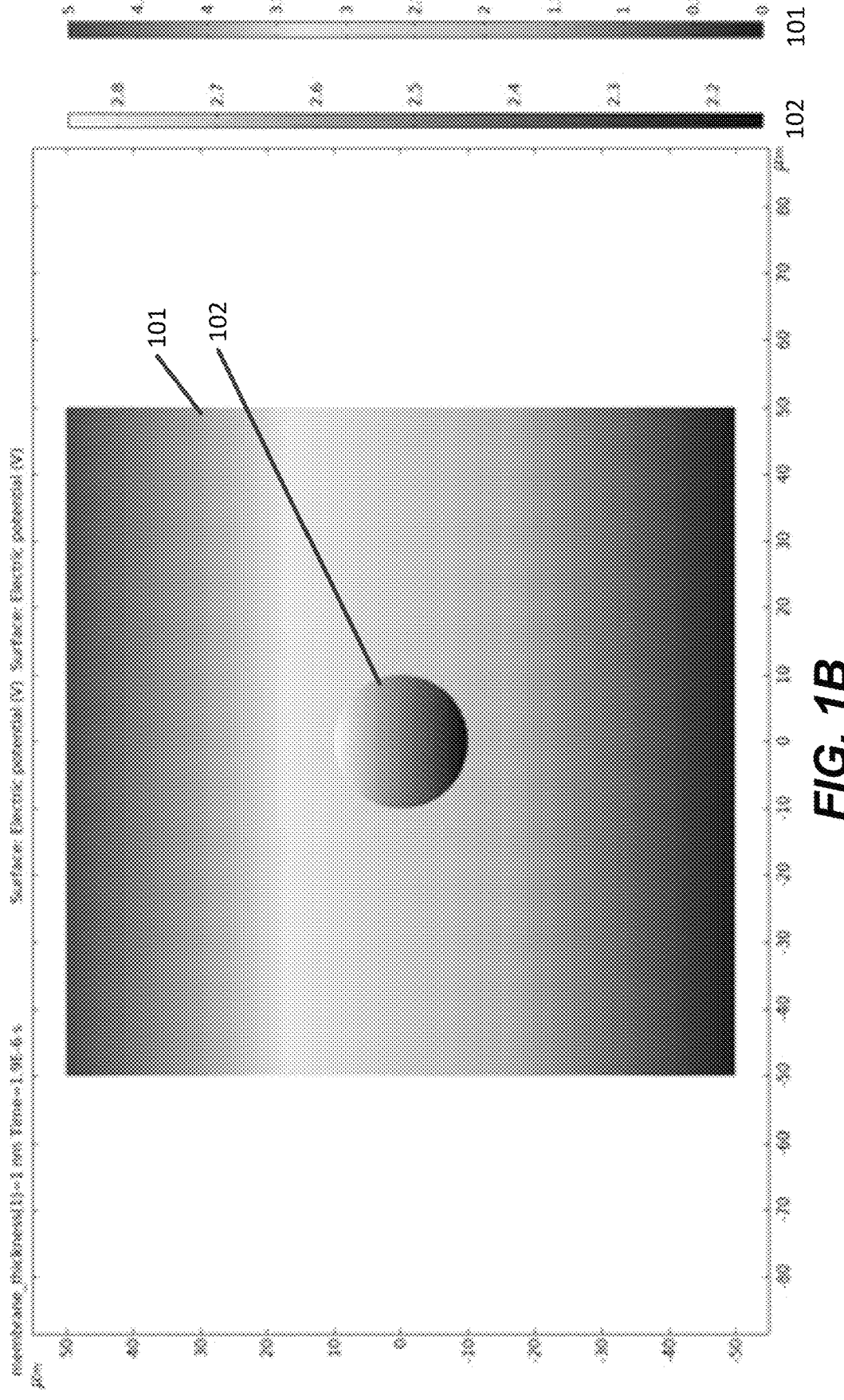
Figure 1C:
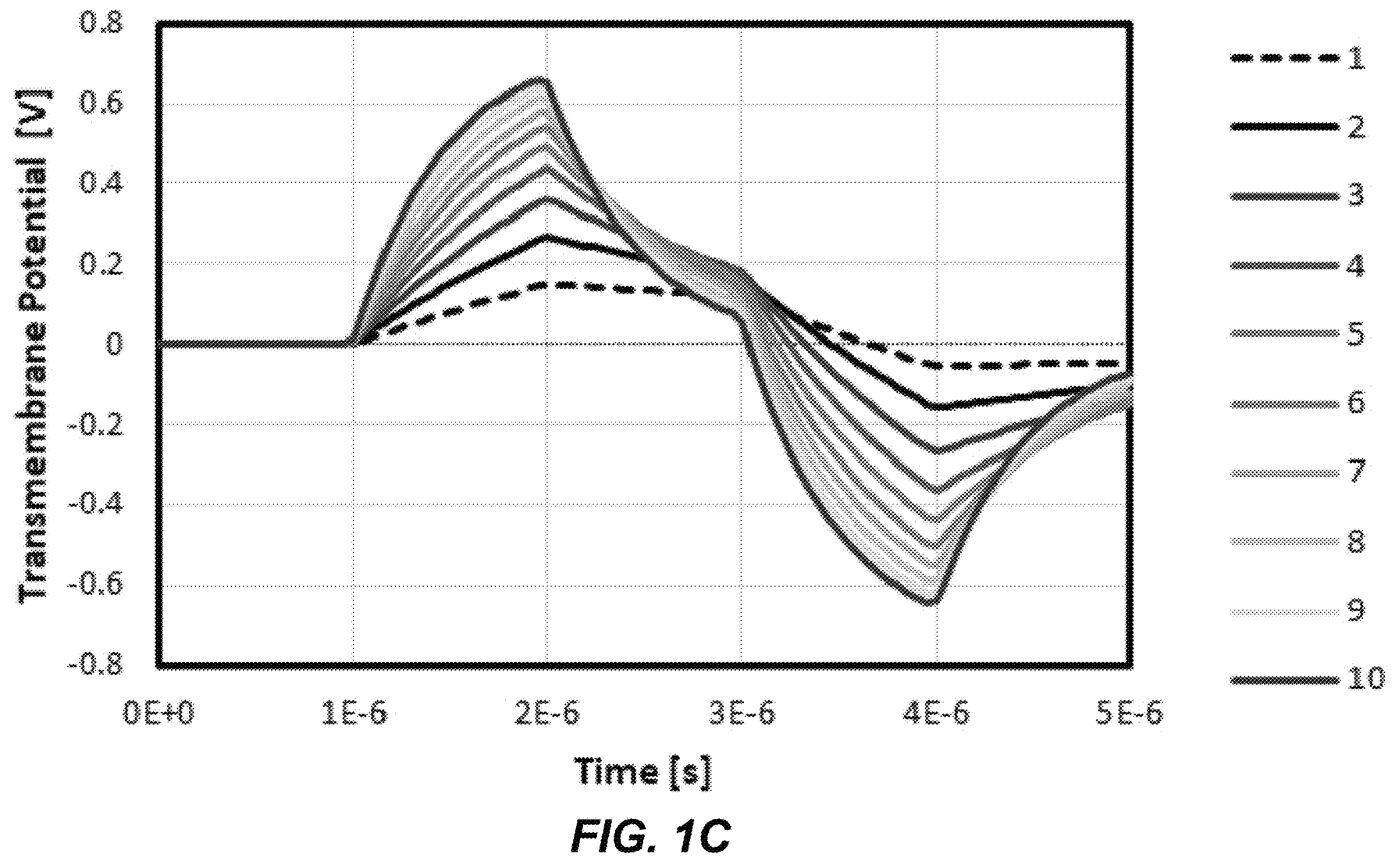
Figure 1D:
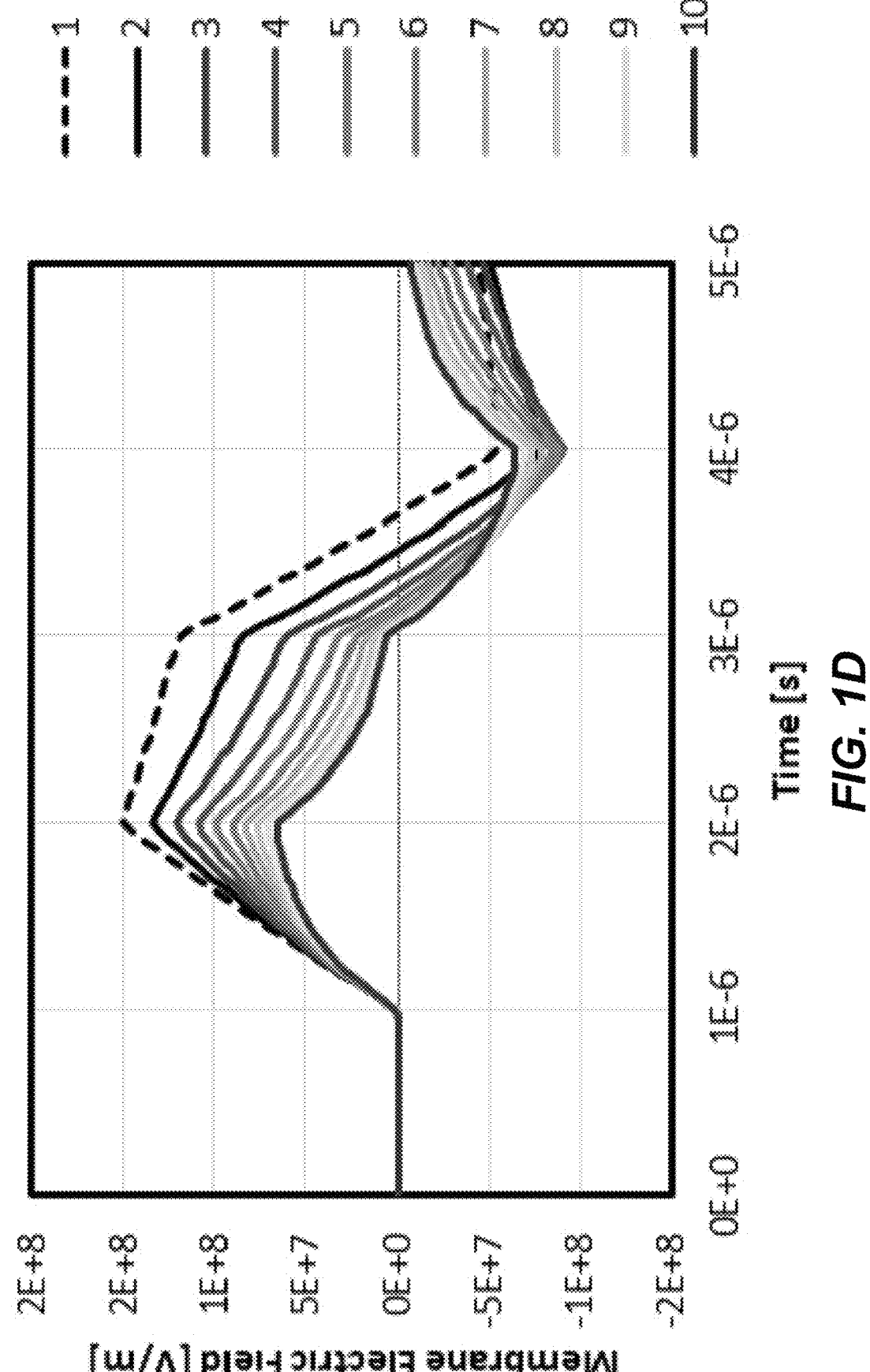

FIGS. 1A-1D illustrate modeled responses of a single cell in response to a pulsed electric field, according to embodiments of the present invention. FIG. 1A illustrates an axial symmetric model of a single cell suspended in a homogeneous medium. This model was used to simulate the application of a pulsed electric field. FIG. 1B illustrates voltage distribution outside 101 and inside 102 the model cell during exposure to a pulsed electric field. FIGS. 1C and 1D illustrate the time dependent transmembrane potential (FIG. 1C) and the time dependent transmembrane electric field (FIG. 1D) as a function of membrane thickness of the model cell (e.g., from 1-10 nm).

The charging time of the cell membrane, determined by the time required for the transmembrane potential to reach a steady state maximum, is dramatically affected by the membrane thickness, with greater membrane thicknesses charging more rapidly. This indicates that techniques which modify this physical property of the cells may have a large impact on the effect of certain pulsed electric fields.

Figure 2A:
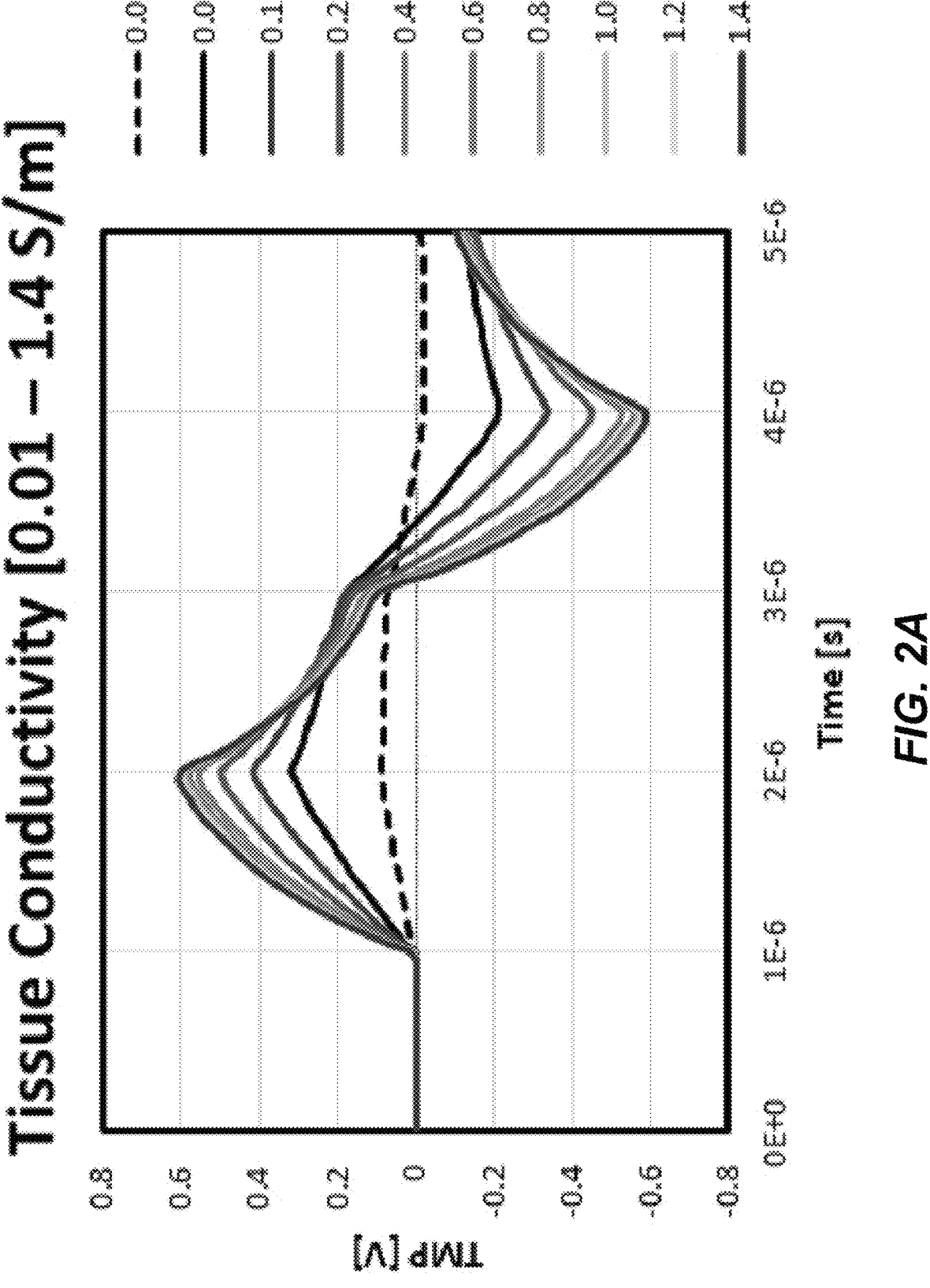
FIGS. 2A and 2B illustrate modeled transmembrane potential of a single cell according to surrounding tissue, according to embodiments of the present invention.
Figure 2B:
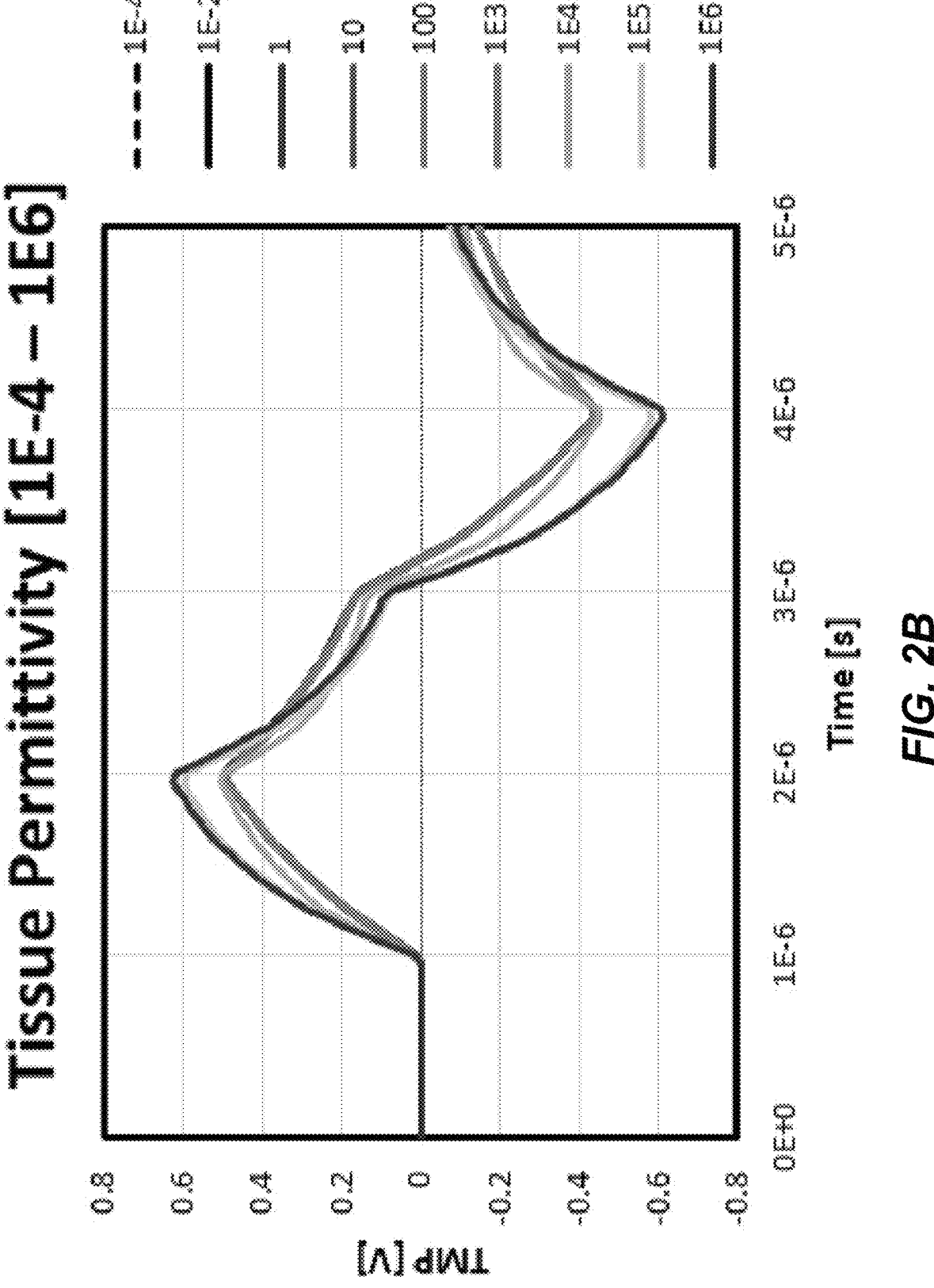

The bulk electrical properties of the tissue surrounding the cells also have an impact on the charging rate of the transmembrane potential. FIGS. 2A and 2B illustrate modeled transmembrane potential of a single cell according to surrounding tissue, according to embodiments of the present invention. FIG. 2A illustrates the time dependent transmembrane potential (TMP) as a function of the surrounding tissue conductivity. FIG. 2B illustrates the time dependent transmembrane potential (TMP) as a function of the surrounding tissue permittivity.

Referring to FIG. 2A, cross physiological ranges (e.g., 0.01-1.41 S/m), higher tissue conductivities result in greater rates of cell membrane charging. In contrast, referring to FIG. 2B, changes in tissue permittivity have a relatively small impact. This indicates that techniques which increase the tissue conductivity such as increasing tissue temperature or the addition of conductive media are preferable for changing the charging time of the cell membrane.

Figure 3A:
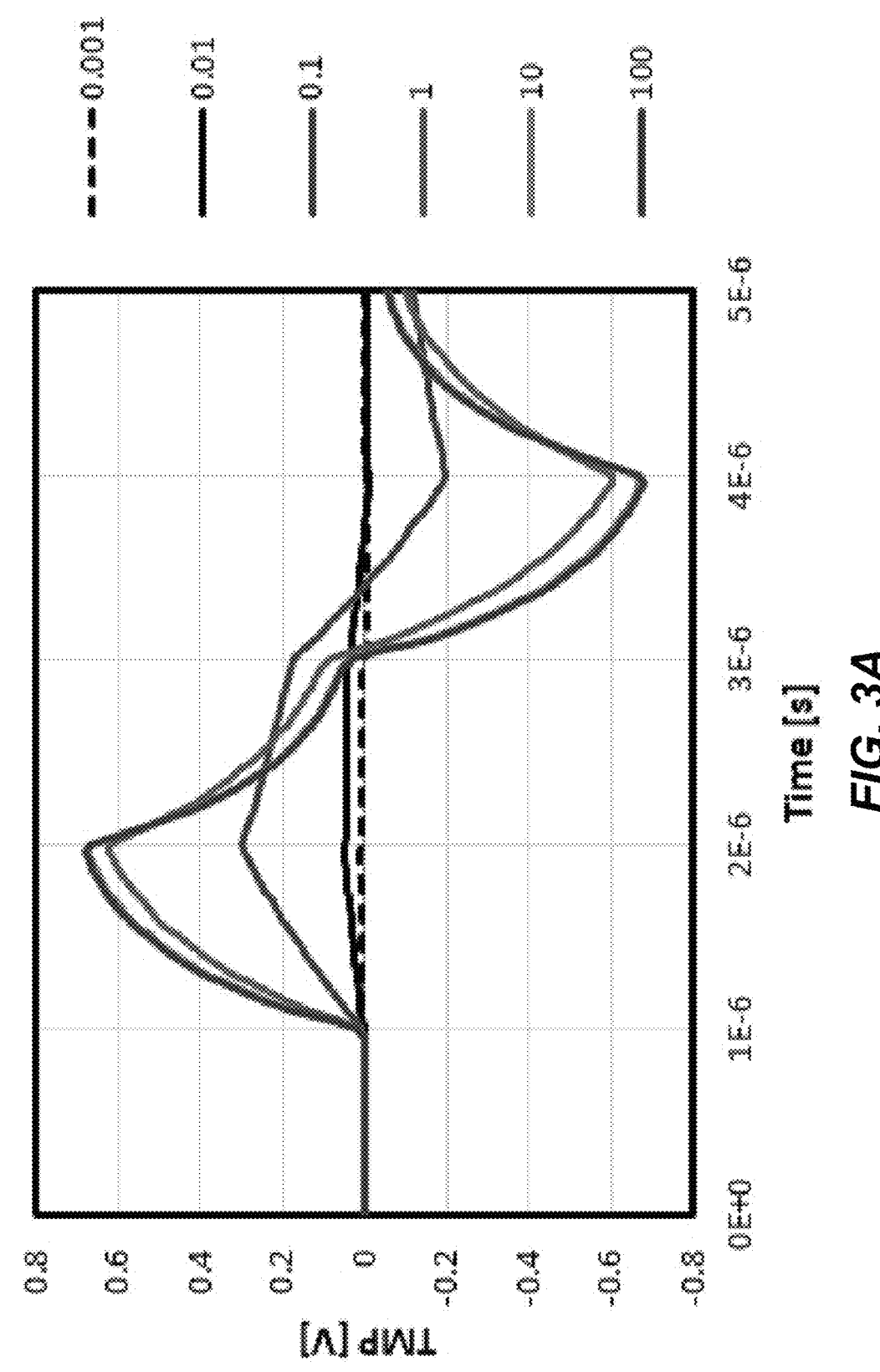
FIGS. 3A, 3B, and 3C illustrate modeled transmembrane potential of a single cell according to the cell cytoplasm, according to embodiments of the present invention.
Figure 3B:
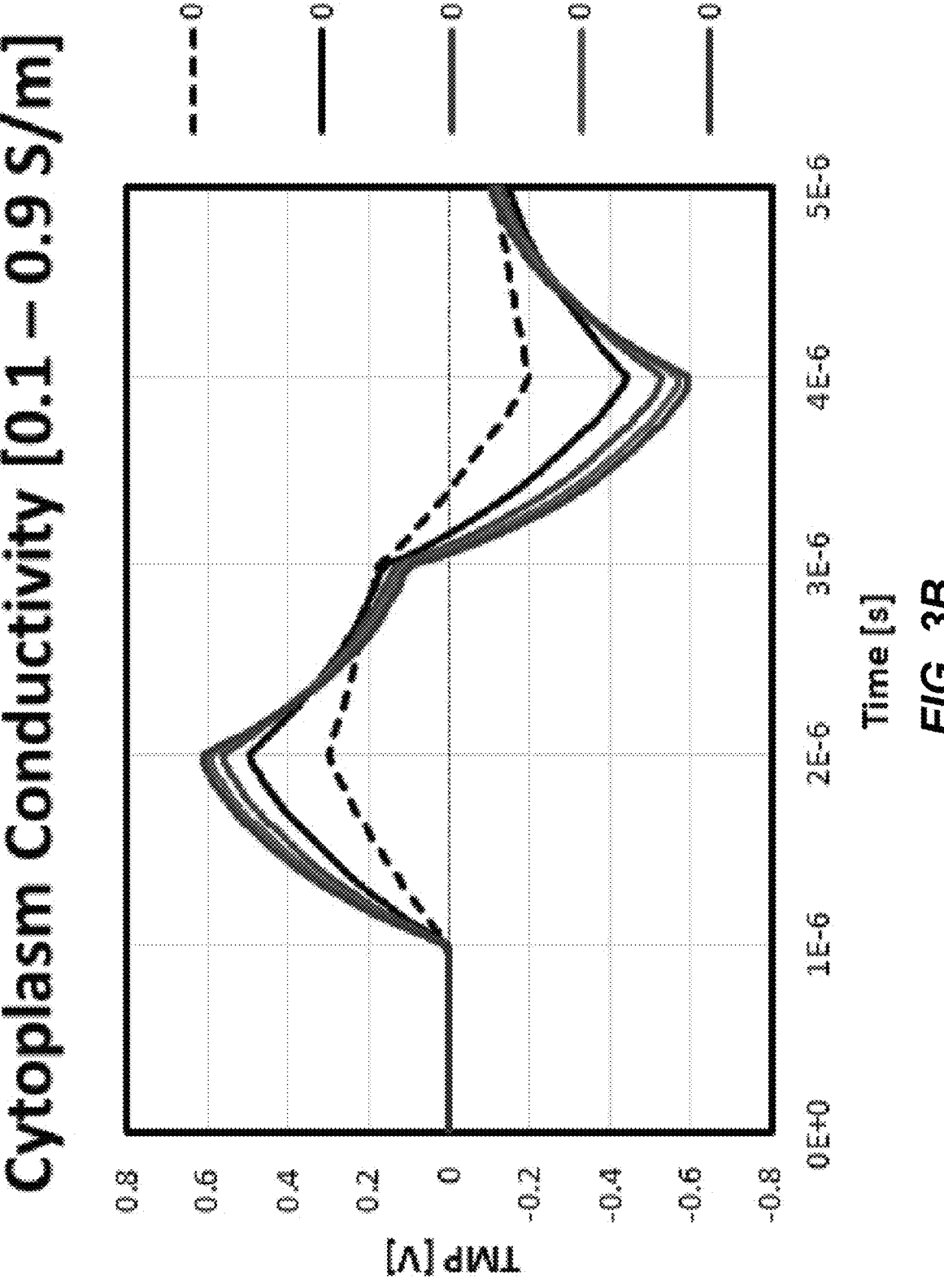
Figure 3C:

Similarly, increasing the cytoplasmic conductivity results in faster rates of cell membrane charging. FIGS. 3A, 3B, and 3C illustrate modeled transmembrane potential of a single cell according to the cell cytoplasm, according to embodiments of the present invention. FIGS. 3A and 3B illustrate the time dependent transmembrane potential (TMP) as a function of the cell cytoplasm conductivity, with FIG. 3A illustrating conductivity ranges from 0.001-100 S/m and FIG. 3B illustrating conductivity ranges from 0.1-0.9 S/m. FIG. 3C illustrates the time dependent transmembrane potential (TMP) as a function of the cell cytoplasm permittivity.

As illustrated in FIGS. 3A-3C, cell membrane charging may be more sensitive to changes in the cell cytoplasm conductivity than the cell cytoplasm permittivity.

Figure 4:
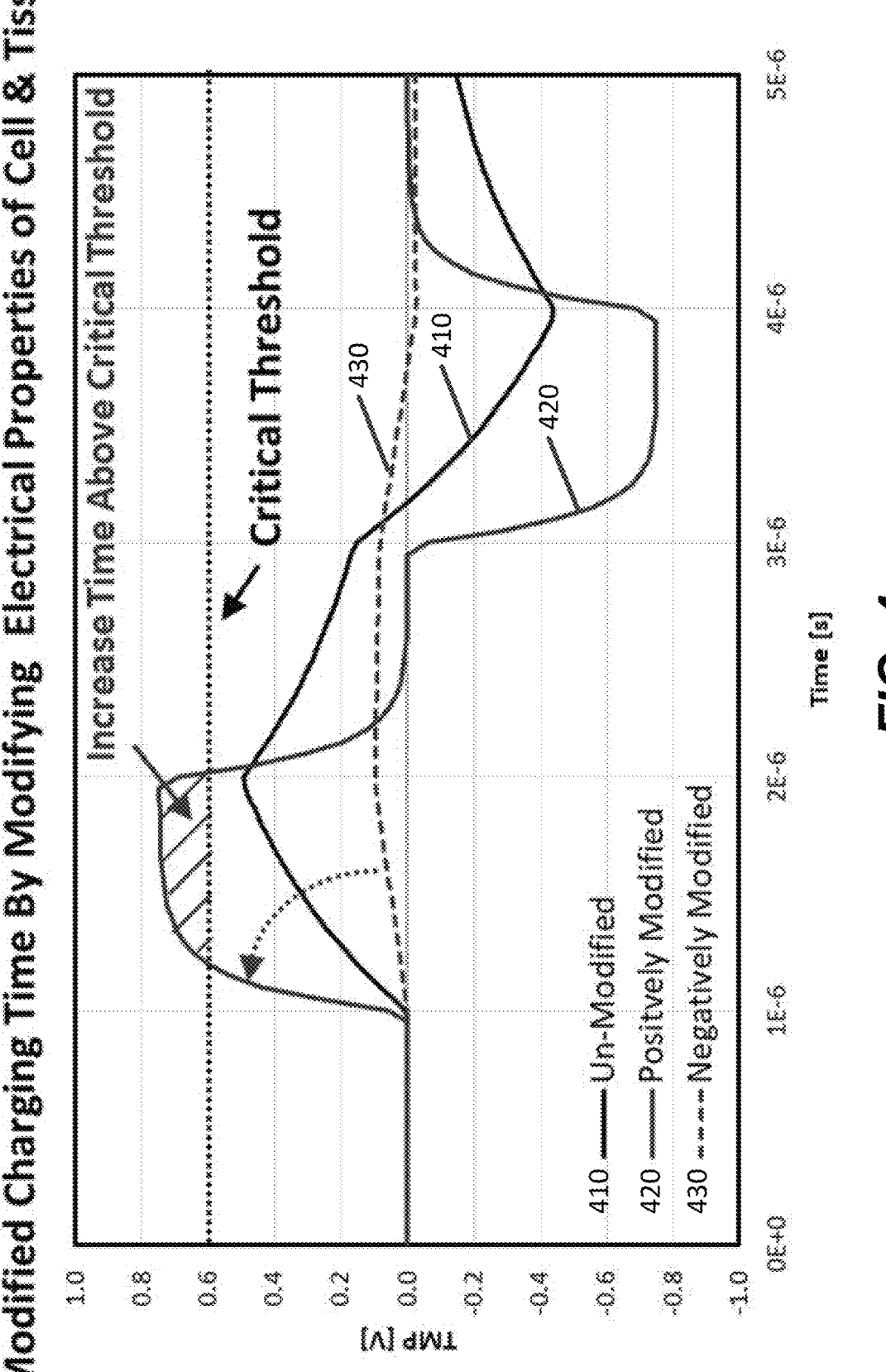
FIG. 4 illustrates simulated results of combinatorial techniques for enhancing or inhibiting cell membrane charging by simultaneously modifying the electrical properties of the tissue, cell membrane, and cytoplasm, according to embodiments of the present invention.

FIG. 4 illustrates simulated results of combinatorial techniques for enhancing or inhibiting cell membrane charging by simultaneously modifying the electrical properties of the tissue, cell membrane, and cytoplasm, according to embodiments of the present invention. In the simulation illustrated in FIG. 4, the electrical properties of the tissue, cell membrane, and cytoplasm were modified as illustrated in Table 1:

TABLE 1

| Case | Membrane Cond. (S/m) | Membrane Perm. | Tissue Cond. (S/m) | Tissue Perm. | Membrane Thickness (m) | Cytoplasm Cond. (S/m) | Cytoplasm Perm. |
|---|---|---|---|---|---|---|---|
| Baseline | 3.00E−07 | 8.57 | 0.2 | 80 | 5.00E−09 | 0.3 | 154.4 |
| Best | 1.50E−07 | 4.285 | 0.4 | 160 | 1.00E−08 | 0.6 | 308.8 |
| Worst | 6.00E−07 | 17.14 | 0.1 | 40 | 2.50E−09 | 0.15 | 77.2 |

Table 1 shows the electrical properties for the tissue, cell membrane, and cytoplasm used to simulate a nominal 'baseline' cell as well as scenarios where cell membrane charging is maximally increased (best case) and maximally decreased (worst case). The results of the simulation are illustrated in FIG. 4, where the "Un-Modified" line 410 illustrates the Baseline of Table 1, the "Positively Modified" line 420 illustrates the Best case of Table 1, and the "Negatively Modified" line 430 illustrates the Worst case of Table 1. As illustrated in FIG. 4, the Best case modification results in a charging time that exceeds a critical threshold for the model cell for a longer duration than either the Baseline or the Worst case.

In Vitro Demonstration of Temperature Effect on Cell Membrane Charging Time

A 3D tumor model was used to investigate the effects of electrical pulse width, temperature, membrane properties, and dose (integrated time) on glioblastoma cells. Briefly, U-118 MG Grade IV human glioblastoma cells (HTB-15, ATCC Inc., Manassas, VA) were cultured in DMEM (11965118, Gibco, Gaithersburg, MD), supplemented with 10% V/V Fetal Bovine Serum (A3160601, Gibco, Gaithersburg, MD) and 2% V/V Penicillin-Streptomycin solution (15070063, Gibco, Gaithersburg, MD) until reaching approximately 80% confluence. The cells were then harvested via trypsinization (25200056, Gibco, Gaithersburg, MD), centrifuged, and suspended in fresh media at a concentration of $1\times10^6$ cells/mL. Three dimensional (3D) tumor constructs were created by mixing the concentrated cell suspension with PureCol EZ gel (5074-35ML, Advanced Biomatrix, San Diego, CA) in a 1 to 1 ratio to achieve a 2.5 mg/mL concentration of type 1 collagen and $5\times10^5$ cells/mL with a volume fraction of approximately $4\times10^{-6}$. 500 μL of the cell/collagen mixture was then transferred into each well of 12-well plates (~1.3 mm height). The mixture was allowed to solidify overnight at 37° C. in an incubator then an additional 500 μL of media was added to keep the gels hydrated until treatment.

Figure 5A:
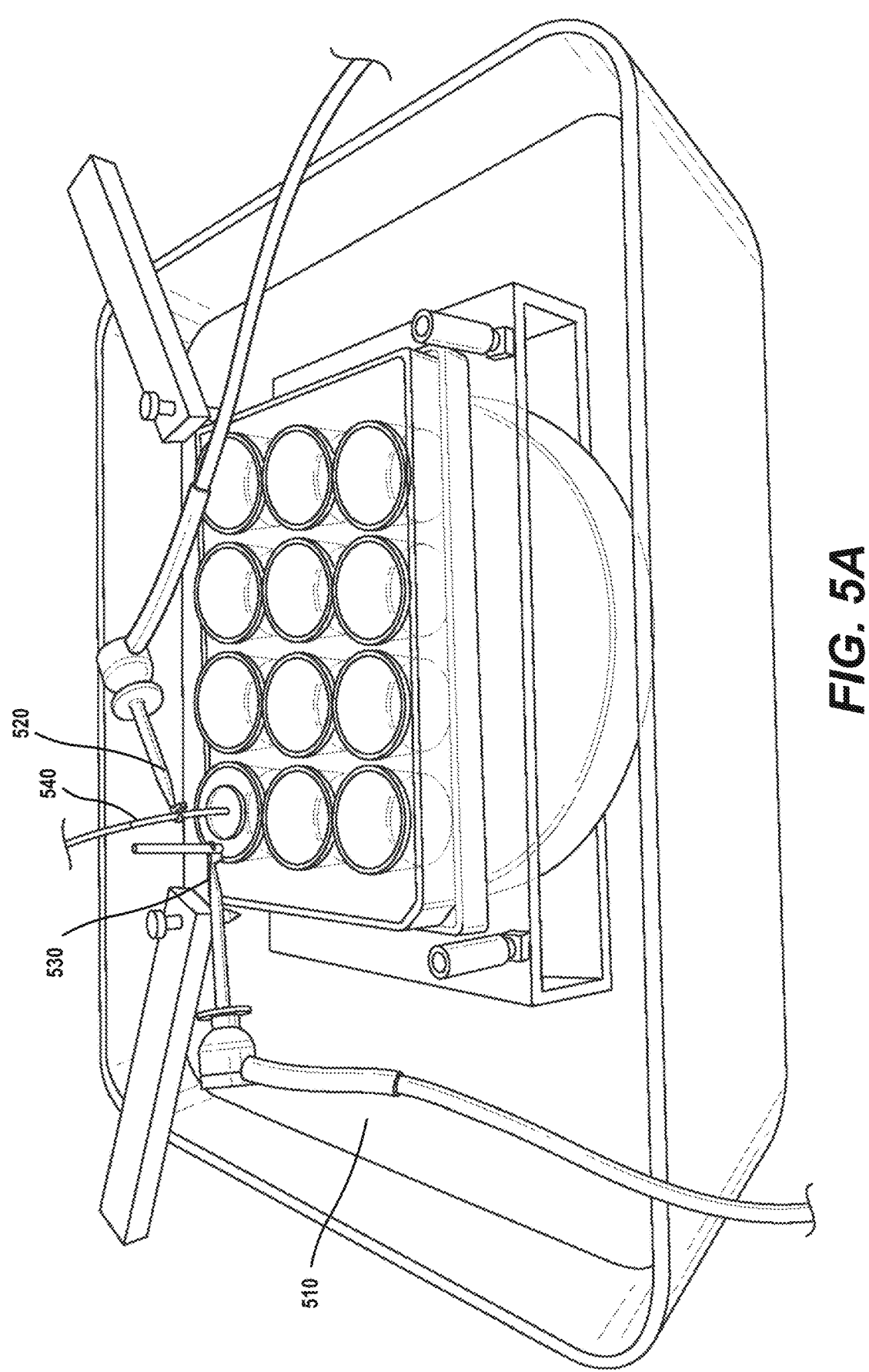
FIG. 5A illustrates an experiment in which a temperature of the target tissue may be controlled and/or measured while delivering electricity to the target tissue, according to embodiments of the present invention.

FIG. 5A illustrates an experiment in which a temperature of the target tissue may be controlled and/or measured while delivering electricity to the target tissue (e.g., the glioblastoma cells), according to embodiments of the present invention. As illustrated in FIG. 5A, the target tissue may be placed in an ice/water bath 510, with electricity provided through a source electrode 520 and a sink electrode 530. The temperature may be monitored by a temperature sensor 540.

FIGS. 5B and 5C illustrate custom ring and pin electrodes that were used for the in vitro experiments, according to embodiments of the present invention. A laser cut acrylic holder was used to secure the ring and pin flush against the bottom of the well. The outer ring was fabricated from 19 mm outer diameter 0.89 mm thick 316 stainless steel tubing (89785K259, McMaster-Carr, Douglasville, GA). The inner pin was fabricated from a 1.64 mm outer diameter blunt 304 stainless steel dispensing needle (75165A552, McMaster-Carr, Douglasville, GA). An electrical connection to the outer ring was made via a friction fit to a 1.64 mm outer diameter blunt 304 stainless steel dispensing needle. A custom pulse generator based on an H-Bridge topology was used for all experiments. Voltage and current waveforms were monitored and recorded using a custom 100 MSPS data acquisition system.

Experiments were conducted at starting temperatures between 2° C. and 37° C. by placing the cell culture plates on a hot/cold plate.

To mitigate temperature changes as a confounding factor, an automated temperature control algorithm was implemented such that a 5° C. temperature increase was achieved and maintained in all treatments. The algorithm delivered energy in "cycles" which consisted of one positive and one negative polarity pulse separated by a 1 μs delay. To simplify the discussion of these waveforms, the notation P-D-N is used where P is the positive pulse duration, N is the negative pulse duration, and D is the delay between alternating polarity pulses in the cycle; all duration have units of μs.

These cycles were initially repeated with a delay between 0.005 s (200 Hz) and 0.08 s (12.5 Hz) such that energy was delivered for 200 μs out of every second (200 μs/s) to ensure that the rate of heating was consistent between treatments with different constitutive pulse durations. This energy delivery rate ($R_{dynamic}$) was dynamically adjusted according to the following equations:

$$R_{dynamic} = \Gamma \cdot R_{initial}\left[\frac{\mu s}{s}\right] \qquad \text{[Equation 1]}$$

$$\Gamma = 0.5 - 0.9375 \cdot \gamma + 0.625 \cdot \gamma^3 - 0.1875 \cdot \gamma^5 \qquad \text{[Equation 2]}$$

$$\gamma = (T_{current} - T_{target})/(T_{target} \cdot 0.5) \qquad \text{[Equation 3]}$$

where $R_{initial}$ was 200 μsis, $T_{current}$ is the experimental temperature and $T_{target}$ is the target temperature set point. Temperature set points ($T_{target}$) of 25° C. and 42° C. were used for experiments with initial temperatures of 20° C. and 37° C., respectively. Energy was delivered according to this algorithm until the total integrated time was either 0.01 s or 0.1 s; calculated as:

$$\text{Integrated Time} = \sum_{0}^{n}(T_n + T_p) \ [s] \qquad \text{[Equation 4]}$$

where $T_n$ is the duration of the constitutive negative pulses, $T_p$ is the duration of the constitutive positive pulses, and n is the number of cycles delivered. Experimentally, treatments with symmetric bipolar waveforms and pulse durations ($T_p$ and $T_n$) of 500 ns and 1 μs were investigated. For comparison, treatments with only positive polarity 100 μs treatments were also administered using the same temperature control algorithm.

A fiber optic temperature probe (TSS, Micronor Inc., Camarillo, CA) was placed inside the center pin electrode in contact with the gel. Temperatures were acquired by a signal conditioner (Fotemp, Micronor Inc., Camarillo, CA) and recorded at 3 Hz. Post-treatment, the temperature data was averaged and is presented as mean±standard deviation. Occasional artifacts from communications errors between the signal conditioner and the pulse generator, which were registered as a 0° C. temperature, were removed in post-processing.

Figure 5D:
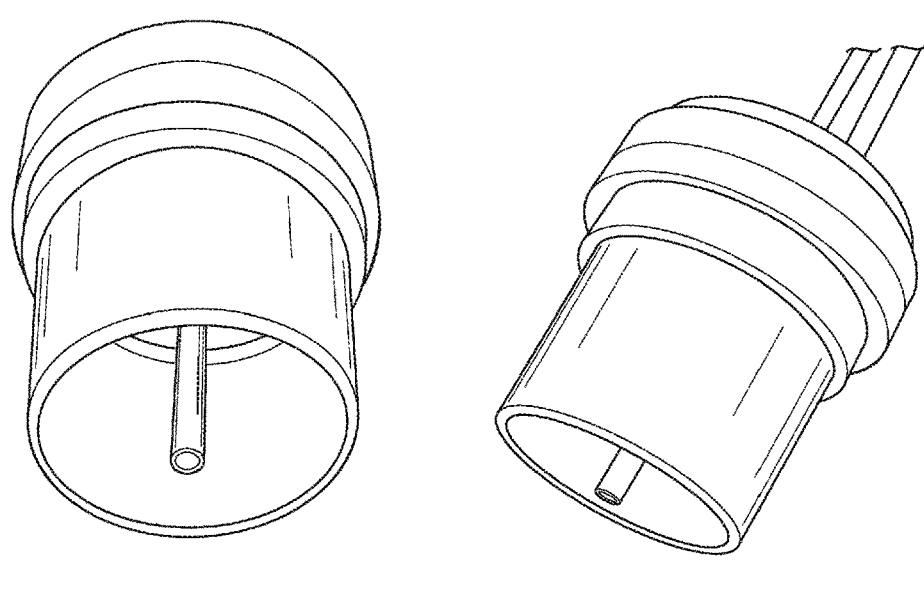
FIG. 5D illustrates a configuration of an experimental well configuration, according to embodiments of the present invention.
Figure 5D:
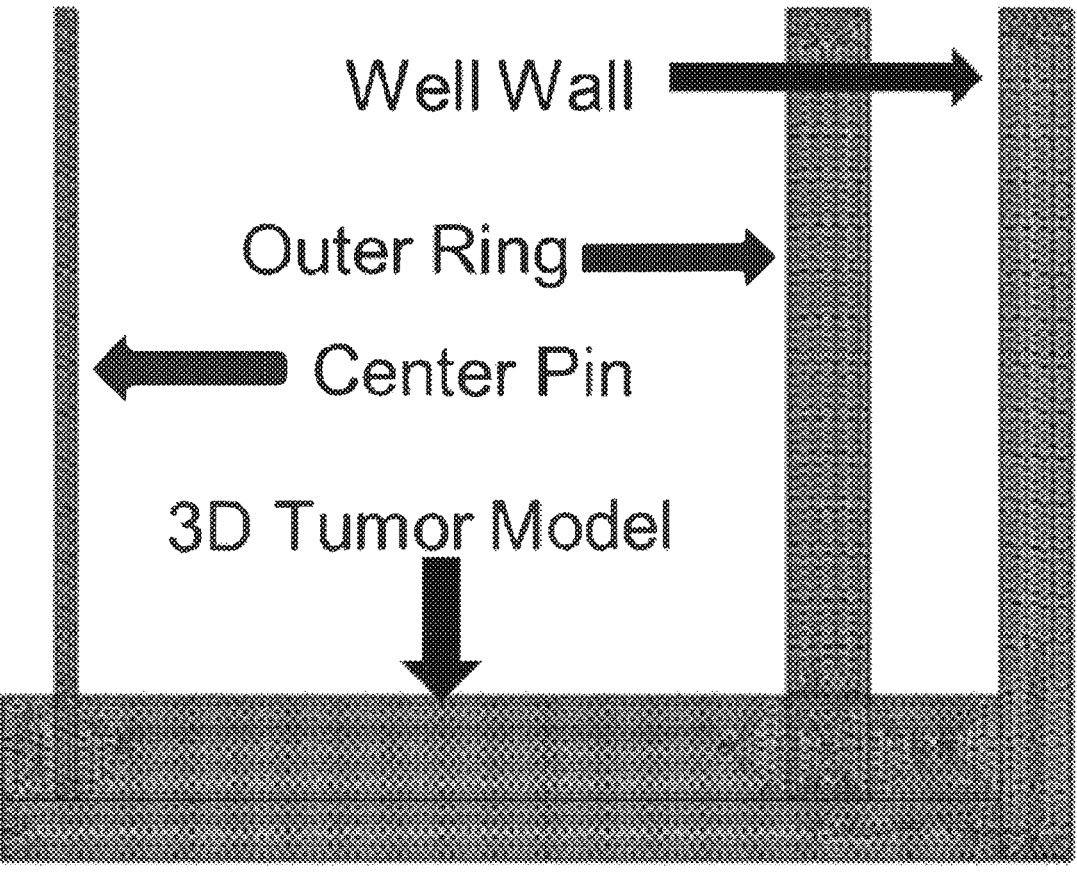

FIG. 5D illustrates a configuration of an experimental well configuration according to embodiments described herein. Geometries representing a single well within a 12-well (e.g., FIG. 5D) plate were created based on manufacturers' schematics and caliper measurements with separate domains representing the plastic well, cell culture media, and the experimental electrodes.

Experimental voltages were applied to the top most surface of the center pin electrode. The top surface of the outer ring electrode was set to ground:

$$V = 0[V] \qquad \text{[Equation 5]}$$

All external domain boundaries which did not contact another domain (e.g. the interface between plastic and air) were set as electrical insulation:

$$n \cdot J = 0 \qquad \text{[Equation 6]}$$

The electrical conductivity ($\sigma$) was set to 1.2 S/m for the media, $4 \times 10^6$ S/m for the electrodes, and $1 \times 10^{-6}$ S/m for the plastic well plate components.

Figure 5E:
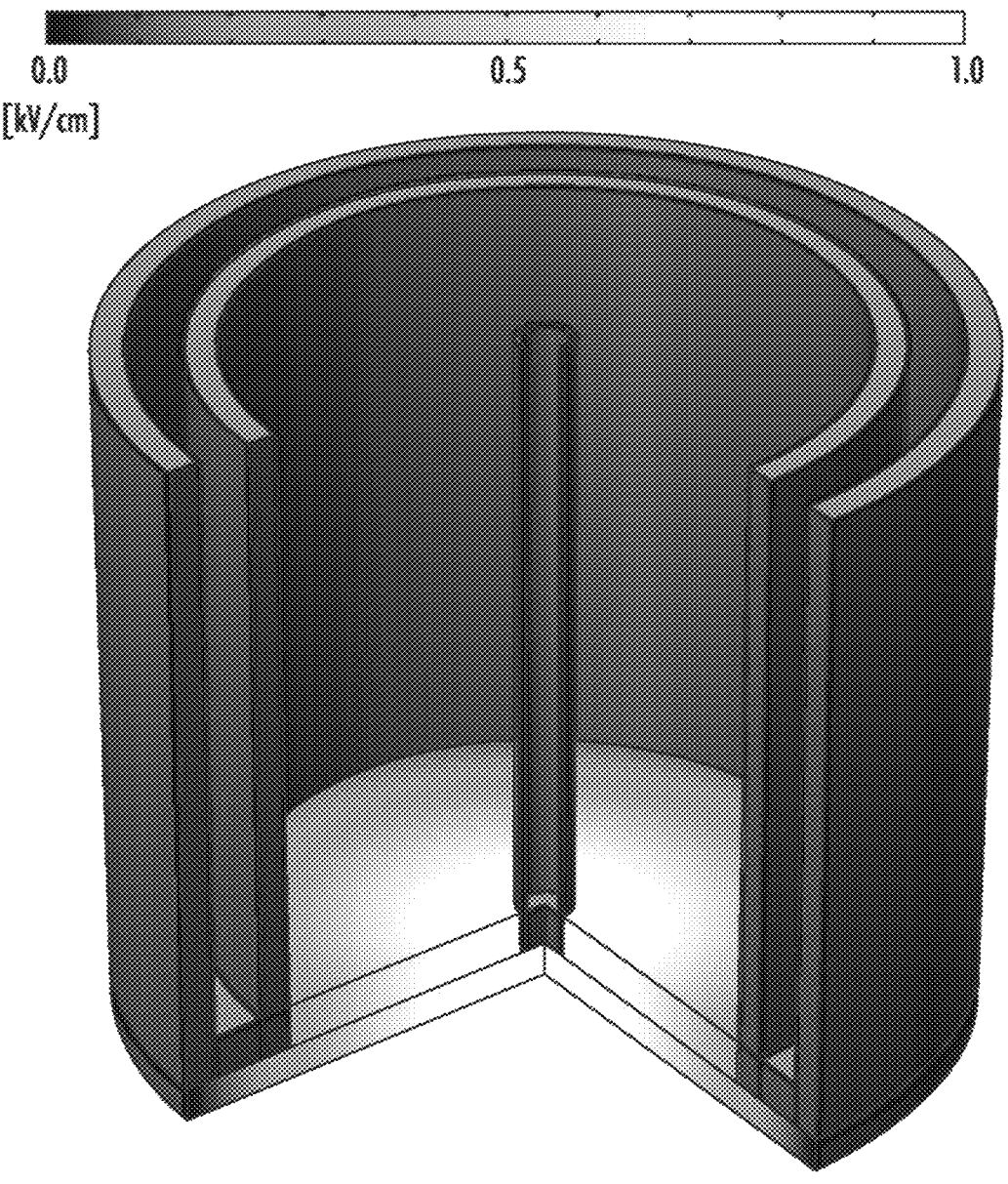
FIG. 5E illustrates an experimental electric field distribution, according to embodiments of the present invention.

A free tetrahedral mesh was generated in all domains using extremely fine mesh elements with 0.02 cm maximum and $4 \times 10^{-5}$ cm minimum mesh element sizes. For each simulation four rounds of adaptive mesh refinement were conducted using a functional error estimate with the equation mediaIntegral (ec.normE) where mediaIntegral is a $4^{th}$ order integration over the media domain and ec.normE is the electric field distribution. The initial mesh consisted of approximately 4450 triangular elements which increased to approximately 313,000 elements after four rounds of adaptive meshing. The simulations required approximately 7 seconds to solve for each voltage on a dual core Intel i7-7660U processor with 16 GB of RAM. FIG. 5E illustrates an experimental electric field distribution, according to embodiments described herein.

Imaging and Analysis

Following treatment, the cells were incubated for 24 hours. Then each well was stained with 2 μL of 4 μM Calcein AM (C3100MP, Invitrogen, Carlsbad, CA) to identify viable cells and 100 μL of 100 mg/mL propidium iodide (0219545825, MP Biomedicals, Santa Ana, CA) to identify dead cells using a Leica DMi8 microscope with a 4.2 megapixel digital camera (DFC9000GT, Leica Inc., Wetzlar, Germany). Images of the entire well were captured at 1.25× and 2.5× and stitched together using the microscope's software (LASX, Leica Inc. Wetzlar, Germany). The electrode geometry used produced a circular region of cell death which was measured horizontally, vertically, and twice diagonally (diameter, mm) and correlated to a finite element model (e.g., FIG. 5E) to determine the electrical field strength at the margin between cell death and cell viability. Values from these measurements and calculates are presented as mean±standard deviation.

Temperature Regulation

Figure 6A:
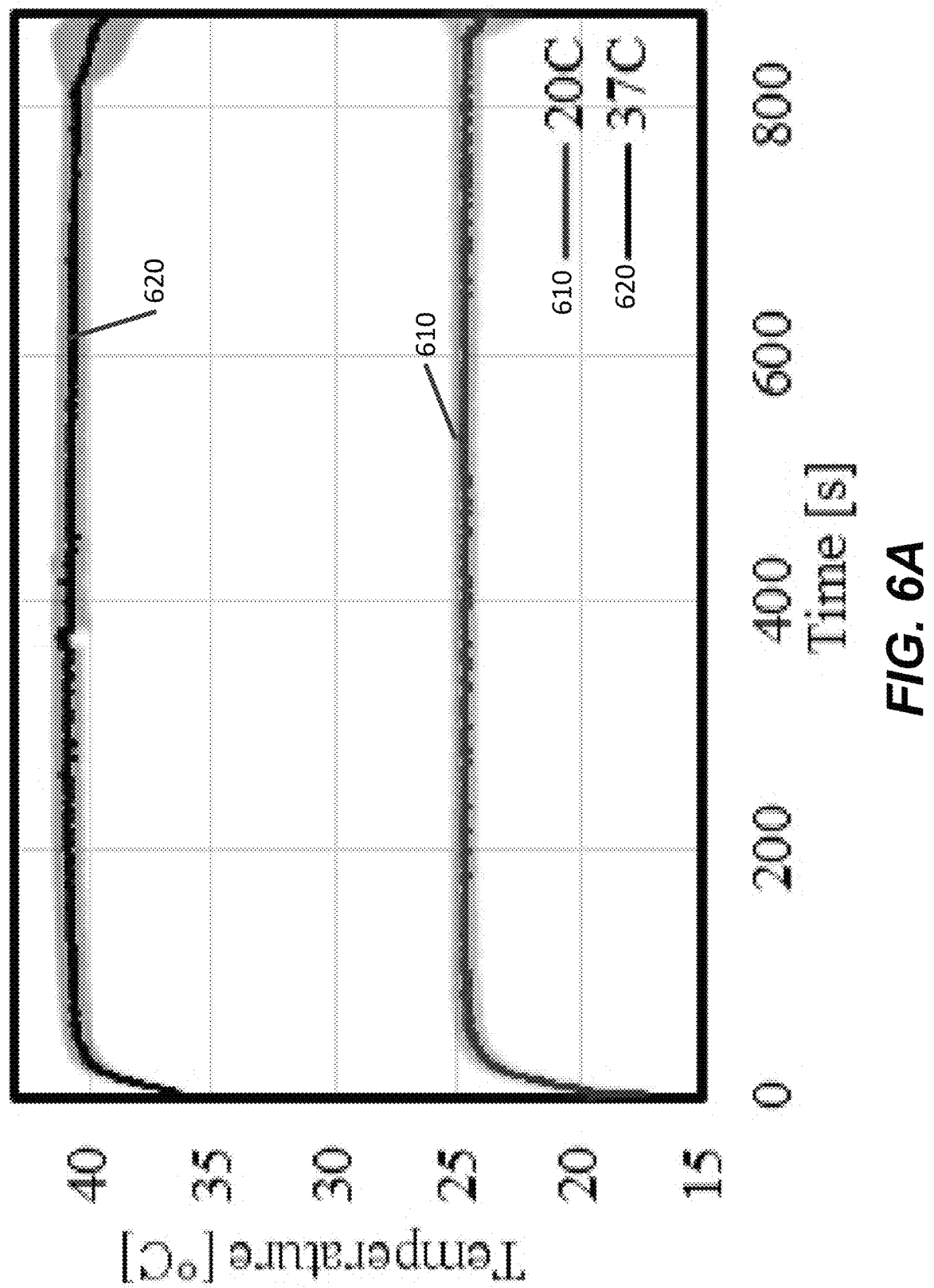
FIG. 6A illustrates temperature profiles for representative 0.1 s integrated time treatments with initial temperatures of 20° C. and 37° C., according to embodiments of the present invention.
Figure 6B:
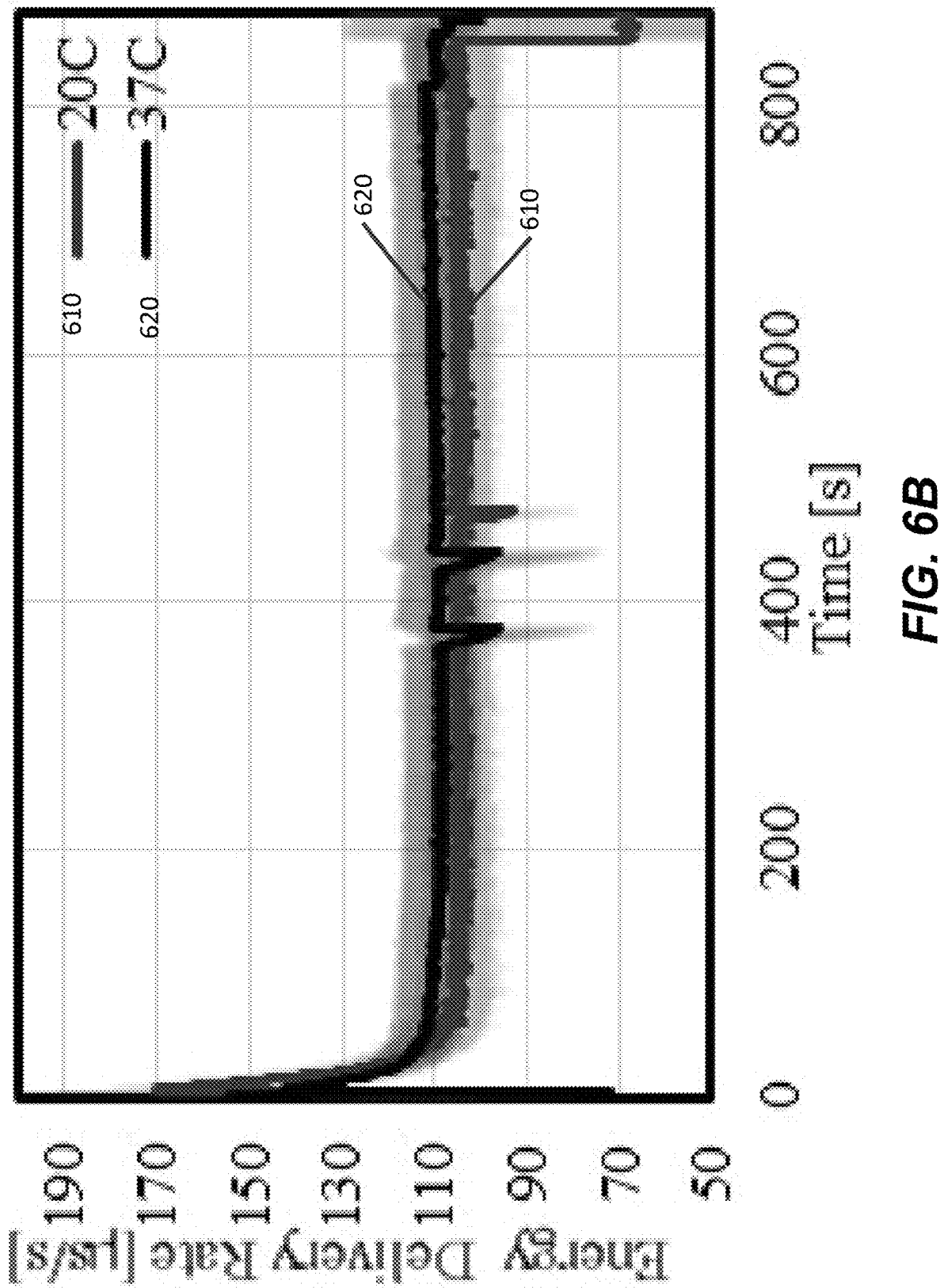
FIG. 6B illustrates dynamic energy delivery rates throughout the treatments with initial temperatures of 20° C. and 37° C., according to embodiments of the present invention.

FIG. 6A illustrates temperature profiles for representative 0.1 s integrated time treatments with initial temperatures of 20° C. (illustrated using reference designator 610) and 37° C. (illustrated using reference designator 620), according to embodiments of the present invention. FIG. 6B illustrates dynamic energy delivery rates throughout the treatments with initial temperatures of 20° C. (610) and 37° C. (620), according to embodiments of the present invention. Dips in the energy delivery rate of FIG. 6B mid-treatment may be due to the algorithm responding to random communication errors.

Referring to FIGS. 6A and 6B, a representative subset of temperature recordings from the 20° C. and 37° C. experiments were analyzed for treatments with an integrated time of 0.1 s. The average temperature over the first 800 s of these treatments was 24.6±0.6° C. and 40.6±0.5° C. for target set points of 25° C. and 42° C., respectively. Some variability in the treatment temperature, as reflected in the standard deviations, was observed beyond this time point due to variability in the control algorithm response which manifested as differences in the overall treatment times. A software safety feature automatically reduced the energy delivery rate if communication was lost between the pulse generator and the temperature signal conditioner. This manifested as random decreases in the energy delivery rate (FIG. 6B), which had an average value of 106.1±7.3 μs/s and 110.2±4.9 μs/s over the first 800 seconds of the 20° C. and 37° C. experiments, respectively.

Figure 7:
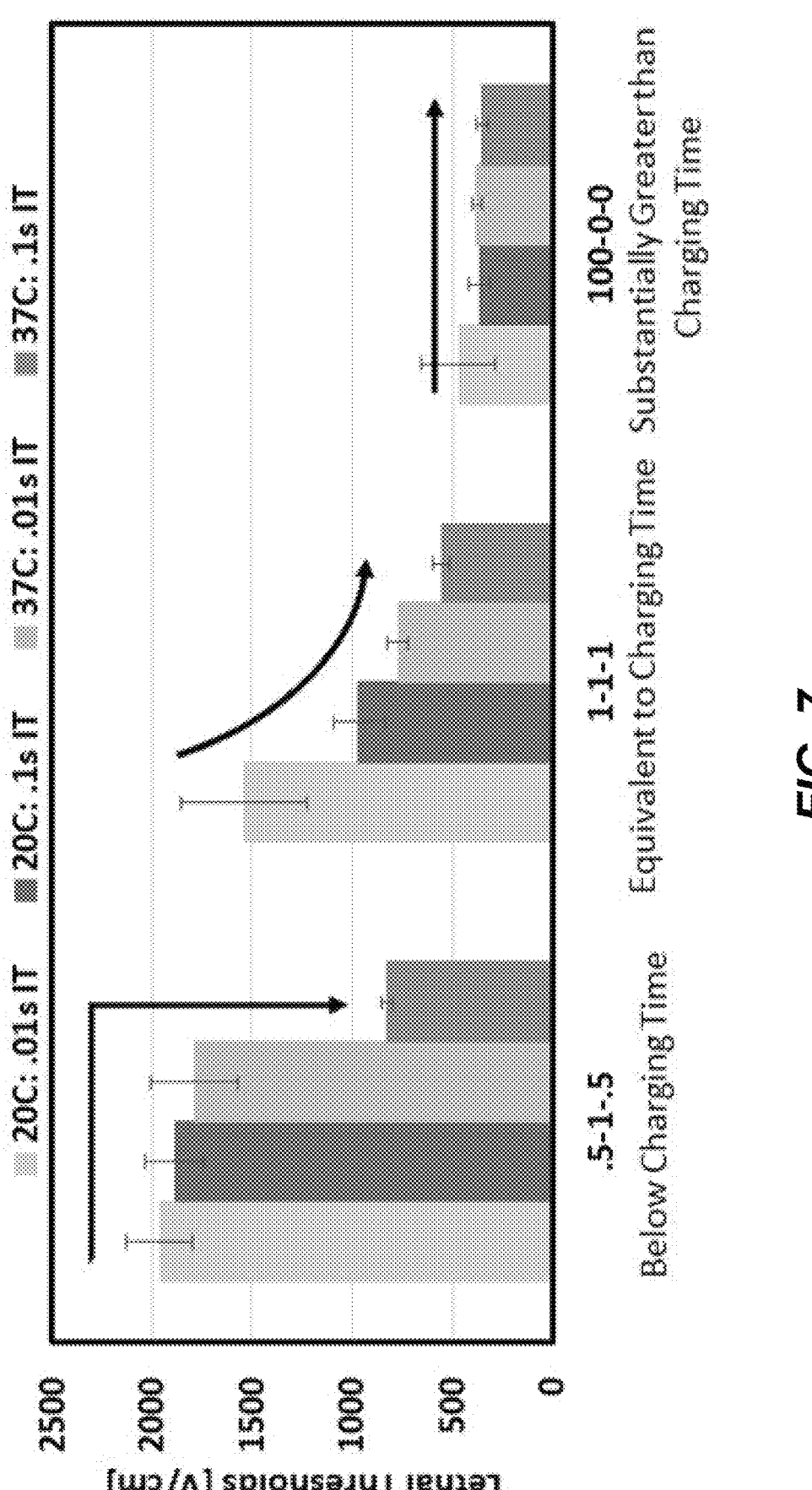
FIG. 7 illustrates a comparison of lethal thresholds for various configurations of electrical pulse delivery, according to embodiments of the present invention.

FIG. 7 illustrates a comparison of lethal thresholds for various configurations of electrical pulse delivery, according to embodiments of the present invention. Referring to FIG. 7, for pulses shorter than the cell membrane charging time (0.5-1-0.5), increases in both temperature and dose may be used for lethal effect. For pulses equivalent to the cell membrane charging time (1-1-1), temperature and dose increases enhance the lethal effect independently and further enhance lethality in combination. For pulses substantially greater than the cell membrane charging time (100-0-0), neither dose nor temperature have an impact on treatment outcomes For treatments with pulses below the charging time of the cell membrane, 0.5-1-0.5 waveform, a baseline lethal threshold of 1964±167 V/cm was found for treatments at 20° C. with a dose (e.g., Integrated Time (IT)) of 0.01 s. A significant difference was not found when the dose was increased to 0.1 s (1888±145 V/cm) or the initial temperature was increased to 37° C. (1790±219 V/cm). However, a substantial decrease in lethal threshold was found (670±173 V/cm) for treatments combining an elevated temperature (37° C.) and an increased dose (0.1 s). In contrast, treatments with pulses substantially greater than the cell membrane charging time (100 μs), increases in temperature (37° C., 0.01 s, 380±37), total dose (20° C., 0.1 s, 368±16), and the combination of these changes (37° C., 0.1 s, 353±7) did not have a substantial effect on the lethal threshold compared to baseline treatments at 20° C. with a dose of 0.01 s (472±14 V/cm). Interestingly, for treatments with pulses on the order of the cell membrane charging time, 1-1-1 waveform, increases in either temperature alone (37° C., 0.01 s, 774±52 V/cm) or total dose (20° C., 0.1 s, 970±128 V/cm) had a substantial effect on the lethal threshold compared to baseline treatments (20° C., 0.01 s, 1544±311 V/cm). For pulse durations on the order of the cell membrane charging time, 1-1-1 waveform, combining both temperature (37° C.) and dose (0.1 s) increases also had a measurable effect on the lethal threshold (558±45 V/cm).

In Vitro Demonstration of Chemical Modification of Cell Membrane Charging Time

Within the cell membrane, cholesterol plays an important role in regulating the phospholipid bilayer's thickness, fluidity, elasticity, and permeability. Cholesterol has been especially noted for mediating the effects of temperature where it has been found to provide a feedback mechanism to maintain membrane homeostasis. At low temperatures cholesterol fluidizes the membrane and reduces the membrane thickness; while, at elevated temperatures cholesterol responds by reducing membrane fluidity and increasing membrane thickness. Despite the link between temperature and membrane cholesterol, the impact of concurrent cholesterol and temperature stimulation on cell death following pulsed electric field exposure has not yet been investigated.

Figures 8A, 8B:
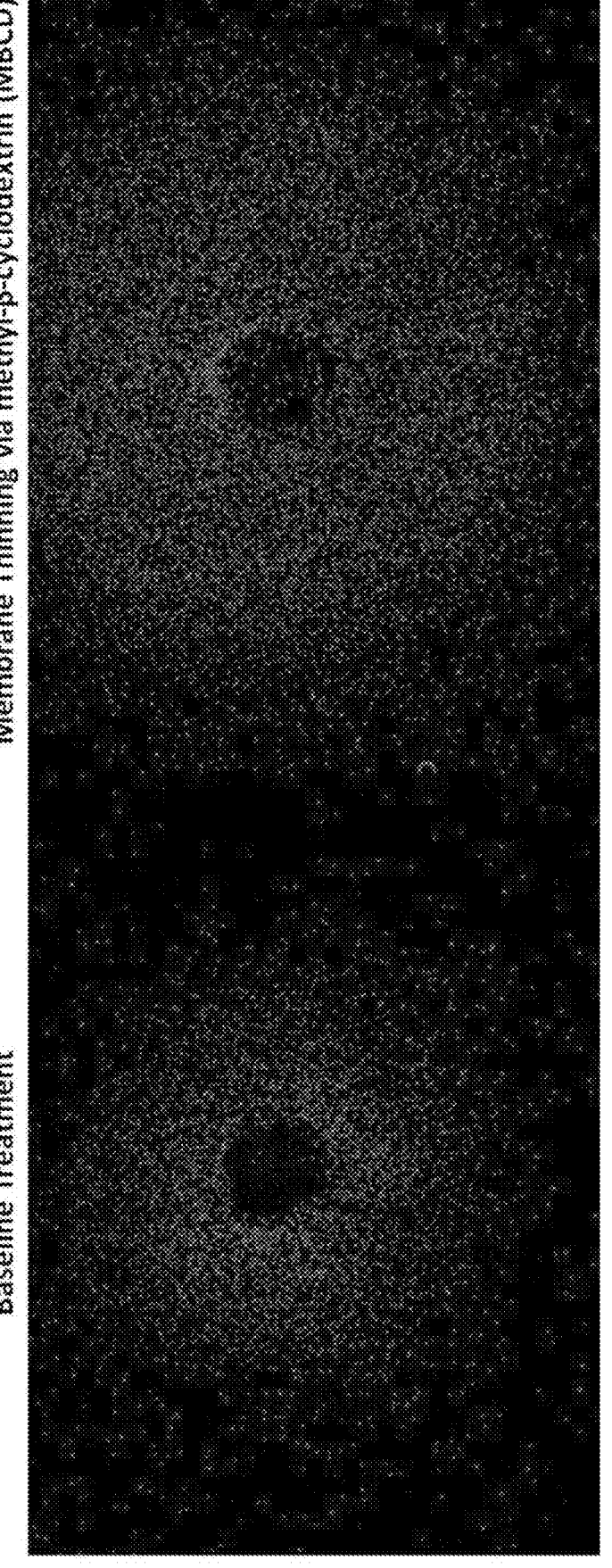
FIGS. 8A and 8B illustrate an enhancement of ablation by modifying the cell membrane charging time via removal of cholesterol from the cell membrane, according to embodiments of the present invention.

To investigate the effect of cholesterol on the cell membrane charging time, a 3D tumor model was again implemented. Cholesterol depletion was accomplished by culturing the cells with methyl-β-cyclodextrin (MβCD) prior to exposure to pulsed electric fields. MβCD works by solubilizing the membrane bound cholesterol. Following MβCD treatment, the 3D tumors were treated with 500×1000V pulses on the order of cell membrane charging time, 2-1-2 waveform with a total dose of 0.002 s. FIGS. 8A and 8B illustrate an enhancement of ablation by modifying the cell membrane charging time via removal of cholesterol from the cell membrane, according to embodiments of the present invention. Referring to FIGS. 8A and 8B, a substantial increase in ablation size was observed for 3D tumors treated with MβCD (FIG. 8B) versus the baseline treatments (FIG. 8A), indicating that membrane cholesterol depletion via chemical means may be an effective method for modifying the electrical properties of the cell membrane to make cells more susceptible to the influence of electric fields.

Cells exhibit a natural resistance to the effects of electrical pulses shorter than or on the order of the cell membrane charging time. This is likely due to the innate inability of these ultrashort electrical pulses to sufficiently charge the transmembrane potential to the critical voltage thresholds required for energy bound phenomena to occur. According to embodiments of the present invention, it is possible to modify cells in situ to make them more susceptible to the effects of electrical energy. For pulses which are substantially shorter than the cell membrane charging time, multiple techniques may be used in combination (increases in temperature and electrical dose) to achieve this effect while, for pulse durations on the order of the cell membrane charging time, it appears that a single modification (e.g., membrane thinning, temperature increase) is sufficient; there is also a clear additive effect. This indicates that it may be possible to dramatically change the cell membrane charging time through multiple combinatorial effects. Ultimately, this may enable the use of ultrashort nanosecond electrical pulses (0.1-10,000 ns) for clinical applications where enhancing the permeability of the cell membrane or induction of immediate or delayed cell death is desired.

These techniques may enable the use of ultrashort electrical pulses for targeted and focal genetic modification in vivo by providing a pathway to increase cell membrane permeability to large molecules (e.g. DNA, CAS9, CRISPR complexes) in a large volume of tissue without the induction of cell death associated with long duration electrical pulses (0.01-100 ms). Additionally, these techniques may be beneficial in oncological and surgical applications where the use of long duration (0.01-100 ms) electrical pulses cause deleterious side effects (muscle contractions, cardiac complications, electrical arcing), but ultrashort electrical pulses on their own are ineffective or incapable of killing large tumors (1-5 cm) or ablating sufficient volumes in clinically viable timeframes.

Polymer Nanoparticles and Electrotherapy

As discussed herein, tumors have previously been shown to be susceptible to pulsed electric field agonists. High voltage, short duration electric pulses can act by inducing irreparable nanoscale defects in the cell membrane. This technique has been used to treat tumors in vitro, in vivo murine model, ex vivo liver tissue, and human clinical trials. Descriptions of these techniques are discussed, for example, in B. Al-Sakere et al., "Tumor ablation with irreversible electroporation," *PloS One*, vol. 2, no. 11, pp. e1135-e1135, November 2007, M. B. Sano et al., "Bursts of Bipolar Microsecond Pulses Inhibit Tumor Growth," *Sci. Rep.*, vol. 5, p. 14999, October 2015, C. B. Arena et al., "High-frequency irreversible electroporation (H-FIRE) for non-thermal ablation without muscle contraction," *Biomed. Eng. OnLine*, vol. 10, pp. 102-102, 2011, M. B. Sano, R. E. Fan, G. L. Hwang, G. A. Sonn, and L. Xing, "Production of Spherical Ablations Using Nonthermal Irreversible Electroporation: A Laboratory Investigation Using a Single Electrode and Grounding Pad," *Spec. Issue Interv. Oncol.*, vol.

27, no. 9, pp. 1432-1440.e3, September 2016, and S. Dong, H. Wang, Y. Zhao, Y. Sun, and C. Yao, "First Human Trial of High-Frequency Irreversible Electroporation Therapy for Prostate Cancer," *Technol. Cancer Res. Treat.*, vol. 17, pp. 1533033818789692-1533033818789692, July 2018.

A common denominator between all of these studies is a fundamental limitation whereby the volume of affected cells cannot exceed the volume circumscribed by a threshold electric field emitted by an applicator electrode. Currently, in order to increase the treatment zone, the energy delivered must be increased by increasing the pulse amplitude. As a consequence, a larger ablation is accompanied by an increase in tissue heating, thermal damage, and potentially dielectric breakdown at the air-tissue interface.

Recently, there has been an interest in expanding the volume of ablations without the need for increased energy delivery or number of treatments. This aim focuses on utilizing nanotechnology to make an individual cell more susceptible to the electric field application.

An ablation augmentation technique which requires further examination is the use of polymer based nanoparticles to modify the charging time of cell membranes. The advantage of synthetic polymer nanoparticles is that their size, surface charge, and composition are tunable, as discussed in J. W. Hickey, J. L. Santos, J.-M. Williford, and H.-Q. Mao, "Control of polymeric nanoparticle size to improve therapeutic delivery," *J. Control. Release Off. J. Control. Release Soc.*, vol. 219, pp. 536-547, December 2015. Such tuning could be done to enhance the lethality of electric field exposure or enable greater nanoparticle accumulation in the tumor tissue, as discussed in N. Kamaly, B. Yameen, J. Wu, and O. C. Farokhzad, "Degradable Controlled-Release Polymers and Polymeric Nanoparticles: Mechanisms of Controlling Drug Release," *Chem. Rev.*, vol. 116, no. 4, pp. 2602-2663, February 2016. Additionally, nanoparticles can encapsulate drugs, proteins, or gene targets to increase lethality and bioavailability while minimizing side effects, as discussed in M. H. El-Shabouri, "Positively charged nanoparticles for improving the oral bioavailability of cyclosporin-A," *Int. J. Pharm.*, vol. 249, no. 1, pp. 101-108, December 2002.

The use of polymer nanoparticles to reduce the critical electric field for inducing cell death and increase the size of a given ablation will be discussed herein that uses a polyethylenimine nanoparticle (PEI-NP). PEI-NPs have been shown to be capable of increasing the size of a pulsed electric field ablation in an in vitro 3D culture model while having a minimal effect on cell viability, cell media conductivity, and nanoparticle properties of size and charge. The related discussion herein demonstrates the synergy of polymer nanoparticles and pulsed electric fields for the treatment of cancer, and provides evidence for the design of electrical therapy specific and optimized polymer nanoparticles.

Cell Culture for Polymer Nanoparticle Analysis

Human glioblastoma cells (U118) (ATCC, Manassas, VA) were utilized. U118 cells were cultured in a complete media made of Dulbecco's modified Eagle's medium (DMEM) (11965118, Gibco) supplemented with the combination of fetal bovine serum (A3160402, Gibco) and penicillin/streptomycin (15070063, Gibco). Complete cell media changes were conducted every 72-96 hours. The cells were passaged via trypsinization upon reaching 75-85% confluency. Passages 9-12 were used for all experiments. Throughout incubation the cells were maintained at 37° C. in a humidified incubator with 5.0% $CO_2$.

For all PEI-NP and pulse electric field (PEF) treatments the cells were placed in a collagen matrix. The cells were counted using a fluorescence based automated cell counter (Luna, Annadale, VA) and diluted to $1\times10^6$ cells/mL. The cell suspension was mixed with an equal volume of PureCol Ez made of Type 1 bovine collagen (Advanced Biomatrix, San Diego, CA). The combination was then put in to either a 12-well plate with $0.25\times10^6$ cells per well or a 48-well plate with $0.0625\times10^6$ cells per well. The gels were allowed to solidify in the incubator for 24 hours before either 500 μL or 125 μL of complete media was added to each well of the 12 or 48-well plate respectively.

Nanoparticle Formulation and Characterization

Branched polyethylenimine (PEI) was obtained at molecular weight (MW)=10,000 g/mol (99%, PolySciences, Warrington, PA), and MW=750,000 g/mol (Mn=~60,000 g/mol) at 50% (w/v) in $H_2O$ (analytical standard, Sigma-Aldrich, St. Louis, Mo.). Bovine serum albumin (BSA) and ACS grade acetone were acquired from Fisher Scientific (BSA, Pittsburgh, PA). ACS grade tannic acid (TA) and FITC-BSA were purchased from Sigma-Aldrich (St. Louis, MO). These materials were used as received.

Figure 9A:
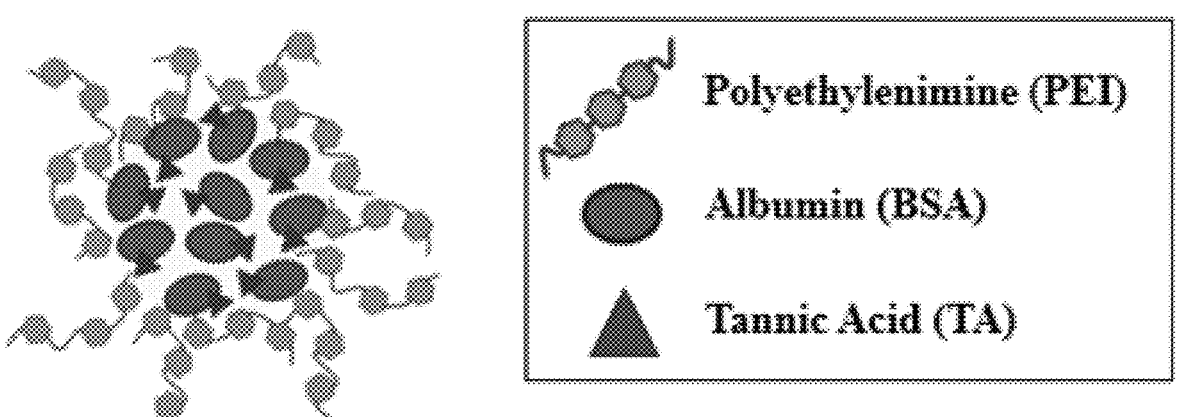
FIGS. 9A and 9B illustrate the formation and characterization of PEI-NPs, according to embodiments of the present invention.
Figure 9B:
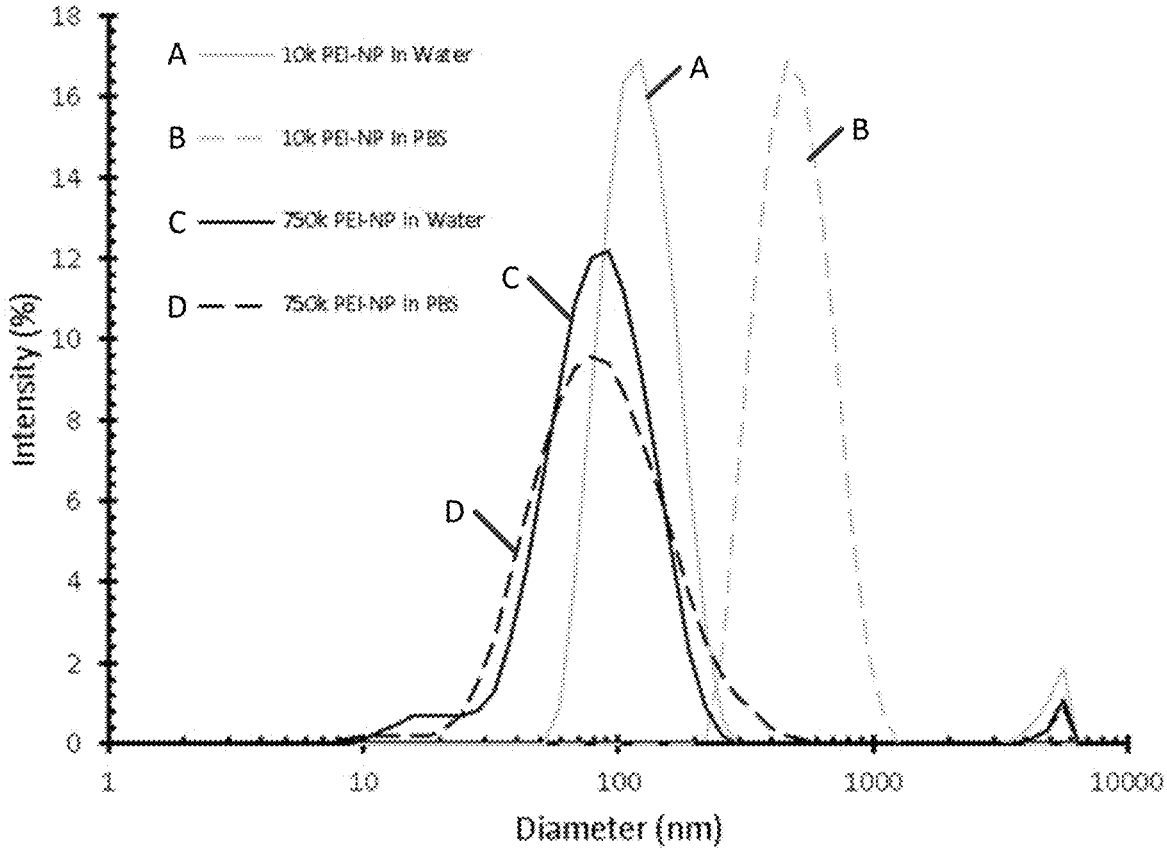

Polyethylenimine nanoparticles (PEI-NP) encapsulating BSA and TA were formulated by Flash NanoPrecipitation (FNP) stabilized via electrostatic interaction between anionic protein and cationic polymer. FIGS. 9A and 9B illustrate the formation and characterization of PEI-NPs, according to embodiments of the present invention. As illustrated in FIG. 9A, PEI-NPs are formulated via FNP. Albumin and tannic acid form a negatively charged insoluble complex that is electrostatically stabilized with cationic PEI forming stable nanoparticles. The characterization of PEI-NPs by dynamic light scattering is shown in FIG. 9B. The solid lines indicate initial nanoparticle size of 10 k and 750 k PEI-NPs suspended in water. After 7 days, the nanoparticles were suspended in PBS to mimic cell culture conditions and characterized (dotted lines). The 10 k PEI-NPs increase in size in PBS to ~500 nm while the 750 k PEI-NPs remain ~100 nm in PBS.

To synthesize the particles used for these experiments, TA (5 mg/mL) was dispersed in acetone and sonicated at ~40° C. for 5 minutes and BSA (9 mg/mL) was dissolved in deionized water by mixing until macroscopically homogenous. Nanoparticles formulated with FITC were prepared with 1% w/w FITC-BSA in the total BSA stream. Then, the TA solvent stream and the BSA stream were rapidly mixed in a hand-operated confined impinging jet mixer at equal volume of 0.5 mL and immediately diluted in 4 mL reservoir containing PEI (4.2 mg/mL) to maintain an acetone/water ratio of 1:9 by volume. Either the 10 k MW PEI or the 750 k MW PEI were added to the reservoir to produce 10 k and 750 k PEI-NPs, respectively. The concentration of PEI was at a 3:1 ratio of the PEI to the core (BSA/TA) for particles made both molecular weights of PEI. The nanoparticles were stored at 4° C.

The nanoparticles were characterized by size, polydispersity, and zeta potential immediately following formulation. The size and polydispersity index (PDI) of the nanoparticles was measured by dynamic light scattering (DLS) with a Malvern Zetasizer ZS (Malvern Instruments Ltd, Malvern, United Kingdom). DLS measurements were performed using normal resolution model intensity with a backscatter detection angle of 173°. The mean particle size and distribution are reported by averaging 4 measurements. (See FIG. 9B.) The surface charge was measured by zeta potential using Malvern Zetasizer ZS and was reported as an average of 4 measurements.

Pulsed Electric Field Delivery

The applicator electrode was coaxial in geometry and designed to fit in a 12-well culture plate. A computational electromagnetic simulation using a finite element analysis of this setup has been previously demonstrated and confirmed by practice, as discussed in Michael B. Sano, Christopher C. Fesmire, Matthew R. DeWitt, and Lei Xing, "Burst and continuous high frequency irreversible electroporation protocols evaluated in a 3D tumor model," *Phys. Med. Biol.*, vol. 63, no. 13, p. 135022, 2018. Briefly, a securing ring was laser cut from acrylic stock in order to maintain the electrode element spacing and ensure a secure fit into the culture plate. The outer conductor was fabricated from 19 mm outer diameter 0.89 mm thick 316 stainless steel tubing (McMaster-Carr, Douglasville, GA). The inner electrode was a 1.64 mm outer diameter blunt 304 stainless steel dispensing needle (McMaster-Carr, Douglasville, GA). (See, e.g., FIGS. 5B and 5C.) Connections between the pulse generator and the power supply were made through high voltage test clips.

Figure 10:
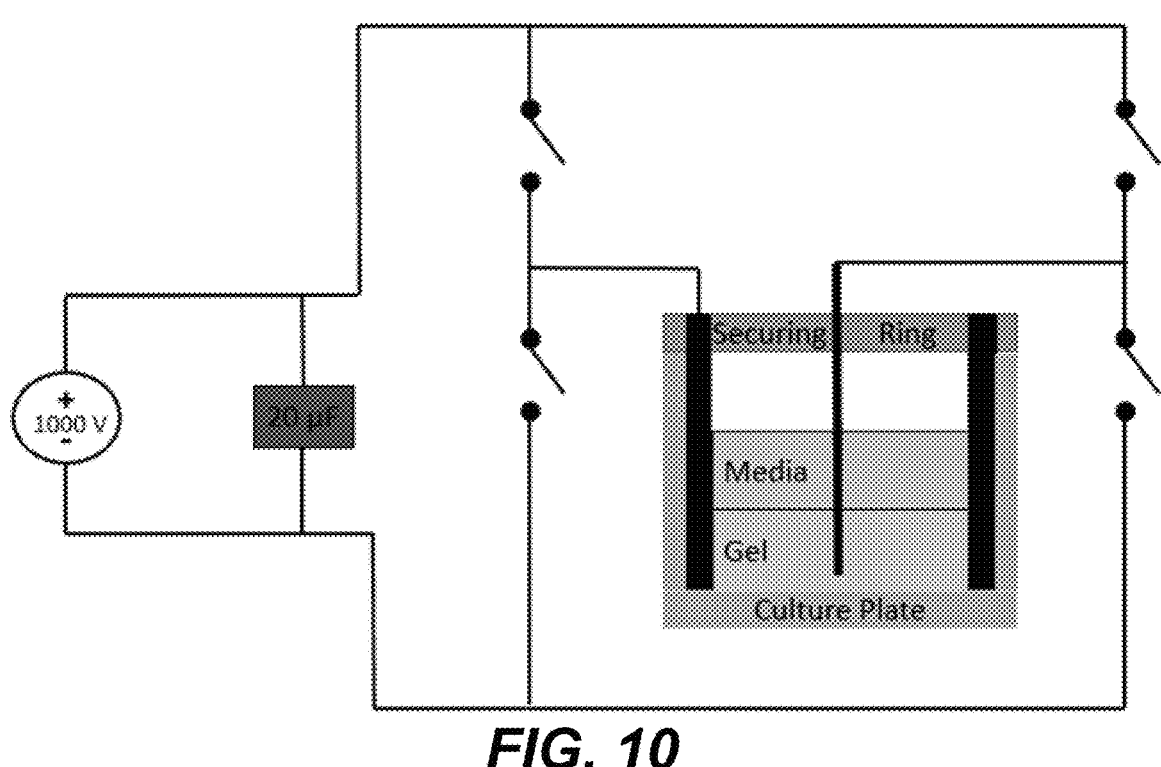
FIG. 10 illustrates an experimental setup and circuit diagram for a power supply, according to embodiments of the present invention.

The pulse power supply was a square wave generator based on capacitive discharge. For this generator, the capacitor bank was 20 μF. This was switched through a solid state switching module (Behlke Power Electronics GmbH, Taunnus, Germany). Alternating polarity pulses were created by utilizing an H bridge topology. FIG. 10 illustrates an experimental setup and circuit diagram for a power supply, according to embodiments of the present invention. The circuit consists of a 1 kV DC power supply, capacitor bank, and H-bridge switch. The cross section of the biological load in FIG. 10 shows the coaxial electrode, securing ring, gel in which the cells are embedded, and culture media containing PEI-NPs. The analog output voltage and current were recorded using a 1:1000 DP03-1 kV-50 differential probe (CIC Research, San Diego, CA) and a 0.01 V/A Pearson current transformer (Pearson Electronics, Palo Alto, CA) respectively. The waveforms were sampled and displayed using 100 MS/s data acquisition system.

Figures 11A, 11B, 11C:
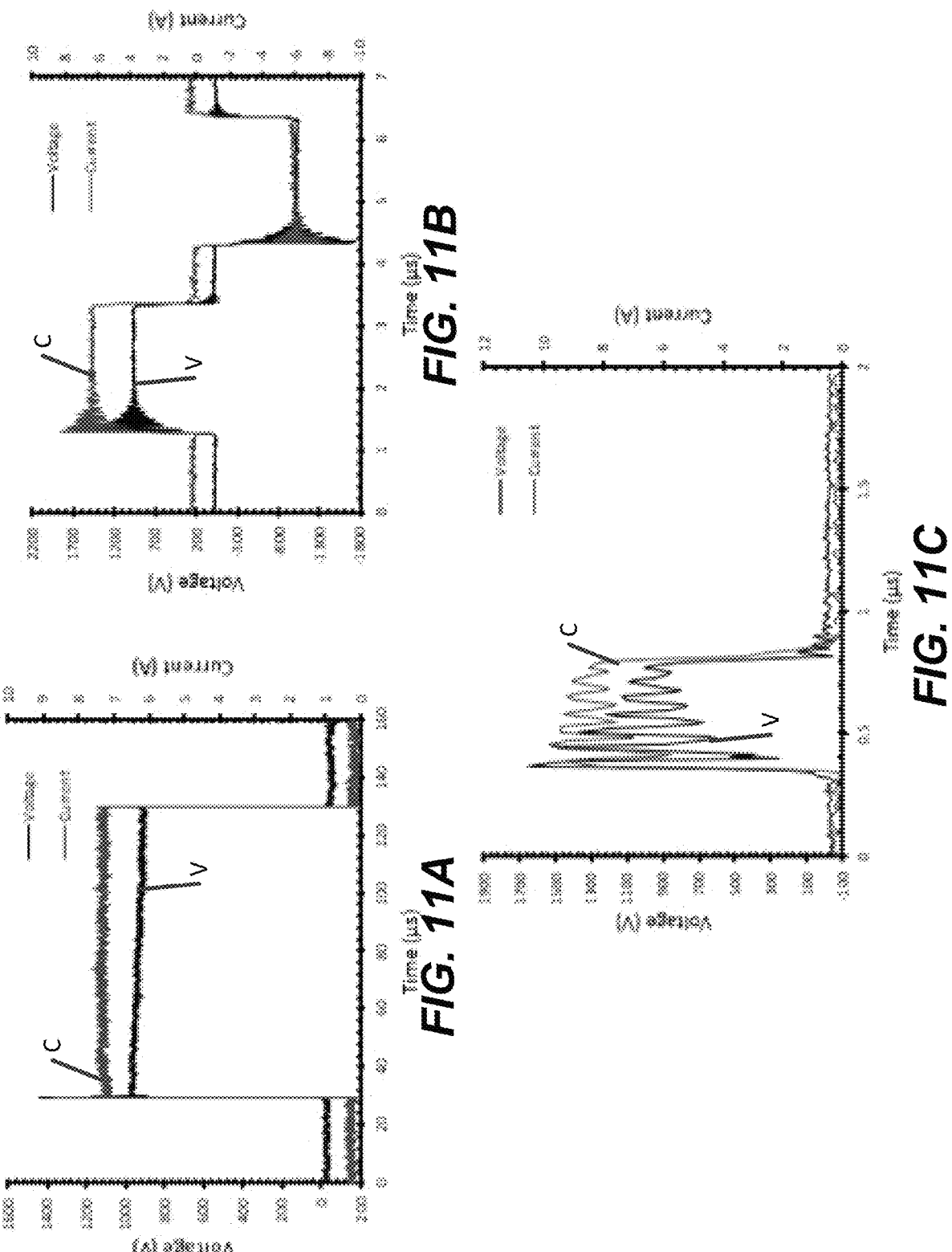
FIGS. 11A-11C are waveforms that illustrate voltage and current transients, according to some embodiments described herein.

For this study, one representative pulse from three time domains was selected for experimentation and comparison. Low Frequency is exemplified by long monopolar pulses. For this experiment, 100 μs pulses were used (LF Waveform). High Frequency pulses were bipolar pulses characterized by a 2 μs positive phase, 1 μs delay, and a 2 μs negative phase (HF Waveform). Nanosecond duration pulses (nsPEF) were characterized by 400 ns monopolar pulses. FIGS. 11A-11C are waveforms that illustrate voltage and current transient used in the experiments. FIG. 11A illustrates the LF waveforms, FIG. 11B illustrates the HF waveforms, and FIG. 11C illustrates the nsPEF waveforms. In FIGS. 11A to 11C, reference designator 'V' is used to illustrate the voltage waveforms and reference designator 'C' is used to illustrate the current waveforms.

In order to attribute equal dosing consideration between pulse time domains, the number of pulses and repetition rate were adjusted. The voltage was held constant for all three pulse parameter. Dosing was done along two key parameters: pulse delivery rate and total pulse on time described by the integrated energized time (IET). For all of the experiments, the pulse delivery rate was 100 μs/s. This indicates 100 μs of applied voltage for each second of treatment time calculated by $R_{energy}=t_{on}/t_{total}$. The integrated energized time is 0.002 s. This is described by the sum of applied voltage time across the entire treatment, given by $t_{IET}=\Sigma t_{on}$. A full accounting of the pulse transient parameters is given in Table 2

TABLE 2

| Time Domain | Pulse Width (μs) | Number of Pulses (N) | Inter-pulse Time (s) | Frequency (Hz) | Amplitude (V) |
|---|---|---|---|---|---|
| LF Waveform | 100 | 20 | 0.999 | 1 | 1000 |
| HF Waveform | 2+ and 2− | 500 | 0.04 | 25 | 1000 |
| nsPEF | 0.4 | 5000 | 0.004 | 250 | 1000 |

Effects of PEI-NPs on Cell Media Conductivity

It was of interest to determine what role the PEI-NPs have on the electrical properties of the bulk media as it could change the electric field the cells experience and be used to explain any changes in irreversible electroporation. To test this potential a LaquaTwin EC-33 conductivity meter (Horiba, Kyoto, Japan) was used to test PEI-NP solutions at a concentration $3.4 \times 10^{4}$-5.6 mg/mL in complete media (in addition to complete media alone). Initially, the meter was calibrated using two standard solutions, one at 1.41 mS/cm and another at 12.9 mS/cm. For each individual reading, 125 μL of sample solution was placed into the meter and the reading was recorded. Between samples the meter was washed out twice with deionized water and the meter was dried with compressed air.

Effects of Pulsed Electric Field on Particle Stability

The addition of energy, both electrical and thermal, as well as the generation of reactive species have the potential to alter or degrade the PEI-NP's properties, as discussed, for example, in Y. Xia and J. Ouyang, "Salt-Induced Charge Screening and Significant Conductivity Enhancement of Conducting Poly(3,4-ethylenedioxythiophene):Poly(styrenesulfonate)," Macromolecules, vol. 42, no. 12, pp. 4141-4147, June 2009. To investigate this response, the 10 k and 750 k PEI-NPs were treated with pulse electric fields without the presence of cells while suspended in phosphate buffered saline solution (PBS). For this experiment, 1 mL of PEI-NP solution in PBS at a concentration of $4.38 \times 10^{-2}$ mg/mL was treated with pulse electric fields. The coaxial electrode was used to deliver one of the LF Waveform, HF Waveform, and nsPEF pulse sequences stated in Table 2. After pulse application the size and PDI of the nanoparticles was determined with DLS. Additionally, the zeta potential surface charge of the NPs was measured with the Zetasizer ZS, as previously described.

Propidium Iodide Calibration

For combined PEI-NP and PEF experiments, propidium iodide (PI) was selected as a marker for cell membrane integrity, the loss of which is a hallmark of cell death by irreversible electroporation. Because cationic species are inherently cytotoxic and capable of interfering with the PI signal, a calibration assay was initially conducted in order to establish a working concentration of PEI-NPs to be used for the combined PEI-NP and electric field treatments. The working concentration is designated as the peak PEI-NP loading which does not cause significant increase in propidium iodide (PI) signal with respect to the untreated sample over the experimental time period.

Figure 12:
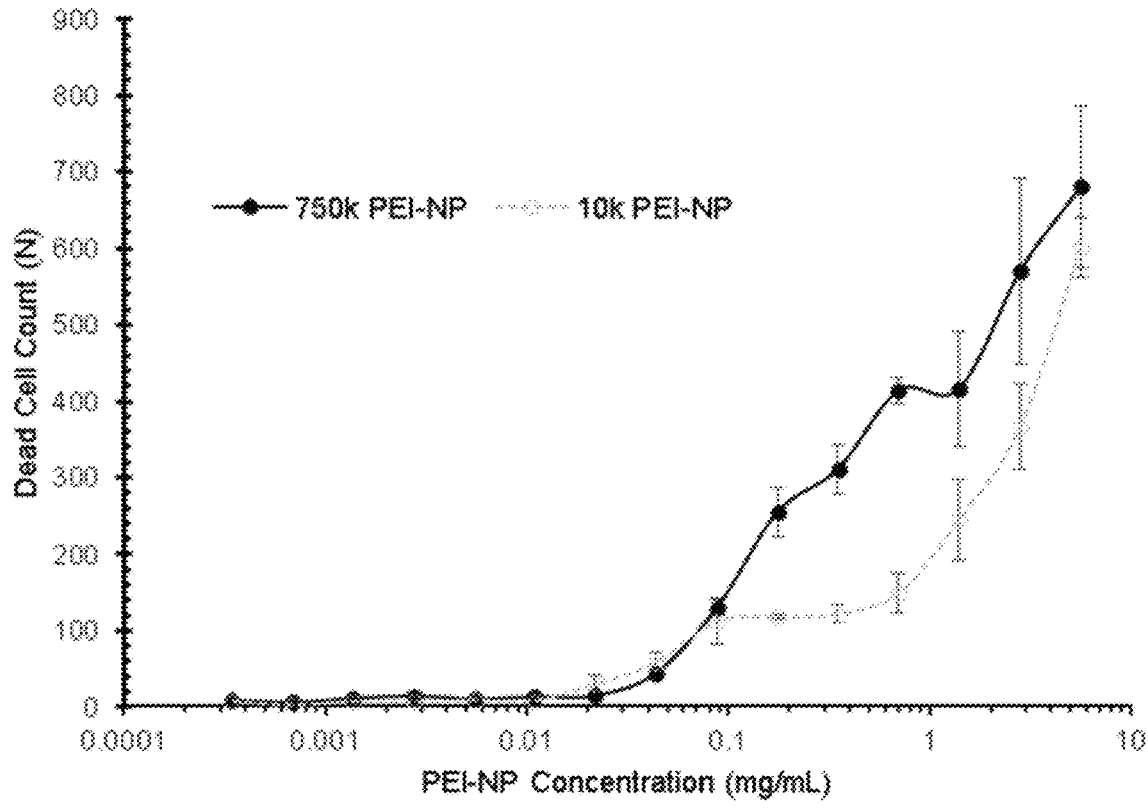
FIG. 12 is a graph that illustrates the dead cell count as a function of PEI-NP concentration, according to some embodiments of the present invention.

A dilution series consisting of complete media and PEI-NPs was created with concentrations between $3.4 \times 10^{-4}$-5.6 mg of total PEI-NP solids/mL. Each respective solution was added to cells in gel plated on a 48-well plate. Cells were allowed to incubate for 2 hours. After the given time, 25 μl of 1 mg/mL PI (ThermoFisher, Waltham, MA) was added. An additional 30 min of incubation was given for PI to bind to the DNA. The number of cells taking up PI was determined using fluorescence microscopy combined with cell counting. Imaging was done Leica DMi8 microscope (Leica Inc., Wetzlar, Germany) with images being taken at 5× magnification, excitation/emission of 493/636, exposure of 200 ms, and a Texas Red filter. Three images were taken in different wells for each concentration for each nanoparticle (750 k and 10 k PEI-NPs) at each concentration. The dead cells were counted using a Matlab (MathWorks, Natick, MA) script which in addition to counting the cells implemented a threshold pixel intensity and removed small artifacts. A hand count was done on one of each triplicate (n=3) image set to confirm the accuracy of the count. From this assay the number of dead cells as a function of nanoparticle concentration was determined. FIG. 12 is a graph that illustrates the dead cell count as a function of PEI-NP concentration, according to some embodiments of the present invention. As illustrated in FIG. 12, PEI-NPs are cytotoxic at high concentrations. Referring to FIG. 12, for low concentrations below $4.38 \times 10^{-2}$ mg/mL for 10 k PEI-NPs and $8.75 \times 10^{-2}$ mg/mL for 750 k PEI-NPs, there was no difference detected in the number of cells up taking PI relative to the untreated controls.

To select the working NP concentration for later experiments, a Tukey's Honestly Significant Difference (HSD) test from a post-hoc analysis of ANOVA was used to identify concentrations that were different than the untreated sample. A concentration of PEI-NPs was determined to be statistically different than the control at a significance level α=0.05. For U118 cells the range of PEI-NP concentrations which were statistically similar to the untreated control were $\leq 4.38 \times 10^{-2}$ mg/mL for 10 k PEI-NPs and $\leq 8.75 \times 10^{-2}$ mg/mL for 750 k PEI-NPs. To create the condition where the NPs could be compared for their enhancement of irreversible electroporation, the same working concentration was selected for both. A concentration of $4.38 \times 10^{-2}$ mg/mL was selected as the working concentration of PEI-NPs to be used for further experiments.

Internalization of PEI-NPs

It was of interest to gain insight into the PEI-NP and cell membrane interaction by determining whether the PEI-NPs could inherently cross the cell membrane. For this fluorescently labeled FITC-BSA, PEI-NPs were added without an applied electric field to cells plated in 2D on the culture dish at the working concentration. For visualization the cell nuclei were additionally stained with 100 μL of 5 μg/mL Hoechst (ThermoFisher, Waltham, MA). After 2 hours, the cells were washed twice with PBS to remove the extracellular PEI-NPs. Images were then taken at 20× using an excitation emission of 361/497 and exposure of 10 ms for Hoechst and 485/535 with 250 ms for the FITC-BSA core PEI-NP. Following imaging, the percent uptake was determined by manually counting the cells which uptake FITC-BSA compared to the total number of cells characterized by the uptake of Hoechst.

Combination PEI-NP and Pulsed Electric Field Treatment

One aim of this experiment was to determine if the PEI-NPs would enhance cell death following electric field exposure. Considering an individual treatment, the cells were plated in the 3D culture model described in the cell culture method. For a combined PEI-NP and pulsed electric field treatment, the PEI-NPs were added at the working concentration along with complete media for a total volume of 500 μL. For the control group no PEI-NPs were added. The cells were then subjected to pulsed electric fields utilizing three different pulsing parameters (Table 2). All trials were performed in triplicate (n=3) for both 10 k PEI-NP 750 k PEI-NP, and without PEI-NP. After pulse delivery, the cells were placed in the incubator for 60 min to insure that the dye uptake was not due to transient pore opening where the cell membrane could be permeable to PI. After this time period, the cells were stained simultaneously with both 100 μl of 1 mg/mL of propidium iodide (PI) and 2 μL of 4 μM Calcein AM (ThermoFisher, Waltham, MA). PI was used as an indicator of cell death by describing cell membrane integrity; whereas, Calcein AM indicates the live cells by esterase metabolism. After 30 min of incubation the cells were washed in PBS to remove background dye. In accordance with PI and Calcein AM fluorescence (excitation/emission of 493/636 and excitation/emission of 495/515 respectively), the whole well plate was imaged at a magnification 1.25× with an exposure time of 100 ms. The resulting images were stitched together using Leica LASX software.

Image analysis was done to describe the effect of the treatments. Spatially, the two dyes used form two concentric rings around the center pin of the electrode. The PI is used for the measurement and the Calcein AM is used to provide contrast and a distinct edge to the ablation. The diameter of the ring up taking PI was measured by drawing a line across the image. As the size of the image is known to be 10.65 mm×10.65 mm, the length of the line can be expressed. Measurements were made for each image along the x-axis, y-axis, and two diagonal axes of the PI uptake region yielding four measurements (n=4) per image and done in triplicate (n=3). The resulting measurements were then used to test for significance. Pulse only treatments were compared to their respective combined PEI-NP and electric field treatment using a Student's t-test.

Description of Threshold Electric Field

As the electric field around the coaxial electrode changes spatially, the size of the ablation is an indication of the minimum or threshold electric field necessary to induce cell death. To quantify this value, a finite element model which describes the spatiotemporal electric field gradient can be used. Briefly, a finite element model which consists of a single well of a 12-well plate ($\sigma=1\times10^{-11}$ S/m) filled with cell culture media ($\sigma=1.54$ S/m) and the stainless steel coaxial electrode ($\sigma=4.03\times10^{6}$ S/m) was solved in COMSOL Multiphysics (COMSOL Inc., Palo Alto, CA). The fundamental equations of the solver were:

$$\nabla \cdot J = 0 \qquad \text{[Equation 7]}$$

$$J = \sigma E \qquad \text{[Equation 8]}$$

$$E = -\nabla V \qquad \text{[Equation 9]}$$

Figure 13:
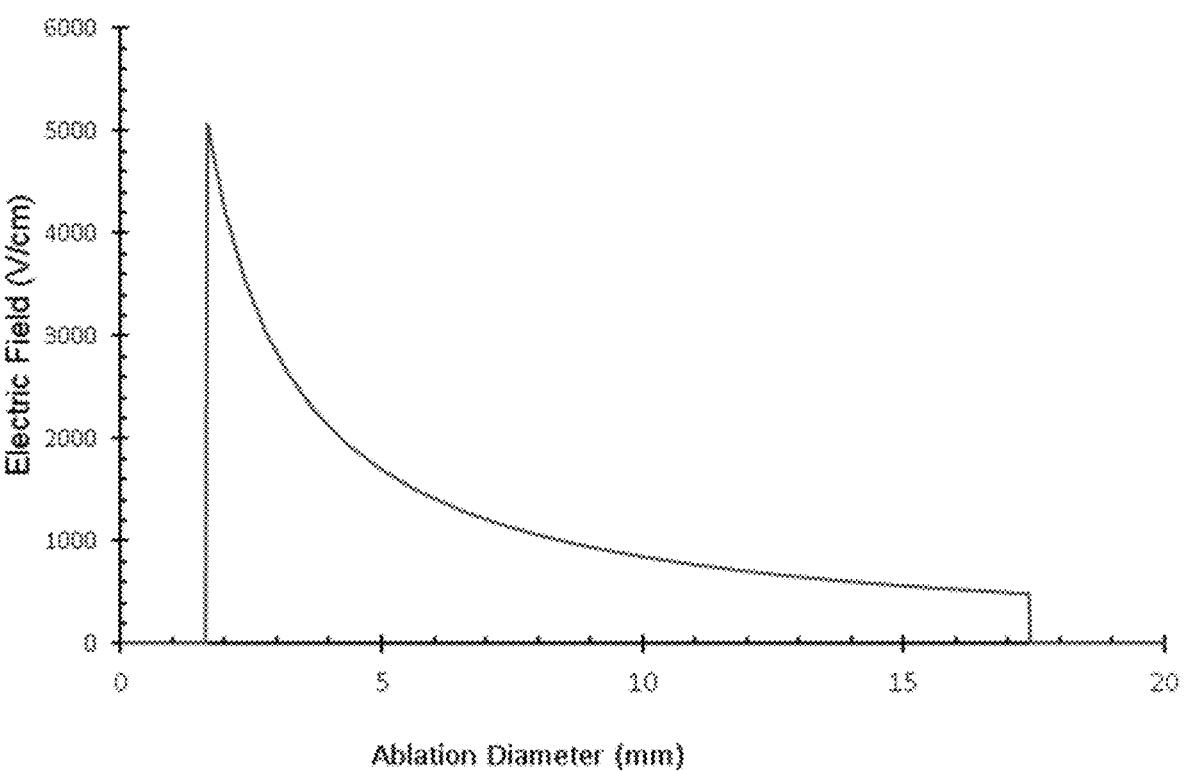
FIG. 13 is a graph illustrating electric field versus ablation diameter, according to some embodiments of the present invention.

The results of the model can be seen in FIG. 13. Diameters smaller than the center electrode and those outside the outer conductor experience little to no electric field. As illustrated in FIG. 13, regions below 1.64 mm are contained within the center conductor of the coaxial electrode and are not subjected to a high electric field. Within the treatment area (1.64-17.4 mm), there is an approximately exponential decay in the peak electric field. Beyond the outer conductor, the field returns to 0 V/cm. By substituting the measured ablation sizes into the model the threshold electric field was stated. Pulse only treatments were compared to their respective combined PEI-NP and pulse treatment using a t-test assuming unequal variance.

Results

High Concentrations of PEI-NPs Decrease the Cell Media Conductivity

Figure 14:
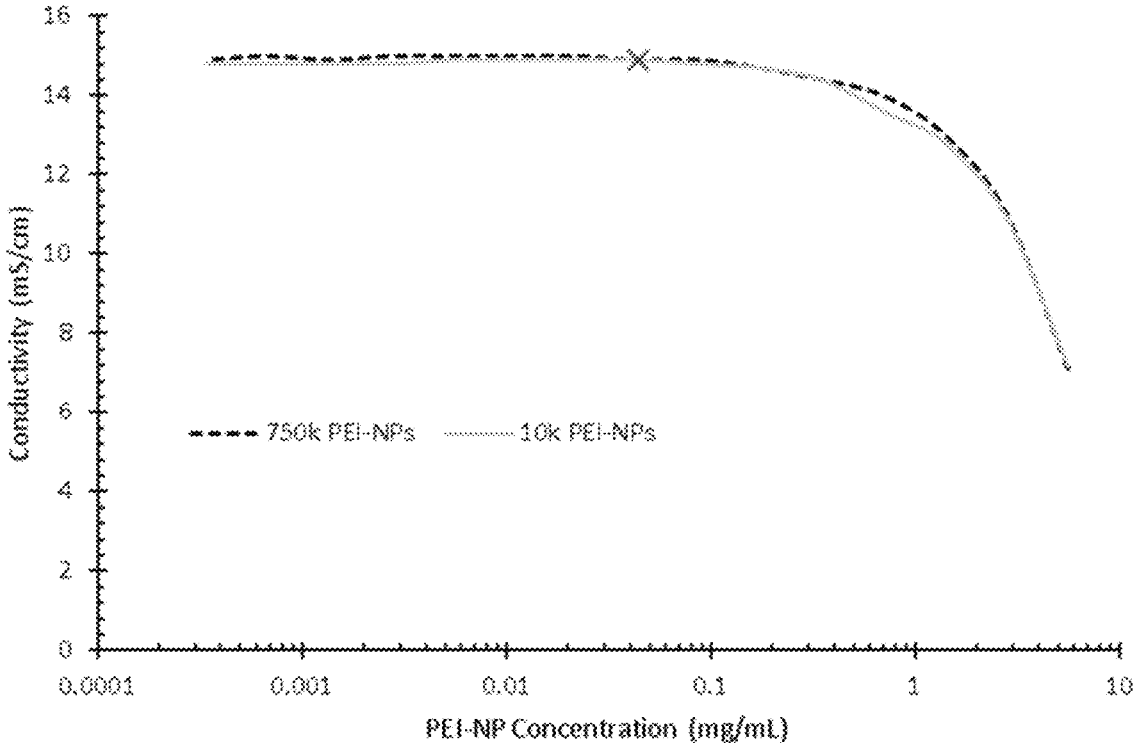
FIG. 14 is a graph illustrating conductivity as a function of PE-NP concentration, according to some embodiments of the present invention.

A conductivity test was done to determine the role of PEI-NPs on the bulk media's electrical properties. This is because adding charged particles could increase the conductivity thereby decreasing the load resistance and increasing the instantaneous power in each applied pulse. The results of the conductivity measurement indicate that this is not the case. FIG. 14 is a graph of conductivity as a function of PE-NP concentration, according to some embodiments of the present invention. As illustrated in FIG. 14, with increasing concentration of 10 k PEI-NP and 750 k PEI-NP, the conductivity decreased but only at high concentrations of PEI-NPs. As illustrated in FIG. 14, below a concentration of 0.3 mg/mL the conductivity of the solution is primarily driven by the cell culture media (14.9 mS/cm) and not the PEI-NPs. At higher concentrations, the PEI-NP's conductivity becomes more dominant in the solution and the conductivity decreases. The red line marker 'x' in FIG. 14 denotes the working concentration of PEI-NPs. At the working concentration of the PEI-NPs, there was no change in media conductivity with respect to the media without PEI-NPs at 14.9 mS/cm. Any change in cell death cannot be explained by changes in the media's conductivity and instead can be characterized by changes in the charging or discharging behavior of biological membranes due to the addition of the PEI-NPs.

Pulsed Electric Fields do not Influence NP Size or Zeta Potential

Retaining the integrity of the PEI-NPs after pulsed electric field treatment is critical to the development of a combined therapy. The LF Waveform, HF Waveform, and nsPEF pulses were delivered to the 10 k and 750 k PEI-NPs as described in Table 2. After subjecting the NPs to the pulse treatment, the size and zeta potential were measured, as illustrated in Table 3.

TABLE 3

| Nanoparticle Size and Zeta Potential With and Without Pulse Treatment | | | | |
|---|---|---|---|---|
| | 10k PEI-NP | | 750k PEI-NP | |
| Pulse Treatment | Size (nm) | Zeta Potential (mV) | Size (nm) | Zeta Potential (mV) |
| No Pulse | 514 ± 31 | 7.9 ± 0.8 | 101 ± 8 | 18.6 ± 1.4 |
| nsPEF | 500 ± 85 | 8.5 ± 0.8 | 90 ± 6 | 19.1 ± 1.4 |
| HF Waveform | 512 ± 38 | 7.9 ± 1.0 | 93 ± 4 | 18.7 ± ⅓ |
| LF Waveform | 401 ± 71 | 7.9 ± 0.5 | 99 ± 10 | 21.2 ± 1.2 |

Figure 15A:
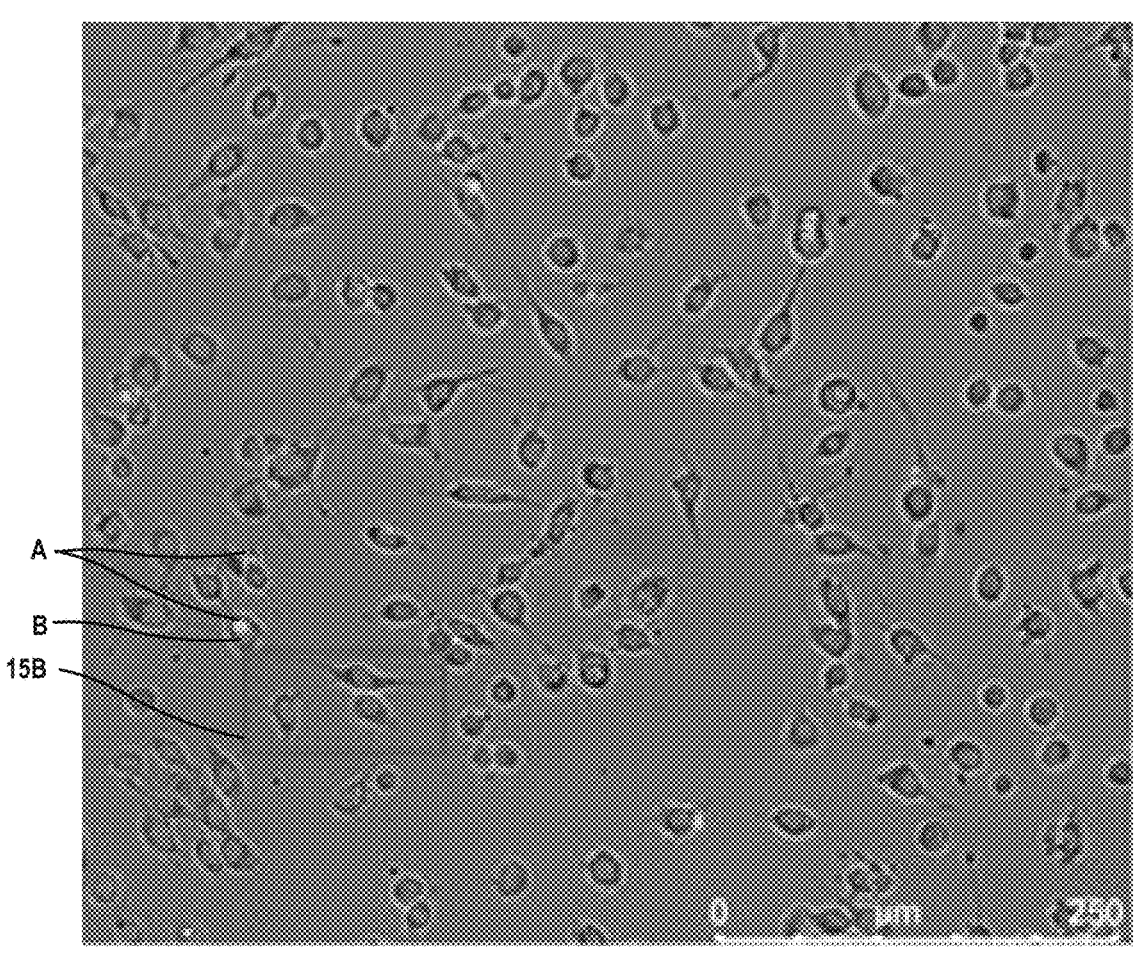
FIG. 15A is an image of cells exposed to PEI-NPs, according to some embodiments of the present invention.
Figure 15B:
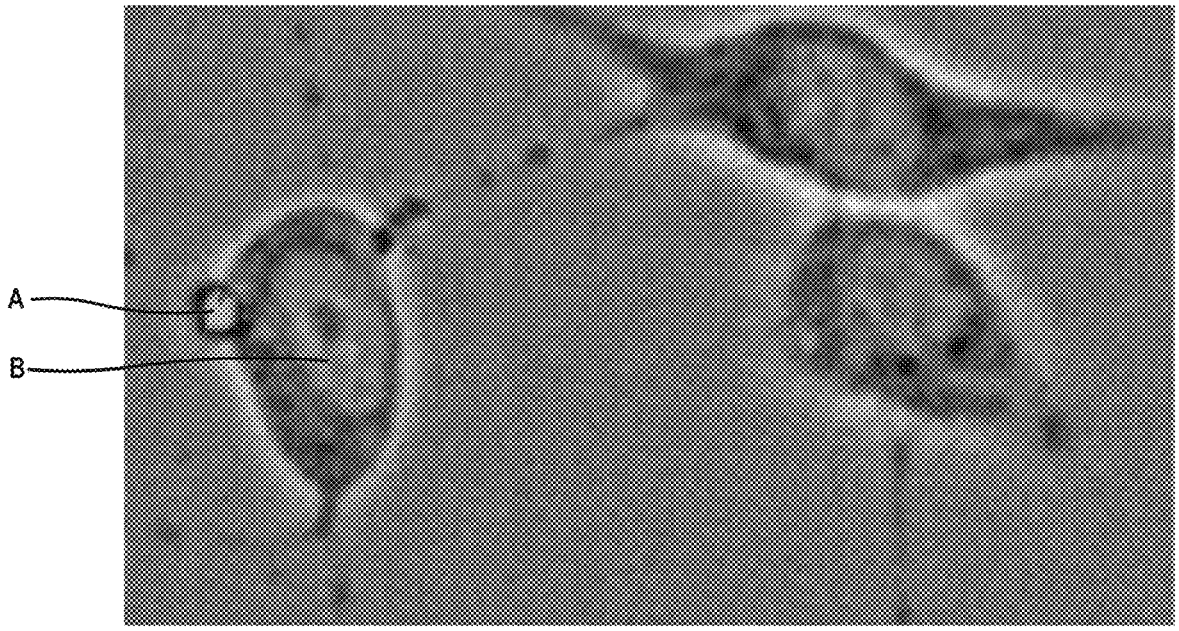
FIG. 15B is a magnified view of box '15B' of FIG. 15A.

The addition of the 10 k PEI-NPs to PBS prior to pulse treatment resulted in an increase in particle size from ~150 nm to ~500 nm. The presence of salt in the buffer solution resulted in charge screening between the anionic protein complex and cationic polymer which could be attributed to the increase in particle size and decrease in charge. The 750 k PEI-NPs did not exhibit a change in size or charge when suspended in PBS (see e.g., FIG. 9B). The particle size and zeta potential of the 10 k PEI-NPs was not affected by the pulse electric field treatment. Similarly, the size and zeta potential of the 750 k PEI-NPs treated with the three pulse electric fields remained equivalent to the untreated (No pulse) PEI-NPs. These results indicate that the PEI-NPs retain their functional properties following pulse electric field exposure. This demonstrates that pulsed electric fields from 100 µs to 400 ns can be used for enhancing cell death without compromising nanoparticle size or zeta potential. This additionally shows that enhancement of cell death is not due to chemical breakdown of the particles into toxic components, but rather that the nanoparticles are modifying the cells in such a way to enhance the lethality of the electric field PEI-NPs can Enter the Cell without an Electric Field By adding a fluorescent tag to the BSA, the location of the PEI-NP with respect to the cell can be identified which, in turn, could give insight into the particle-membrane interaction. When the fluorescent PEI-NPs were added without pulsed electric field, the PEI-NPs were able to enter the cell. See FIG. 6a for a representative image showing 10 k PEI-NP uptake. Of the 10 k PEI-NPs, 10.42% of cells showed uptake. In contrast, 27.56% of cells exposed to 750 k PEI-NPs had demonstrated uptake. The PEI-NPs were generally not co-located with the Hoechst stain, indicating the PEI-NPs are located outside the nucleus. Rather, the PEI-NPs are localized in pockets at or near the cell membrane. This could be indicative of uptake by endocytosis. For example, FIG. 15A is an image of cells exposed to PEI-NPs, according to some embodiments of the present invention. FIG. 15B is a magnified view of box '15B' of FIG. 15A. As illustrated in FIGS. 15A and 15B, PEI-NPs are able to enter selected cells in the absence of applied electric field. In FIG. 15A this is indicated by the presence of the 10 k PEI-NPs with FITC-BSA illustrated by reference designator 'A' and the cell nucleus illustrated by reference designator 'B'. FIG. 15B shows a cell containing PEI-NPs surrounded by those which show no evidence of uptake. Images were taken at 20×. From this experiment the PEI-NPs could be characterized as cell membrane impermeable, but able to enter the cell by an active transport mechanism.

PEI-NPs Enhance Cell Death Following Electric Field Exposure

The combination treatment of pulsed electric fields and PEI-NPs was described using fluorescence microscopy and image processing techniques. The ablation patterns are characteristic of the coaxial electrode configuration. The electric field is highest along the center conductor and decreases radially, forming a circular ablation pattern.

Figure 16:
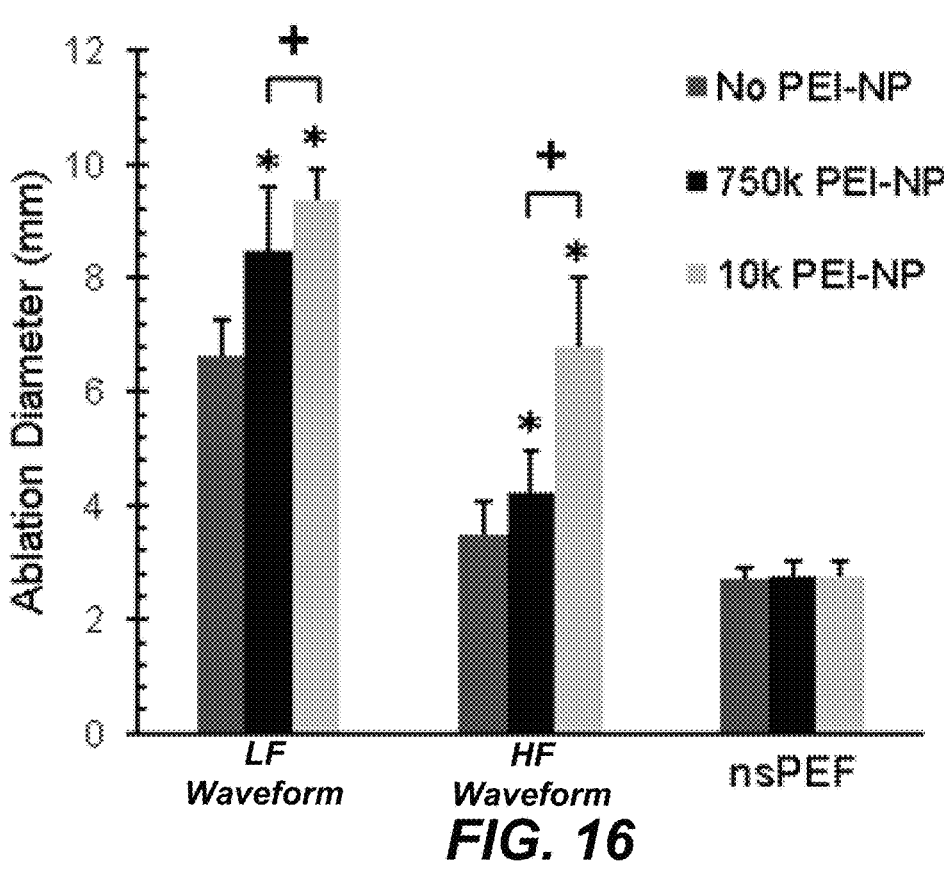
FIG. 16 is a graph that illustrates the ablation diameter for various pulse techniques as a function of PEI-NP configurations, according to some embodiments of the present invention.

The technique for quantifying cell death enhancement of PEI-NPs was measuring the diameter of the ablation region. For equivalent pulse delivery amount and rates, longer pulses had larger ablations. LF waveform had the largest ablation, followed by HF waveform and nsPEF. The addition of PEI-NPs was able to significantly increase the ablation diameter for both LF Waveform and HF Waveform pulses. FIG. 16 is a graph that illustrates the ablation diameter for various pulse techniques as a function of PEI-NP configurations, according to some embodiments of the present invention. As illustrated in FIG. 16, the addition of PEI-NPs enhances cell death when using either the LF waveform or HF waveform parameters. For both the LF waveform and HF waveform, 10 k PEI-NP were more effective then 750 k PEI-NP. Nanosecond duration pulses (nsPEF) do not experience an increase in ablation size. In FIG. 16, a '*' indicates a significant increase in ablation diameter with respect to the comparable No PEI-NPs at $\alpha=0.05$. In FIG. 16, the '+' indicates an increase in ablation diameter when testing different PEI-NPs at $\alpha=0.05$. Referring to FIG. 16, the percent increase in mean ablation diameter was 40.8% for 10 k PEI-NP and 27.0% for 750 k PEI-NP in LF waveform compared to cells treated without PEI-NPs. With the HF waveform, the increase in mean diameter was 94.9% for 10 k PEI-NP and 21.2% for 750 k PEI-NP with respect to the same pulse treatment without PEI-NPs. In both the LF waveform and HF waveform treatments, the smaller molecular weight PEI-NP resulted in a significantly greater ablation sizes. When comparing different pulse parameters, there was no statistical difference between the LF waveform without PEI-NP and the HF waveform with 10 k PEI-NP. All other tests showed differences. This indicates that the PEI-NPs are modifying the cells in such a way that enhances the cell membrane charging time sufficiently that certain waveforms, which without PEI-NPs would not be capable of inducing cell death, are now capable of inducing cell death.

Figure 17:
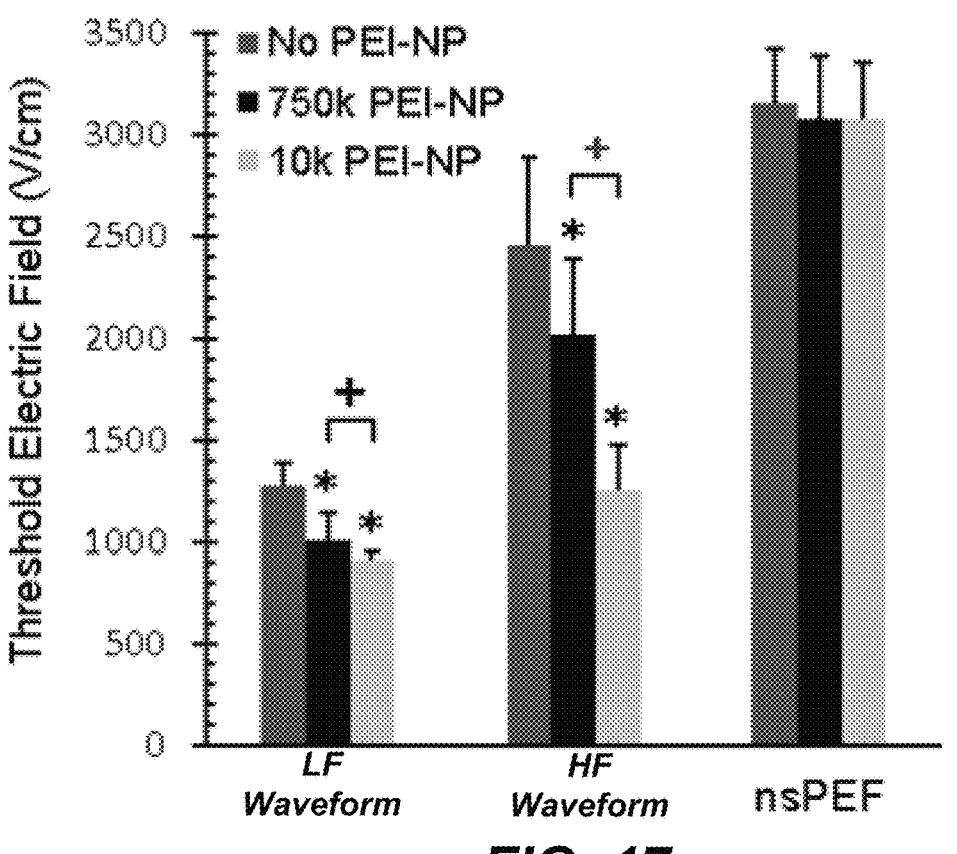
FIG. 17 is a graph that illustrates the threshold electric field for various pulse techniques as a function of PEI-NP configurations, according to some embodiments of the present invention.

The ablation diameters can also give insight into the electric field necessary to cause cell death. The minimal lethal threshold electric field can be seen in FIG. 17. FIG. 17 is a graph that illustrates the threshold electric field for various pulse techniques as a function of PEI-NP configurations, according to some embodiments of the present invention. As illustrated in FIG. 17, the threshold electric field for LF waveform and HF waveform pulses can be reduced by the addition of PEI-NPs. The threshold for nsPEF is not significantly reduced by PEI-NPs. In FIG. 17, the '*' indicates a significant drop in threshold electric field with respect to the comparable No PEI-NP at $\alpha=0.05$. In FIG. 17, the '+' indicates a significant decrease in threshold when testing different PEI-NPs at $\alpha=0.05$. The threshold field is largely determined by the pulse length with longer pulses having lower thresholds. Consequently, LF waveform pulses have the lowest threshold followed by HF waveform and nsPEF. The addition of PEI-NPs was able to reduce the threshold electric field in both LF waveform and HF waveform. LF waveform pulses had an average reduction of threshold electric field of 371 V/cm for 10 k PEI-NPs and a 269 V/cm for 750 k PEI-NPs. In the case of HF waveform there was an average reduction of 1193 V/cm and 429 V/cm for the 10 k PEI-NP and 750 k PEI-NP, respectively. The difference between 10 k and 750 k PEI-NP in LF waveform and HF waveform was statistically significant. Nanosecond duration pulses have the highest threshold and are not significantly reduced by the addition of PEI-NPs. The average decrease in threshold of nsPEF was 81 V/cm and 76 V/cm for 10 k PEI-NP and 750 k PEI-NP respectively. This indicates that there is an optimal characteristic combination of nanoparticles to modify cells and the treatment parameters which can be defined to treat a given tumor volume. Longer duration pulses in combination with PEI-NPs may require a lower voltage or a lower dose (IET or number of pulses) while shorter pulses may require a greater voltage or a higher dose to achieve the same ablation volume. This indicates that if pulse durations are changed dynamically within a given treatment to account for some measured or observed response (heating, muscle contractions, etc.) then the voltage or dose should be adjusted accordingly to achieve the originally intended treatment volume.

The embodiments described herein demonstrate that PEI-NPs can increase lethal ablation diameters and reduce the threshold electric field necessary to cause cell death. Of particular interest is that by using PEI-NPs, shorter HF waveform pulses can be as effective as LF waveform pulses without the addition of PEI-NPs. In the case of this experiment, HF waveform pulses in combination with PEI-NPs were equivalent in ablation size and threshold electric field to a normal LF waveform pulse. The in vivo benefits of using HF waveform over LF waveform, such as reduced muscle contraction and reduced requirement for cardiac synchronization could potentially be realized without having to sacrifice ablation size.

Both LF waveform and HF waveform demonstrated an increase in ablation diameter and a reduction in threshold after the addition of PEI-NPs. This was not the case for nsPEF which showed no significant increase in either ablation diameter or threshold with the addition of PEI-NPs. An explanation may be because as the pulse duration decreases into the nanosecond time domain, cell death is thought to occur by apoptosis which occurs on a much longer time scale than was measured in this study. There is the possibility that the combination of PEI-NPs and pulsed electric fields may influence apoptosis. Ultimately, these results do not conclude that a polymer NPs do not enhance nsPEF, rather that this combination of pulse conditions and PEI-NPs is ineffective at enhancing the effects observed within a few hours of treatment. It is also possible that polymer nanoparticles in combination with ultrashort pulses could be used to enhance other cellular responses (outside of cell death) such as increased metabolism or changes in gene expression.

By employing fluorescent PEI-NPs, it has been established that PEI-NPs can enter the cell without the application of a pulsed electric field. As discussed herein, 750 k PEI-NPs were more effective at entering the cell, but 10 k PEI-NPs were more effective at increasing ablation size. Based on this result it is doubtful that the amount of particle uptake is a driver for cell death. Rather, the type of particle uptake could be important. Once inside the cell the PEI-NP could interact in a variety of ways including: charging intracellular membranes, initiating cytoskeleton remodeling, or adding oxidative stress which may modify the charging or discharging behavior of biological membranes. Given the limited PEI-NP uptake and the observed increase in ablation size, it is a question whether a sufficient number of cells were able to uptake the PEI-NPs in order to account for the increase in the size of ablation. The PEI-NP uptake ultimately underscores the potential for drugs or other small molecules to be added to the PEI-NP for an additional combination treatment. For example PEI-NPs could be combined with plasmid DNA for gene delivery or bioactive proteins.

PEI-NP based membrane modification is thought to be a driver of cell death enhancement. Extracellular PEI-NPs are cationic and can contribute to membrane charging, interestingly without changing the media conductivity at the working concentration. Including charged domains adds electrochemical energy to the resting membrane, or Nernst, potential, reducing the electromagnetic energy required to induce a biological response. Beyond altering the transmembrane voltage, PEI-NPs could also interact with the membrane itself. First, the cationic PEI-NPs are electrostatically attracted to the membrane and could increase the osmotic pressure, induce membrane thinning, or imbed in the cell membrane creating nucleation sites for defects to form. The PEI-NP could also interact with charged membrane bound proteins. For example PEI enhances phosphatidylserine translocation across the cell membrane. Finally, the initiation of PEI-NP uptake could strain the membrane which, in turn, enhances susceptibility to damage by the electric field. Exploring these possibilities will be the foundation of future work.

There was a difference in ablation size and threshold with nanoparticle type. In the case of the embodiments described herein, the 10 k PEI-NP resulted in significantly larger ablations and lower threshold than the 750 k PEI-NP for both LF waveforms and HF waveforms. When examining other polymer nanoparticles used in combination with LF waveforms, the differences in nanoparticle makeup on ablation outcomes becomes stark. Cellulose nanocrystals demonstrated a reduction in threshold field of approximately 50

V/cm compared to 371 V/cm and 269 V/cm observed here for 10 k and 750 k PEI-NPs respectively. This is representative of an increase by a factor of 7.42 for 10 k PEI-NPs and 5.38 for 750 k PEI-NPs. This indicates that the presence of generic particles of a specific size is not sufficient for inducing the observed response, instead a series of engineering and chemistry choices must be made to specifically modify the cells in such a way that they become more susceptible to the influence of an external electric field.

Anti-Tumor Immune Response Against Spontaneous Tumors

Equine tumors can grow in locations that make surgical resection difficult or contraindicative, including tail and peri-anal regions, along with tumors forming near structures such as nerves and blood vessels. There are anatomical and procedural limitations which limit the utility of alternative interventions including Electro Chemo-Therapy (ECT), and cryo-ablation. According to embodiments if the present invention, it has been hypothesized that integrated time nanosecond pulse induced electrotherapy (INSPIRE) which delivers a series of 500-2000 nanosecond duration electrical pulses, and precisely controls tissue temperatures, could be safely and effectively administered to equine dermal tumors while greatly mitigating treatment induced muscle contractions associated with other electric field therapies. Patients with 3 or more discrete tumors measuring between 1-3 cm were recruited into a clinical trial. Electrical energy dosage (0.01 s and 0.02 s) and voltage (1000V and 2000V) parameters were evaluated in order to determine the effect of both variables on treatment outcomes. Tumors treated at 2,000 Volts and receiving an electrical energy dosage of 0.02 seconds, the sum of all electrical pulses delivered, reduced in size by 90% on average (N=14) with complete responses in 11 of the 14 tumors. Across all patients, a 49.9% reduction was observed in the volume of untreated, but measured, control tumors that were nearby the treated tumors.

Electrical therapy as described herein is a safe and effective treatment for 1-3 cm tumors that can be readily implemented without structural changes to standard clinical practices. Equine patients were successfully treated while awake and standing with only mild sedation and local anesthetic, which is an improvement over other pulsed electric field therapies which require patients to be fully sedated due to the induction of intense muscle contractions.

The embodiments of the present invention (e.g., INSPIRE) utilize nanosecond duration pulsed electric fields to treat tumors in situ. The electrical waveforms are designed to modify the charging time of cell membranes by controlling tissue temperatures, induce cell death within a prescribed volume, mitigate muscle contractions associated with electric field treatments, enable administering the treatments with only local anesthetic in standing patients, and to facilitate an immune response against metastatic tumors. With electrical treatment applicators according to embodiments described herein, the depth of the ablation and treated area can be controlled by the insertion distance of the electrode needle.

Based on encouraging in vitro and ex vivo data, it was hypothesized that electrical therapy according to embodiments of the present invention (e.g., INSPIRE) was a safe and effective treatment against cutaneous tumors between 1 and 4 cm in size and could induce a positive immune response against nearby, but untreated tumors. The objective of the study was to evaluate the long term biological response following treatments according to embodiments described herein as well as to assess if the treatment was capable of reducing tumor burden and producing a durable anti-tumor response. A custom ring-and-pin electrode was designed to interface with new hardware designed to measured and control tissue temperatures while administering 500 ns or 2000 ns treatments Equine patients presenting 3 or more cutaneous melanoma tumors sized 1-4 cm were recruited into an approved clinical trial. Following measurement of 'treatment' and 'control' tumors, the treatment applicator was adjusted such that the needle electrode reached the distal margin of the tumor. Treatment parameters consisting of electrical energy dosage (integrated time, calculated as the sum of electrical pulses delivered) and electrical voltage were adjusted in order to evaluate the effects of these variables on treatment outcomes. Two pulsed waveforms were used, consisting of a paired (bi-polar) pulse of width 500 or 2000 nanoseconds. Computer modeling was used to determine the expected ablation zone when a specific voltage was applied to the treatment applicator.

Figure 18:
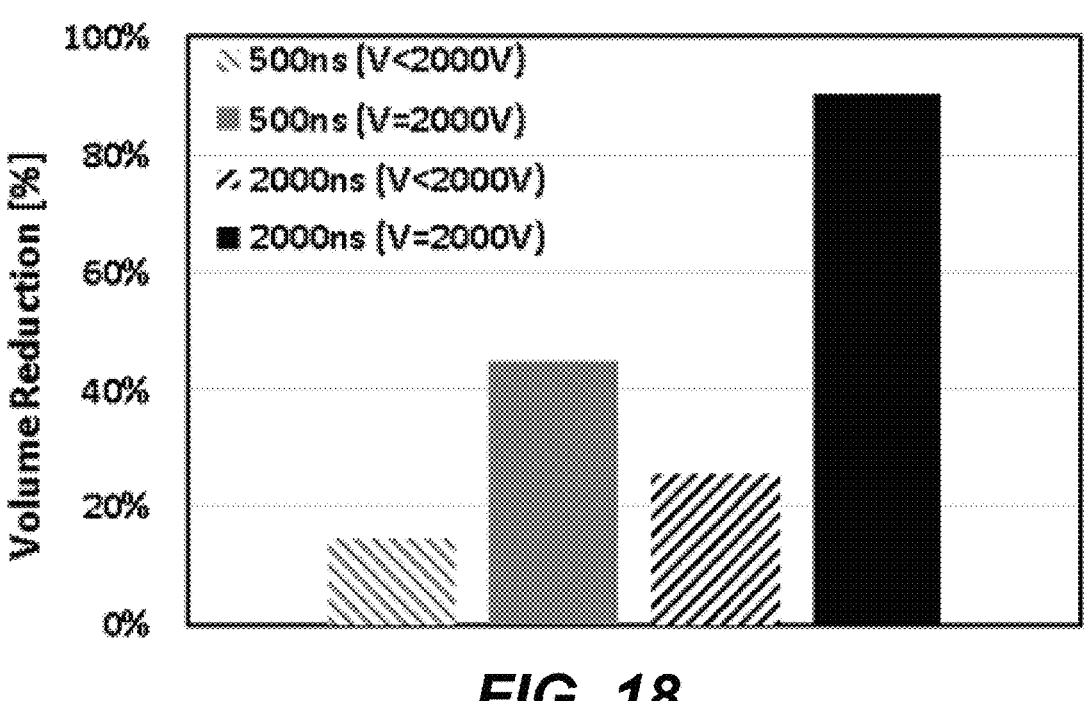
FIG. 18 is a graph illustrating observed reduction of tumor volume following treatment of equine melanoma as a function of waveform pulse width and voltage, according to some embodiments of the present invention.
Figure 19:
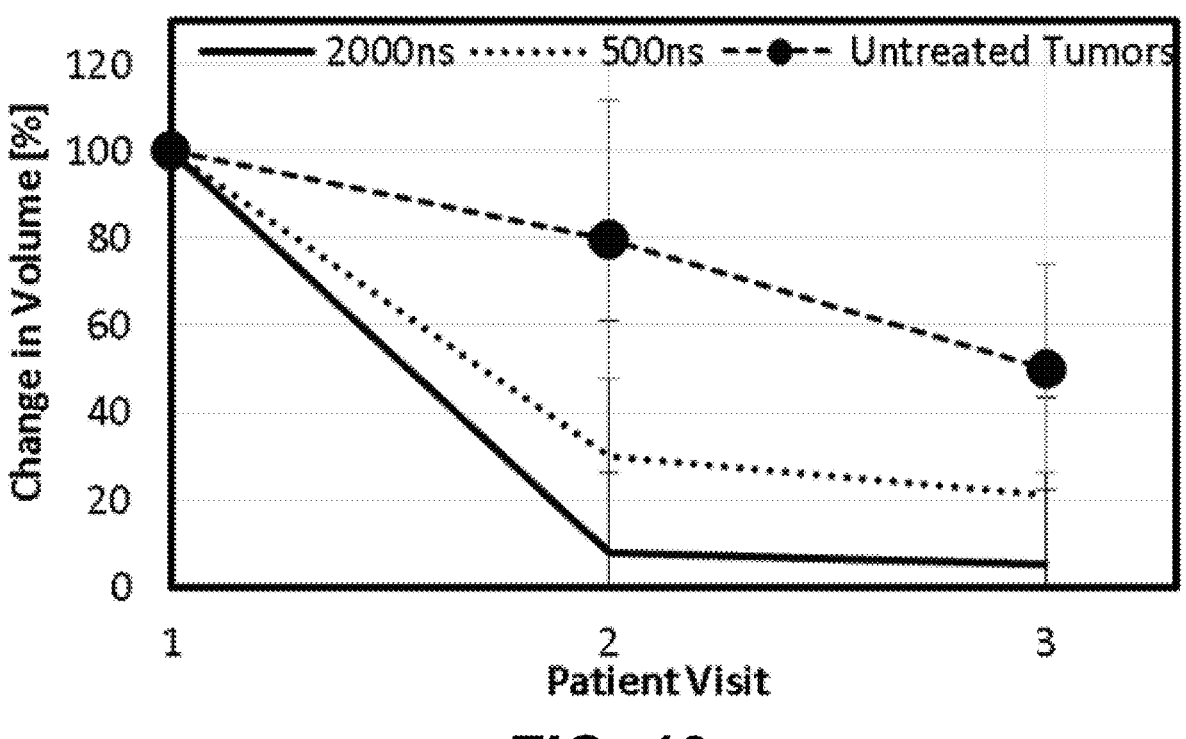
FIG. 19 is a graph illustrating observed reduction of tumor volume following treatment of equine melanoma as a function of time from initial treatment, according to some embodiments of the present invention.

FIG. 18 is a graph illustrating observed reduction of tumor volume following treatment of equine melanoma as a function of waveform pulse width and voltage, according to some embodiments of the present invention. FIG. 19 is a graph illustrating observed reduction of tumor volume following treatment of equine melanoma as a function of time from initial treatment, according to some embodiments of the present invention. With respect to the data of FIG. 19, the clinical visits were spaced approximately 3-5 weeks apart.

For tumors treated at 2,000V and 0.02 seconds of electrical energy dosage with 2000 ns waveforms, 78% of tumors (11 of 14) experienced a complete response with no visible tumor tissue upon follow up. For tumors treated at 2,000V with 0.02 seconds of electrical energy with 500 ns waveforms, 20% of tumors (1 of 5) exhibited a complete response on follow up. Treatments that consisted of a reduced electrical voltage between 1,000V and 1,500V resulted in 10% (1 of 10) of tumors exhibiting a complete response for 2000 ns waveforms and no complete responses for the 500 ns waveforms. Across all patients a 49.9% reduction was observed in the volume of untreated, but measured, control tumors which were nearby the treated tumors.

All patients were able to be treated while standing, even at treatment voltages of 2,000V. Treatment times were between 15 and 100 minutes, depending on the number and size of tumors to be treated. Mild sedation and local anesthesia were used in some cases. Electrical therapy parameters according to embodiments described herein reached 2,000V with appropriate treatment dosage using a 2000 ns waveform was effective at inducing a durable anti-tumor response with a significant reduction in tumor volume across all patients while allowing for patients to be treated while awake and standing. Embodiments of the present invention provide the ability to ease clinical practice by reducing muscle contractions along with the ability to eliminate and/or reduce tumors close to critical structures, which has several clinical benefits. Due to sedation not being needed, patients can undergo treatment for longer durations, which enables multiple and larger tumors to be treated. An effective integrated time of 0.02 seconds confirmed in this study can be used as a baseline for treating tumors moving forward. Additional patients were treated outside of the clinical trial as part of routine clinical practice. Some patients presented with tumors near sensitive innervated structures which were challenging to block with local anesthetic (e.g., in proximity to the eye). In some instances the patient was aware of and reacted to treatments with 2000 ns waveforms. In these cases, the pulse durations were sequentially decreased to 1000 ns, 750 ns, and 500 ns until the patient was tolerant of the treatment. When the prescribed dose was held constant these locations had notably smaller treatment zones observed upon follow up indicating that decreases in pulse width should be accompanied by a corresponding increase in treatment voltage, treatment dose, or a combination of increased voltage and dose In Vitro INSPIRE Treatments and Computer Models Pulsed electric fields (PEFs) such as those described herein with respect to the present invention induce a transient increase in electrical potentials across cell and organelle membranes. The magnitude of this transient is dependent on a number of parameters including the electrical properties of the cell and its environment, the magnitude of the local electric field, and the time domain characteristics of the pulses. Similarly, the biological responses following PEF exposure are dependent on a complex combination of stochastic energy dependent phenomena. These range in severity and include the absence of a measurable response, disruption of mitotic spindle formation, temporary permeabilization of the cell membrane, induction of apoptosis, and outright membrane disruption leading to a necrotic form of cell death.

Embodiments of the present invention provide pulse electric therapy including feedback to adjust the pulses, such as integrated time nanosecond pulse irreversible electroporation (INSPIRE), in which the stochastic nature of PEF responses is exploited by delivering significantly larger electrical doses (integrated times) than common with NK-IRE. The results show that while NK-IRE ablation sizes appear to reach a steady state, ablations performed according to embodiments described herein increase sequentially with integrated times of 0.001, 0.01, and 0.1 s. As discussed herein, computational models were used to investigate the charging/discharging behavior of cell membranes during exposure to treatments according to the present invention and to determine the treatment voltages and overall treatment durations that would be used for the pulsed treatment to achieve equivalent ablation sizes as other methods, such as NK-IRE, clinically. For experiments conducted at physiological temperatures, 0.01 s IET pulse treatments with 350 ns, 500 ns, and 750 ns pulses utilize electric field intensities of 1109V/cm, 954 V/cm, and 698V/cm, respectively, to induce cell death. To achieve similar ablation volumes as comparable methods (e.g., NK-IRE) these protocols would require the use of 6.7 kV, 5.8 kV, and 4.2 kV pulses, respectively. To inhibit significant thermal injury adjacent to the electrode, 44° C. temperature controlled treatments were simulated and required 1190 s, 870 s, and 450 s, respectively, to achieve identical ablation volumes to standard 100 s 3 kV NK-IRE protocols.

Embodiments of the present invention provide pulse electric therapy including feedback to adjust the pulses, such as integrated time nanosecond pulse induced electrotherapy (INSPIRE) which takes into account the specific electrical dose needed for discrete pulse durations to induce cell death and modifies the treatment parameters in response to real time biological measurements. The results show that while ablation sizes due to existing techniques appear to reach a steady state, ablations performed according to embodiments described herein increase sequentially with integrated times of 0.001, 0.01, and 0.1 s, therefore a prescribed dose can be used to define the volume of the tissue treated Ablations performed according to the embodiments described herein increase sequentially with pulse widths of 350 ns, 500 ns, 750 ns, 1000 ns, and 2000 ns, therefore a prescribed pulse with can be used to define the volume of the tissue treated.

As discussed herein, certain longer pulse widths and smaller doses resulted in ablations which were equivalent to treatments with shorter pulses and greater doses, therefore algorithms which reduce pulse widths can increase the prescribed dose to maintain an equivalent outcome. Similarly, algorithms which increase pulse widths can decrease the prescribed dose to maintain an equivalent outcome. As discussed herein, computational models were used to determine the treatment voltages and overall treatment durations that would be used for the pulsed treatment to achieve equivalent ablation sizes as other methods, such as NK-IRE, clinically. For experiments conducted at physiological temperatures, 0.01 s IET pulse treatments with 350 ns, 500 ns, and 750 ns pulses utilize electric field intensities of 1109V/cm, 954 V/cm, and 698V/cm, respectively, to induce cell death. To achieve similar ablation volumes as comparable methods (e.g., NK-IRE) these protocols would require the use of 6.7 kV, 5.8 kV, and 4.2 kV pulses, respectively. To inhibit significant thermal injury adjacent to the electrode, 44° C. temperature controlled treatments were simulated and required 1190 s, 870 s, and 450 s, respectively, to achieve identical ablation volumes to standard 100 s 3 kV NK-IRE protocols.

Cell Culture and 3D Tumor Model

Due to interest in utilizing PEFs for the treatment of brain tumors where thermal transients can be especially deleterious, U118 human glioblastoma cells were utilized in this study. The cells were cultured in DMEM supplemented with penicillin/streptomycin and 10% fetal bovine serum. Upon reaching approximately 80% confluence the cells were harvested from 2D culture via trypsinization. After deactivating the trypsin with fresh media, the cells were centrifuged, and resuspended in media at a concentration of $1\times10^6$ cells/mL. 3D tumor constructs were created by mixing the cell suspension in a one-to-one ratio with PureCol Ez on ice to achieve a 2.5 mg/mL concentration of collagen and a final cell concentration of $0.5\times10^6$ cells/mL. This mixture was then rapidly aloquatted into 12-well plates on ice with 0.5 mL/well. A carful swirling motion was used with a 500 μL pipette to achieve complete coverage of the well surface. The well plate was then incubated overnight at 37° C. in a 5% $CO_2$ atmosphere to allow the matrix to solidify. 500 μL of fresh media was then added to each well to provide hydration and nutrients prior to experiments.

Pulse Delivery

Figure 20:
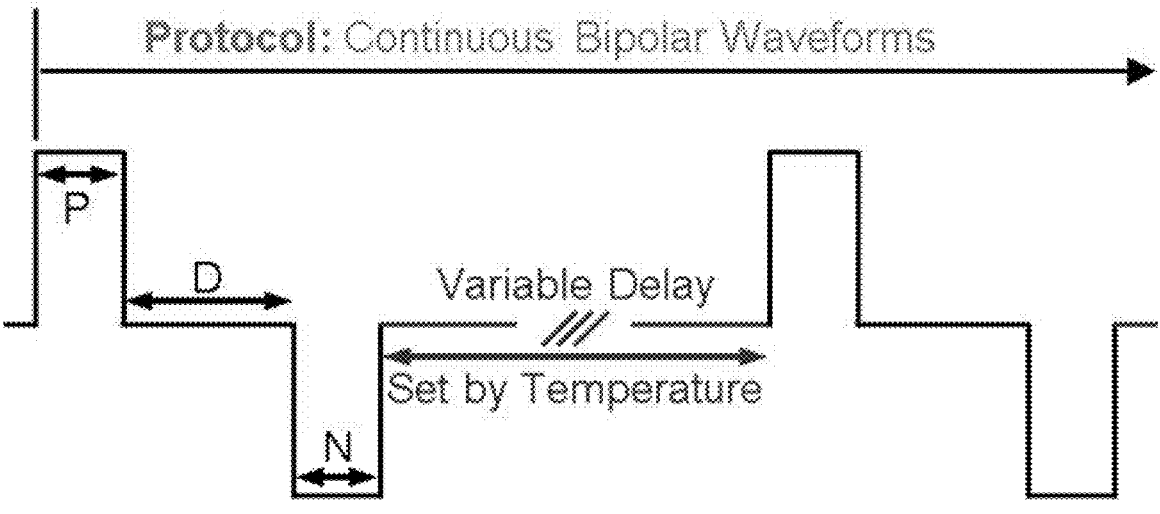
FIG. 20 is a graph illustrating electric pulse waveforms, according to embodiments of the present invention.
Figure 21:
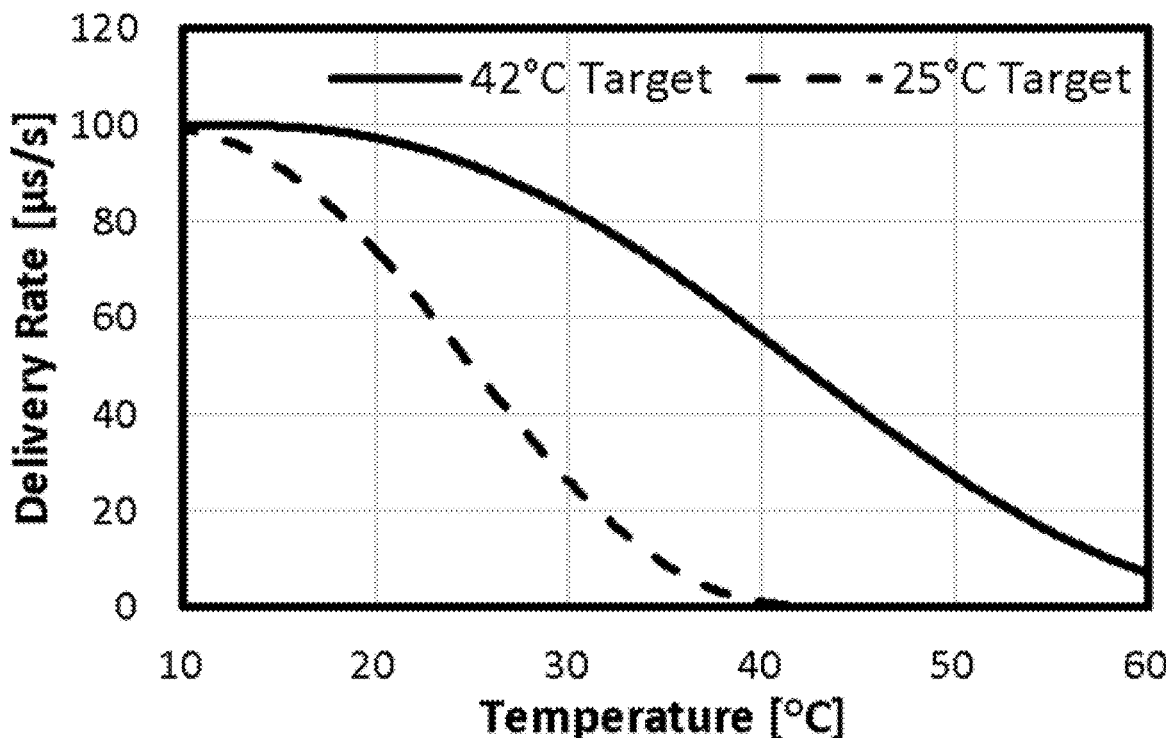
FIG. 21 is a graph illustrating a delivery rate based on the instantaneous temperature, according to embodiments of the present invention.

FIG. 20 is a graph illustrating electric pulse waveforms, according to embodiments of the present invention. Referring to FIG. 20, electric treatments according to embodiments described herein, include waveforms that of a positive pulse (P), a brief delay (D) (e.g., equal to 1 μs), and a negative pulse (N). This alternating polarity waveform is designed to mitigate muscle contractions in vivo. According to embodiments of the present invention, the delay between successive waveforms may be controlled algorithmically based on temperature readings. Because pulse widths vary between treatment groups the algorithm may calculate a target energy delivery rate based on the instantaneous temperature which is measured at the center of the ring and pin electrode (such as that illustrated in FIGS. 5B and 5C) via a temperature sensor (such as temperature sensor 540 illustrated in FIG. 5A) placed within the center pin electrode. For example, FIG. 21 is a graph illustrating a delivery rate based on the instantaneous temperature, according to embodiments of the present invention.

In some experiments, the waveform was symmetric, meaning that the positive and negative pulses had the same duration of 350, 500, 750, 1000, or 2000 ns. However, the present invention is not limited thereto. The minimum pulse width corresponded to the minimum pulse with achievable with the custom H-Bridge pulse generator utilized in this study, but shorter pulses could be utilized. The delay between successive waveforms was algorithmically controlled such that transient temperature increases of 5° C. were achieved and maintained. As treatments had different pulse widths, the algorithm calculated a target mean energy delivery rate (μs/s, FIG. 1b) which was then converted into a waveform delay based on the experimental pulse width being evaluated. Voltage and current waveforms were recorded in real time via a custom 100 MSPS data acquisition system. To enable comparison between treatments with different pulse widths, treatment doses were defined as a specified integrated energized time (IET) calculated as indicated in Equation 4 described herein.

A baseline dose of 0.01 s was defined based on NK-IRE treatments which deliver 100×100 μs electrical pulses. Two additional doses representing 0.1× (0.001 s) and 10× (0.1 s) the baseline dose were investigated. All treatments had an initial energy deliver rate of 100 μs/s which similarly decreased based on the temperature control algorithm.

Figures 22A, 22B, 22C:
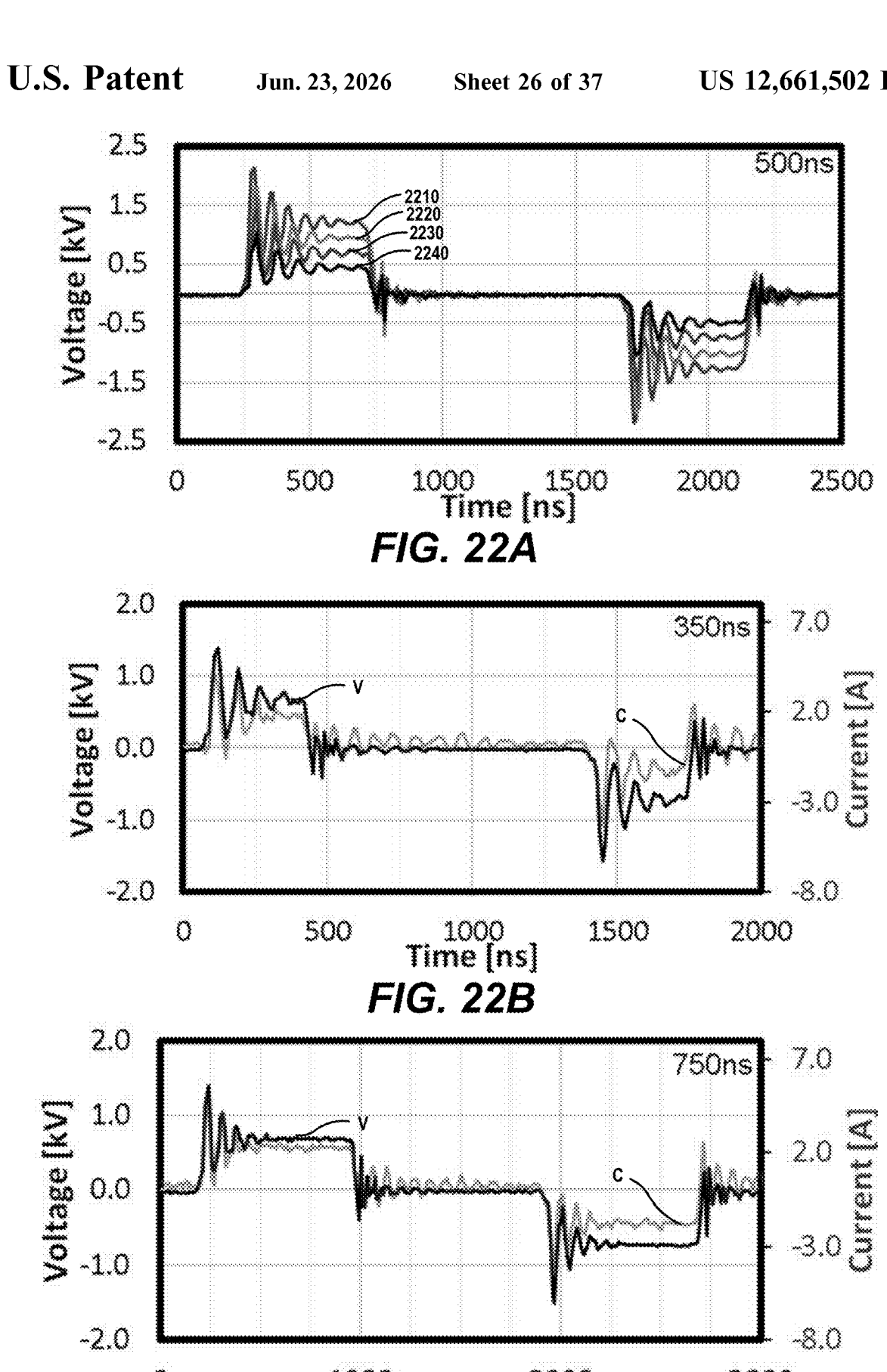
FIGS. 22A-22E are graphs illustrating representative waveforms according to embodiments of the present invention.
Figure 22D:
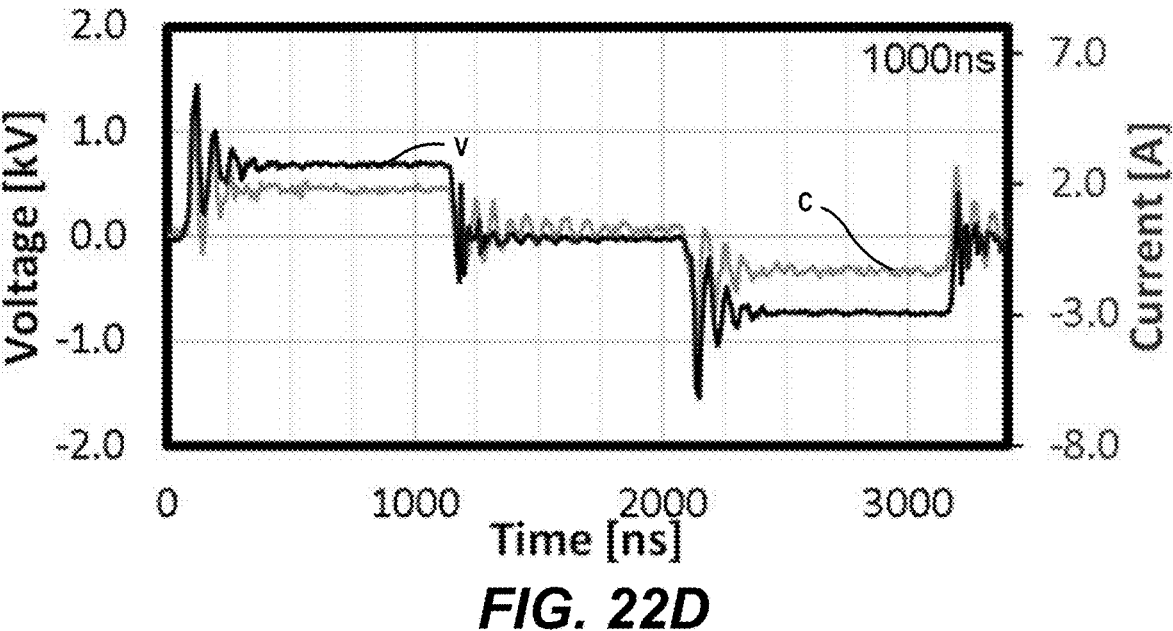
Figure 22E:
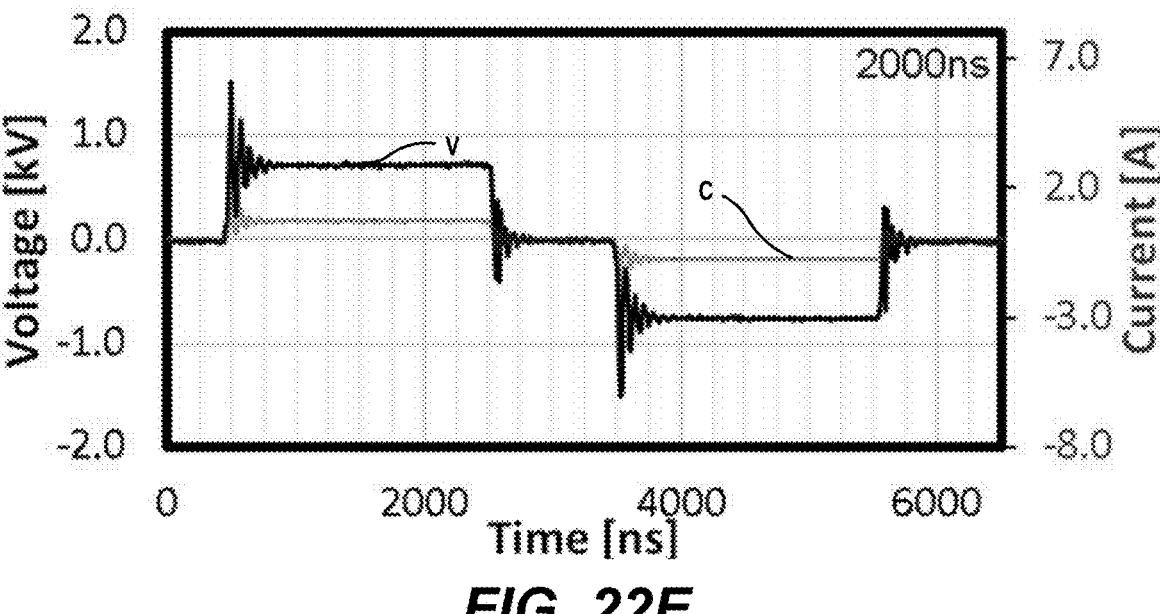

All experiments were conducted by placing well plates containing the 3D tumor models on top of a custom machined aluminum block with a thin layer of ethanol between the block and well plate to aid in thermal transport. The aluminum block was placed on the heating/cooling surface of a Peltier thermoelectric heater and the samples were allowed to normalize to the treatment temperature (20° C. or 37° C.) prior to the initiation of treatments. All treatments were administered through a custom coaxial electrode consisting of a 17 mm outer ring and a 1 mm hollow center pin held in place by a laser cut acrylic holder (e.g., FIGS. 5B and 5C). A 200 μm diameter fiber optic temperature sensor 540 was placed through the center pin into the center of the 3D tumor (e.g. FIG. 5A) where thermal transients were assumed to be at an approximate maximum. Temperature data was recorded at 3 Hz and utilized by a temperature control algorithm built into the pulse delivery system to achieve and maintain a 5° C. temperature transient throughout the treatments. Transient voltage and current measurements for each treatment were acquired via a custom 100MSPS data acquisition system integrated into the pulse generator. FIGS. 22A-22E are graphs illustrating representative waveforms according to embodiments of the present invention. FIG. 22A is a graph illustrating 500 ns electric pulse treatments according to the present invention, with pulse voltages of 500V (reference designator 2240), 750V (reference designator 2230), 1000V (reference designator 2220), and 1250V (reference designator 2210). FIGS. 22B-22D are graphs illustrating representative voltage and current waveforms for 750V treatments according to embodiments of the present invention with pulse durations of 350 ns (FIG. 22B), 750 ns (FIG. 22C), 1000 ns (FIG. 22D), and 2000 ns (FIG. 22E). In FIGS. 22B-22D the voltage waveform is labelled with 'V' and the current waveform is labelled with 'C'.

To determine appropriate voltage settings to produce visible treatment zones across a wide pulse-duration space an initial voltage escalation study was conducted using 500 ns pulses, a dose of 0.01 s, and voltages of 500, 750, 1000, and 1250V. A voltage of 750V was found to provide the greatest dynamic range for these pulse widths (350-2000 ns) and utilized in subsequent experiments.

To characterize the pulse duration space, a series of experiments were conducted at 750V with a dose of 0.01 s and pulse widths of 350, 500, 750, 1000, and 2000 ns at room temperature. A subset of these were repeated with a baseline temperature 37° C. (350, 500, and 750 ns) and target temperature of 42° C. to evaluate if the lethal effects of these pulses was dependent on temperature. Finally, to determine the effect of integrated time on treatment outcomes a subset of treatments were repeated for IET of 0.001, 0.01, and 0.1 s (500 and 2000 ns pulses).

Treatment parameters were evaluated in a minimum of three (N=3) times. In some cases, individual parameters needed to be investigated on different experimental days, in these cases a minimum of two replicates was conducted per day resulting in some parameters with more than three replicates. A full accounting of the number of replicates is provided in the supplemental tables associated with each treatment group. Statistical analysis was conducted via a one sided Student's T-test with a significance level of 0.05 ($\alpha$=0.05) using JMP (14.1.0 Pro, SAS Institute Inc. Cary, NC).

Figure 23A:
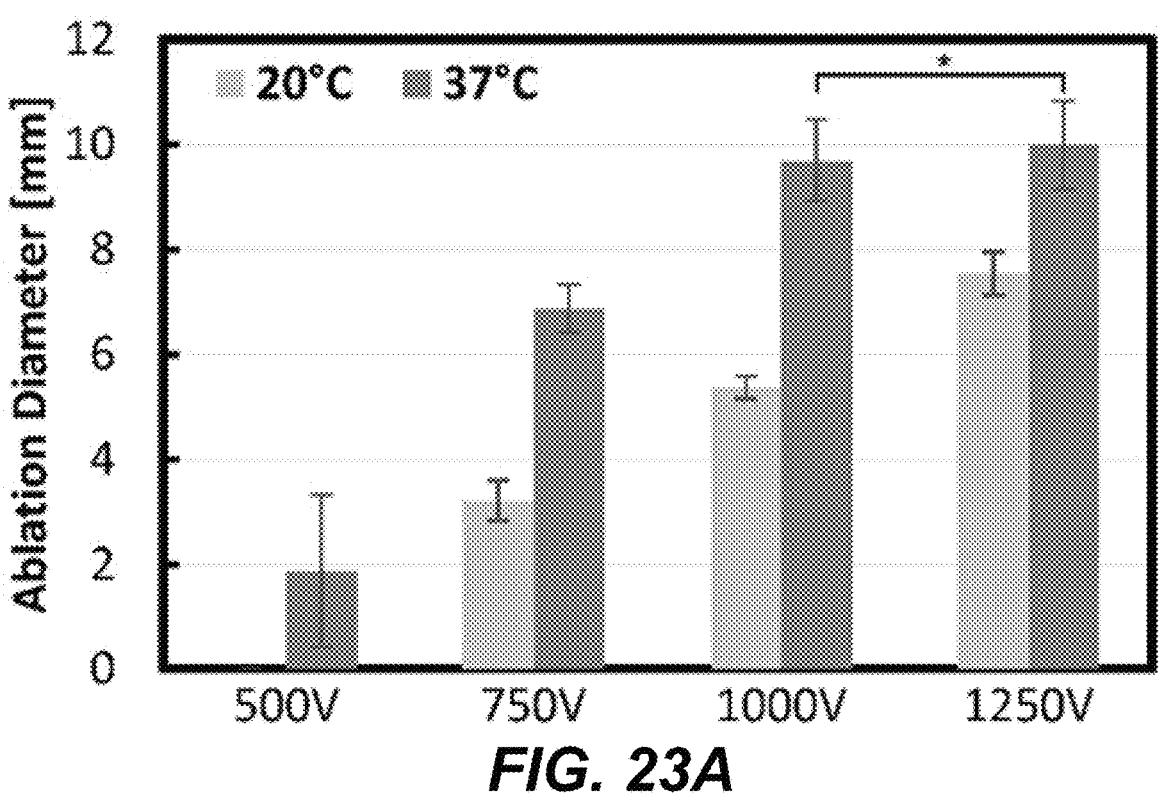
FIGS. 23A-23C are graphs illustrating experimental results provided by embodiments of the present invention as a function of applied voltage and temperature.
Figure 23B:
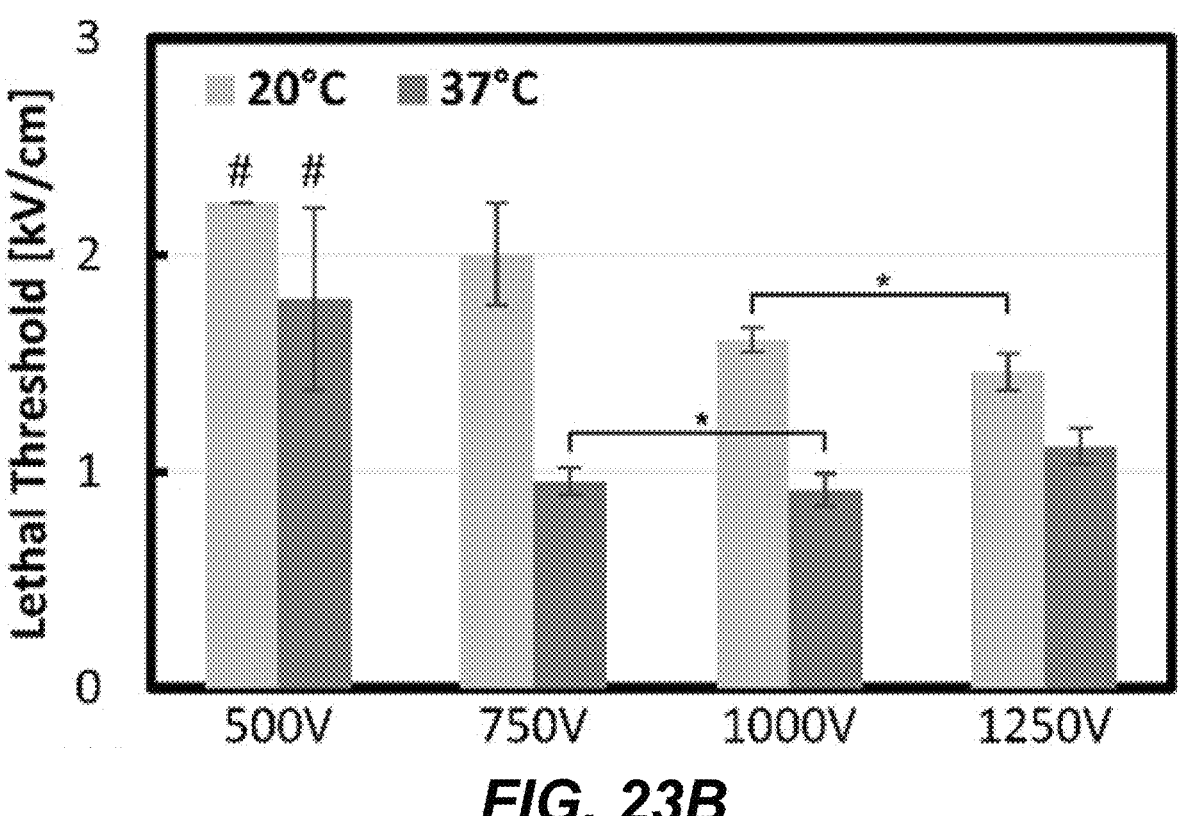
Figure 23C:
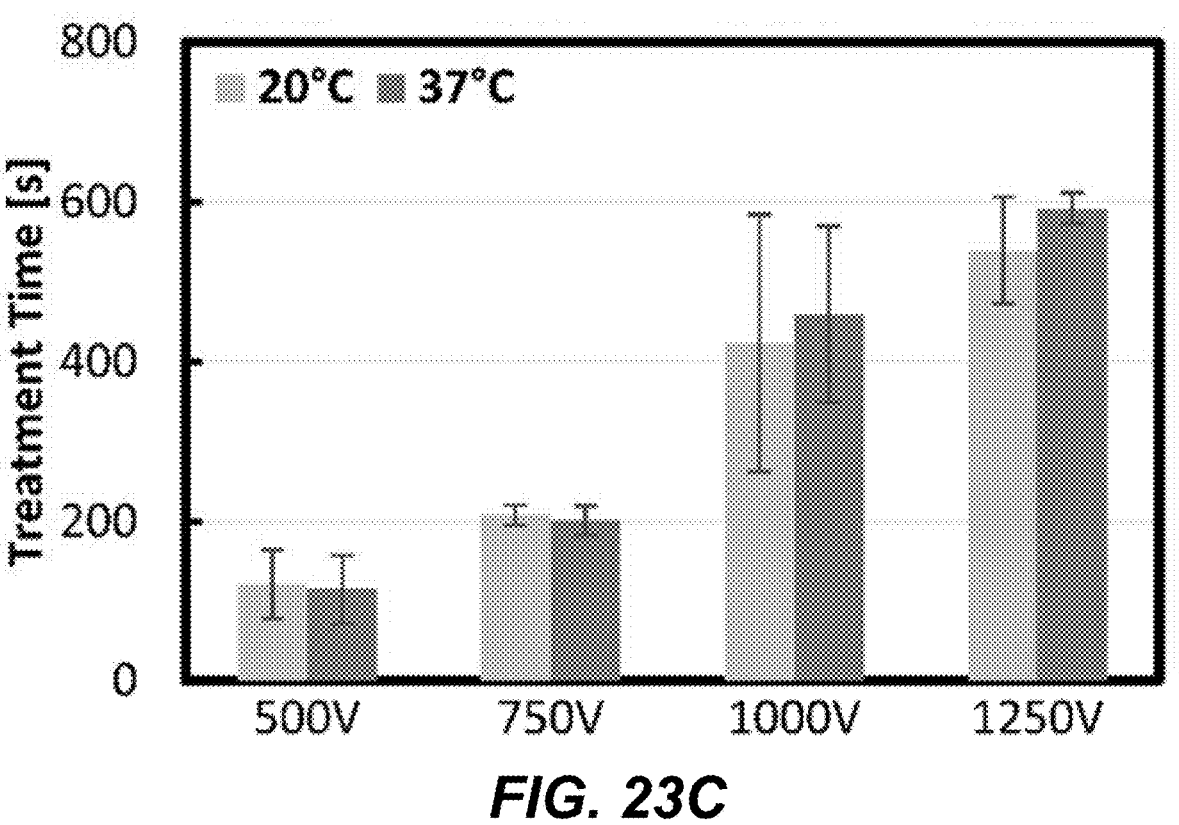

FIGS. 23A-23C are graphs illustrating experimental results provided by embodiments of the present invention as a function of applied voltage and temperature. FIGS. 23A-23C illustrate ablation diameters (FIG. 23A), lethal thresholds (FIG. 23B), treatment times (FIG. 23C) for 0.01 s IET 500 ns treatments with 500V, 750V, 1000V, and 1250V with initial temperatures of 20° C. and 37° C. In the figures, a '#' indicates treatments with non-measureable ablation diameters with electric field thresholds presumed to be 2.24 kV/cm, and a '*' indicates groups which were not statistically significantly different (p>0.05).

Computational Modeling

To elucidate potential mechanisms for the observed experimental results, finite element computational models were constructed to evaluate (a) what electric field isocontours corresponded with the diameter of each treatment administered (the lethal threshold), (b) to evaluate the relative transmembrane potential increase induced in cells at the margin of each treatment zone, and (c) to determine approximate voltages necessary for protocols according to the present invention to achieve similar ablation volumes as NK-IRE in a clinical setting. Briefly, the electric field distribution within the 3D tumor models, around a single cell, and surrounding a clinical applicator were calculated using separate 2D axisymmetric finite element models in COMSOL Multiphysics (V5.5, COMSOL Inc., Los Altos, CA) via established techniques. The Electric Currents, Heat Transfer in Solids, and Electromagnetic Heating modules were used to calculate the electric field distributions taking the temperature dependent electrical conductivity of tissues and cell culture media into account. These figures utilized adaptive meshing techniques to ensure convergence of solutions in regions where high electric field gradients were observed.

Computational Determination of Lethal Thresholds

Figure 24A:
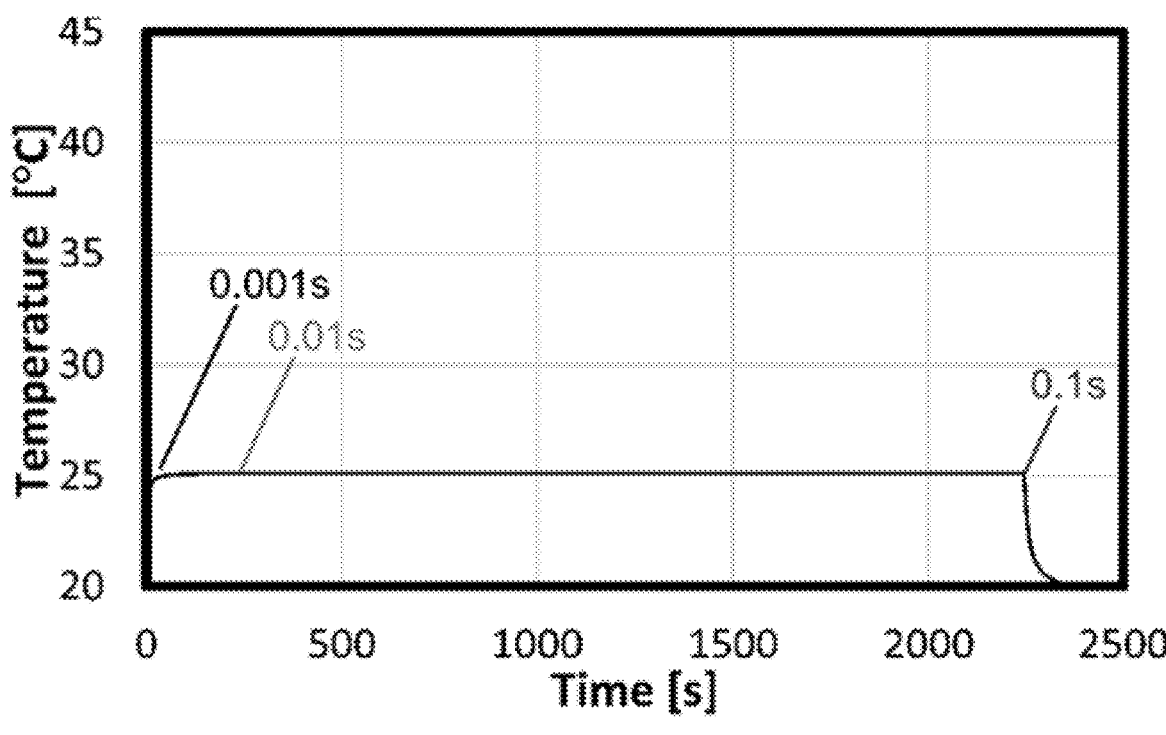
FIGS. 24A-24D are waveforms that illustrate simulated responses for IET doses of 0.001 s, 0.01 s, and 0.1 s, according to embodiments of the present invention.
Figures 24B, 24C, 24D:
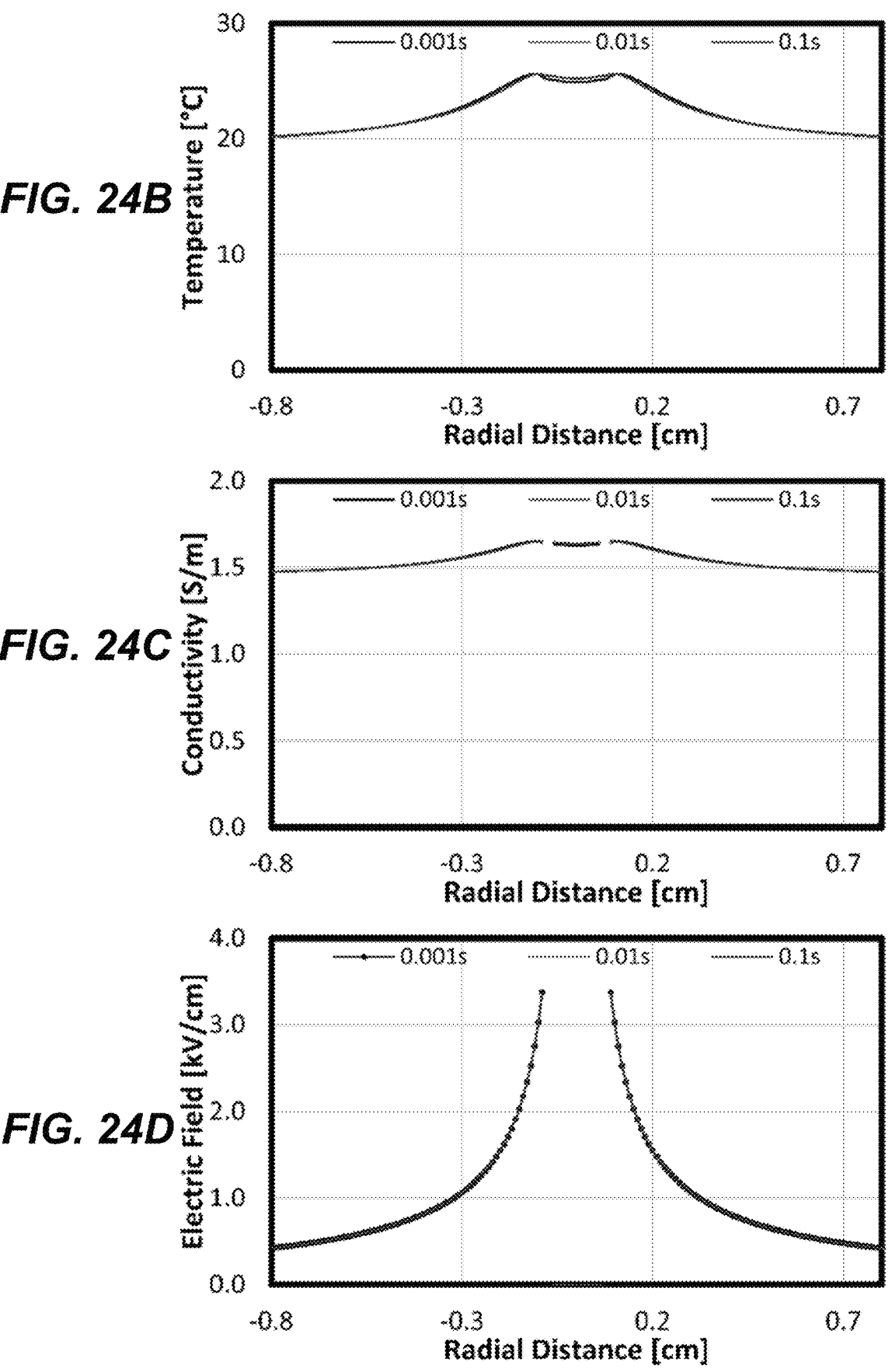

Separate finite element simulations were conducted for each experimental case using a temperature dependent electrical conductivity function to account for thermal effects on the electric field distribution. It was found that treatment voltage substantially impacted the electric field distribution within the simulated 3D tumor surrounding the coaxial ring and pin electrode. However, the baseline temperature (20° C. vs 37° C.) and the total dose delivered (0.001 s vs 0.01 s vs 0.1 s) did not change the electric field distribution found at times corresponding to the end of each parameter simulated. FIGS. 24A-24D are waveforms that illustrate simulated responses for IET doses of 0.001 s, 0.01 s, and 0.1 s, according to embodiments of the present invention. FIG. 24A is a waveform illustrating simulated temperature response during 750V 0.1 s IET treatment with a baseline temperatures of 20° C. and a set point of 25° C. Indicators represent the time required to reach an IET dose of 0.001 (t=19 s), 0.01 (t=224 s), and 0.1 s (t=2245 s). FIGS. 24B-24D are waveforms illustrating radial temperature (FIG. 24B), electrical conductivity (FIG. 24C), and electric field distributions (FIG. 24D) at times representing the end of simulated treatments with IET doses of 0.001 s (t=19 s), 0.01 s (t=224 s), and 0.1 s (t=2245 s). Note that there is significant overlap in the electric field distributions (FIG. 24D) between the simulations despite different treatment durations due to the implementation of temperature control. Independent of this finding, the simulated electric field distribution corresponding to respective experimental treatments was used in calculating lethal electric field thresholds.

Voltage Escalation: 500 ns 0.01 s IET Treatments

A voltage escalation study was conducted to determine optimal treatment parameters for evaluating treatment outcomes over a wide range of experimental pulse widths. For 500 ns 0.01 s treatments administered at 37° C. resulted in the smallest measurable ablations (1.87±1.46 mm). In this group, 2 of 6 (33%) resulted in non-existent ablations. Increasing the applied voltage to 750V, 1000V, and 1250V resulted in sequentially larger mean ablation diameters (e.g. FIG. 23A). However, the 1000V and 1250V treatments were not found to be statistically significantly different (p=0.4574). When these treatments (500 ns, 0.01 s) were replicated at 20° C. the 500V treatment group did not produce measurable ablation zones. However, the 750V, 1000V, and 1250V treatments resulted in sequentially larger (e.g. FIG. 23A) ablation diameters which were all significantly different (p<0.0001). For voltage-matched treatments all of the 37° C. ablations were found to be statistically significantly larger than the corresponding 20° C. treatment (p<0.0001). Of interest, no difference was found between the 37° C. 750V treatment and the 20° C. 1250V treatment (p=0.0138).

Statistically significant differences (p<0.02) were found between the lethal electric field thresholds (e.g. FIG. 23B) for all treatments except the 20° C. treatments administered at 1000V and 1250V (p=0.07) and the 37° C. treatments administered at 750V and 1000V (p=0.62). Both 500V treatment groups resulted in immeasurable ablation zones (20° C.: 100%, 37° C.: 33%). For these treatments the electric field value found at the electrode interface (2.24 kV/cm) was substituted to avoid skewing results towards lower predictions by omitting data.

Due to higher voltages inducing greater rates of Joule heating, the treatments sequentially required longer durations to complete despite the delivery of a constant 0.01 s dose (e.g. FIG. 23C). As a compromise between the minimum/maximum ablation sizes observable and the total treatment time all remaining treatments were administered with 750V pulse amplitudes.

Effect of Pulse Width: 750V 0.01 s IET Treatments

Figure 25A:
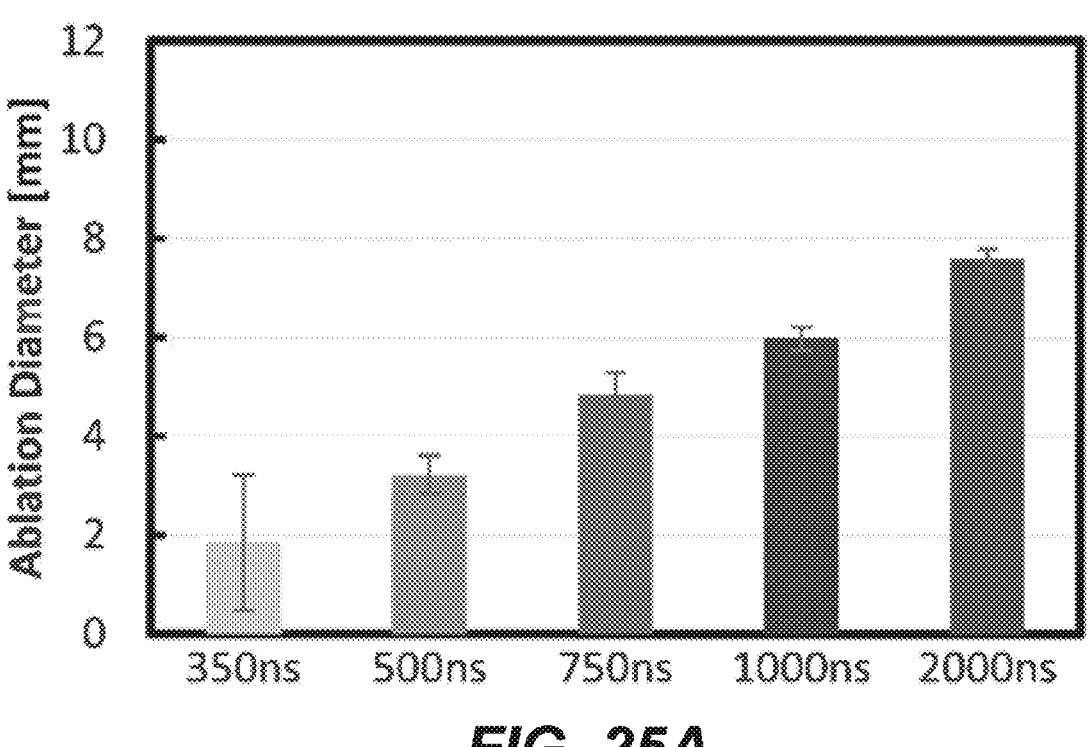
FIGS. 25A and 25B are graphs illustrating ablations according to embodiments of the present invention when 750V 0.01 s IET treatments were administered at 20° C. with pulse widths of 350 ns, 500 ns, 750 ns, 1000 ns, and 2000 ns.
Figure 25B:
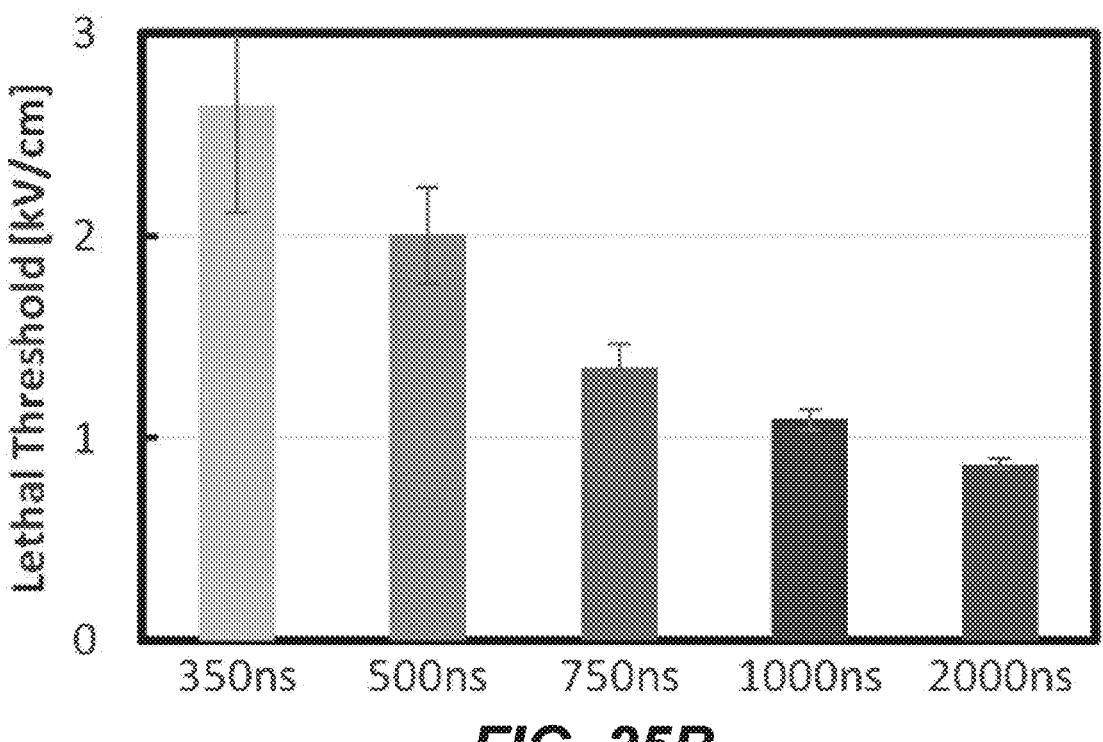

FIGS. 25A and 25B are graphs illustrating ablations according to embodiments of the present invention when 750V 0.01 s IET treatments were administered at 20° C. with pulse widths of 350 ns, 500 ns, 750 ns, 1000 ns, and 2000 ns. Mean ablation diameters (FIG. 24A) and lethal electric field thresholds (FIG. 24B) as a function of constitutive pulse widths. Ablation diameters and lethal thresholds were all found to be statistically significantly different between (p<0.0028). It was found that ablation diameter was a function of pulse width when 0.01 s IET treatments were administered with 750V pulses at 20° C. The smallest ablations were found for treatments with 350 ns pulses with sequentially larger ablation volumes found for treatments with 500 ns, 750 ns, 1000 ns, and 2000 ns pulses. These ablation volumes were found to be statistically significantly different (p<0.0001, FIG. 25A). Similarly, lethal electric field thresholds decreased from 2648±573 V/cm for 350 ns treatments to 827±27 V/cm for 2000 ns treatments.

Figure 26A:
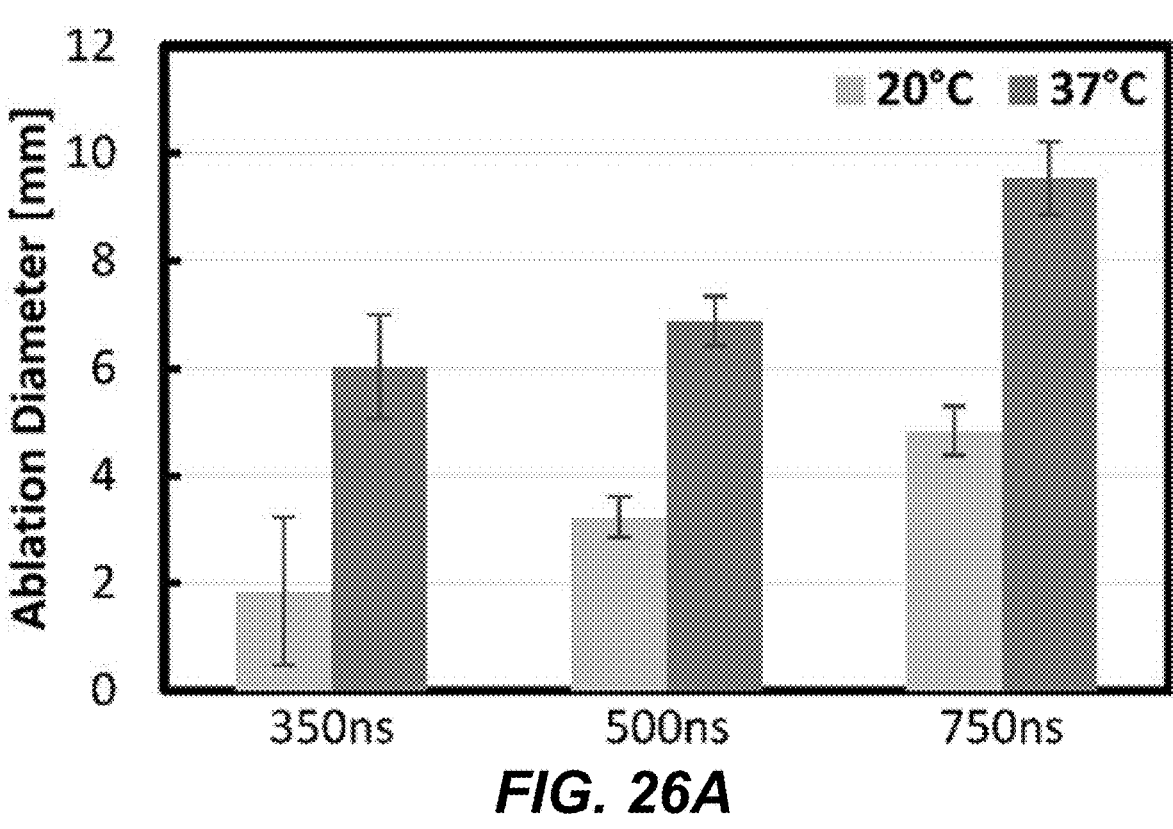
FIGS. 26A and 26B are graphs of ablation diameters and lethal electric field thresholds for 750V 0.01 s pulsed electric treatments according to embodiments of the present invention administered with 350, 500, or 750 ns pulses at starting temperatures of 20° C. or 37° C.
Figure 26B:
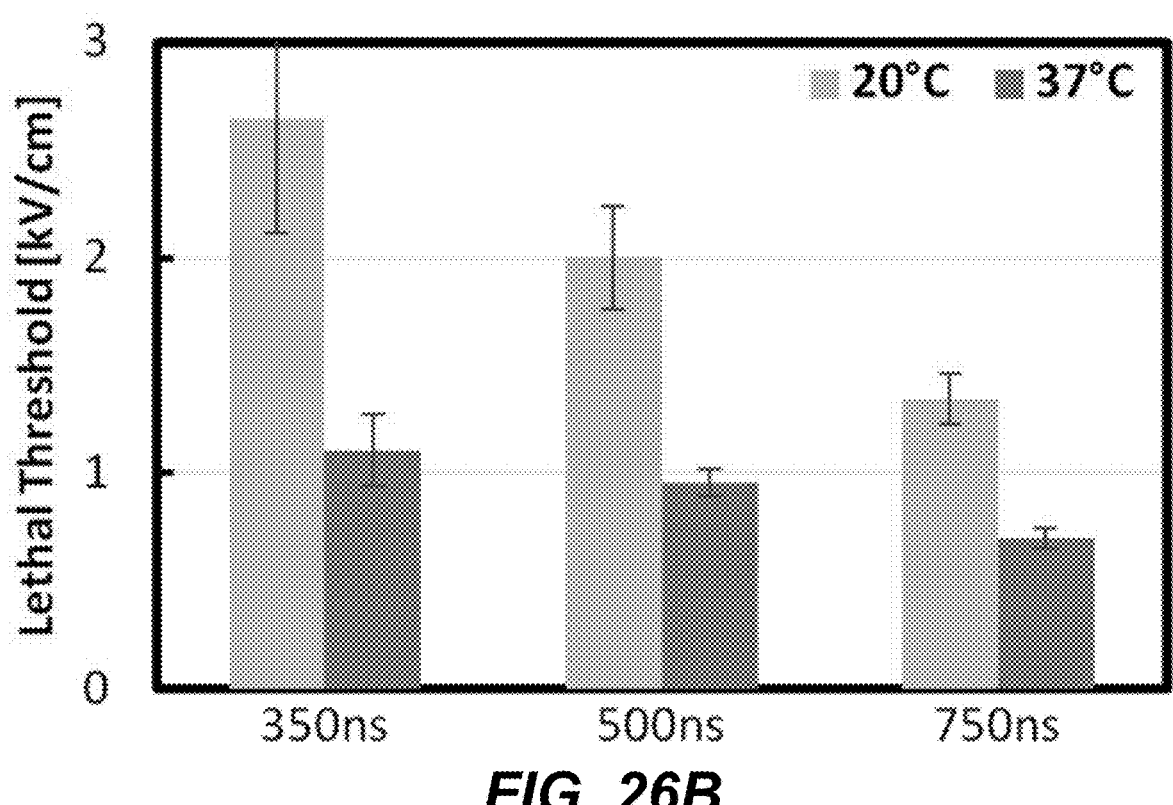

Temperature was found to impact the ablation volumes for treatments the submicrosecond duration pulses investigated with 37° C. treatments resulting in significantly (p<0.0001) larger ablations and significantly (p<0.0001) lower lethal electric field thresholds than 20° C. treatments. FIGS. 26A and 26B are graphs of ablation diameters (FIG. 26A) and lethal electric field thresholds (FIG. 26B) for 750V 0.01 s pulsed electric treatments according to embodiments of the present invention administered with 350, 500, or 750 ns pulses at starting temperatures of 20° C. or 37° C. When 0.01 s IET treatments were administered at 37° C. lethal thresholds of 1109±171, 954±63, 698±45 V/cm were found for 350, 500, and 750 ns pulse durations, respectively. In contrast, when treatments were administered at 20° C., lethal thresholds of 2648±537, 2002±239, 1347±114 V/cm were found for the same respective treatment parameters.

Effect of Integrated Time: 750V 500 and 2000 ns Treatment

Figure 27A:
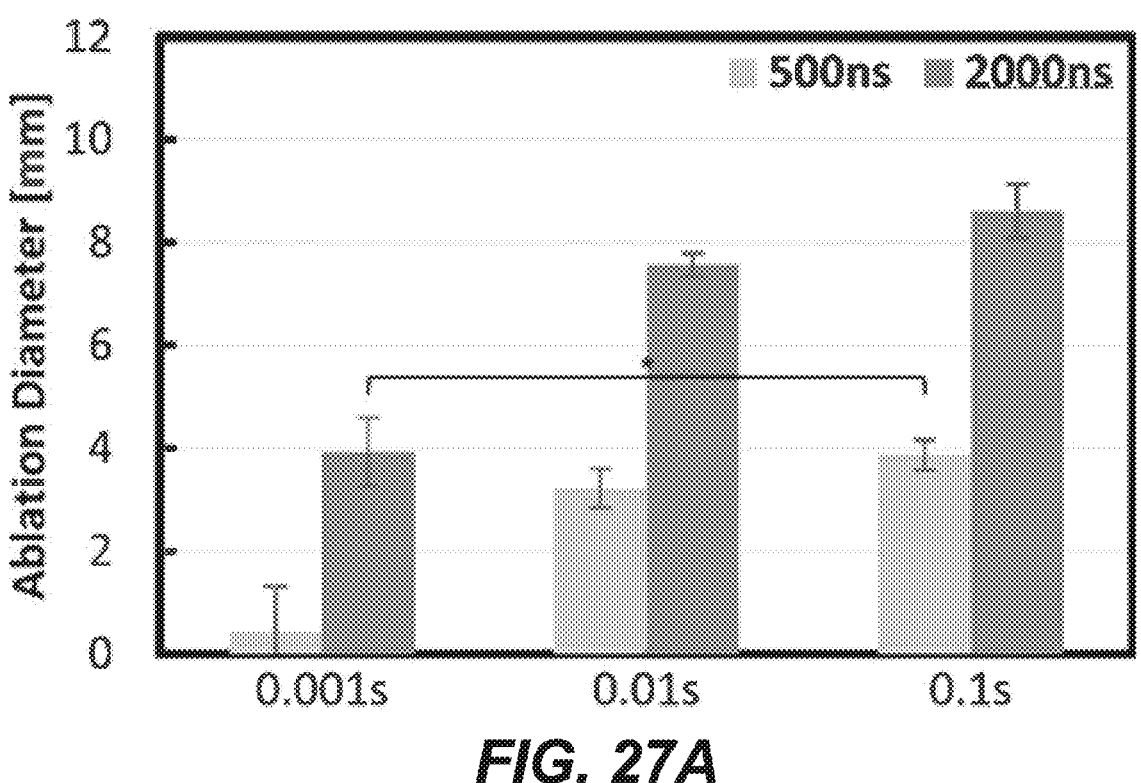
FIGS. 27A and 27B are graphs illustrating the effect of dose on ablation size, according to embodiments of the present invention.
Figure 27B:
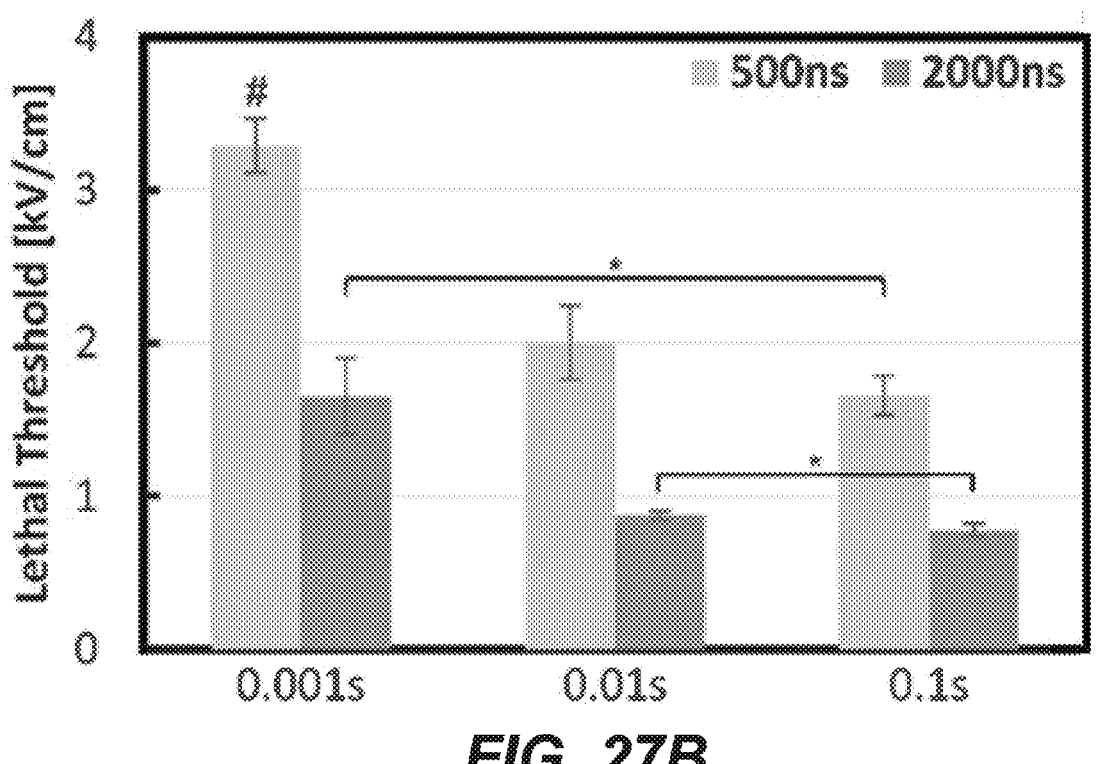

FIGS. 27A and 27B are graphs illustrating the effect of dose on ablation size, according to embodiments of the present invention. As illustrated in FIGS. 27A and 27B, ablation diameters (FIG. 27A) sequentially increased and lethal thresholds (FIG. 27B) sequentially decreased for 750V treatments according to embodiments of the present invention with pulse durations of 500 ns and 2000 ns when the dose (integrated energized time) was increased from 0.001 s to 0.1 s. Treatments were administered at 20° C. In FIGS. 27A and 27B, a '#' indicates treatments with non-measureable ablation diameters with electric field thresholds presumed to be 3.37 kV/cm, and a '*' indicates groups which were not statistically significantly different (p>0.14).

Increases in integrated time from 0.001 s to 0.1 s resulted in significant increases in ablation diameter for 750V treatments with 500 ns and 2000 ns pulses. For treatments with 500 ns pulses, doses of 0.001 s resulted in 80% of treatments (4 of 5 treatments) without a measurable ablation. For these treatments, the lethal threshold was assumed to be a minimum of 3.37 kV/cm representing the value at the electrode interface. Under these 500 ns treatments, the lethal threshold was found to be significantly (p<0.001) lower for each 10× increase in dose (e.g., FIG. 27B). A significant decrease in lethal threshold was found for 2000 ns pulses between 0.001 and 0.01 s (p<0.0001), but not between 0.01 and 0.1 s (p=0.1495). Interestingly, a statistically significant difference was not found between the 0.1 s IET 500 ns and 0.001 s IET 2000 ns ablation diameters (p=0.7589) or lethal thresholds (p=0.9648).

Clinical Treatment Parameters and Outcomes

As clinical administration of pulsed electrical treatments according to embodiments of the present invention will require the development of new instrumentation, it is of interest to determine appropriate treatment parameters and control schemes to enable these treatments. A finite element simulation of a single applicator and grounding pad (A+GP) configuration was utilized. As a baseline, typical NK-IRE treatments were simulated (3 kV, 100×100 μs pulses [0.01 s MT], 1 Hz [100 μs/s]) to determine the volume of tissue which would undergo irreversible electroporation (500V/cm), thermal cell death, protein coagulation, and blood flow stasis. Under these nominal conditions the NK-IRE treatment induced 1.58 cm³ IRE, 0.16 cm³ thermal death, 0.12 cm³ protein coagulation, and 0.12 cm³ blood flow stasis volumes.

Figures 28A, 28B, 28C, 28D:
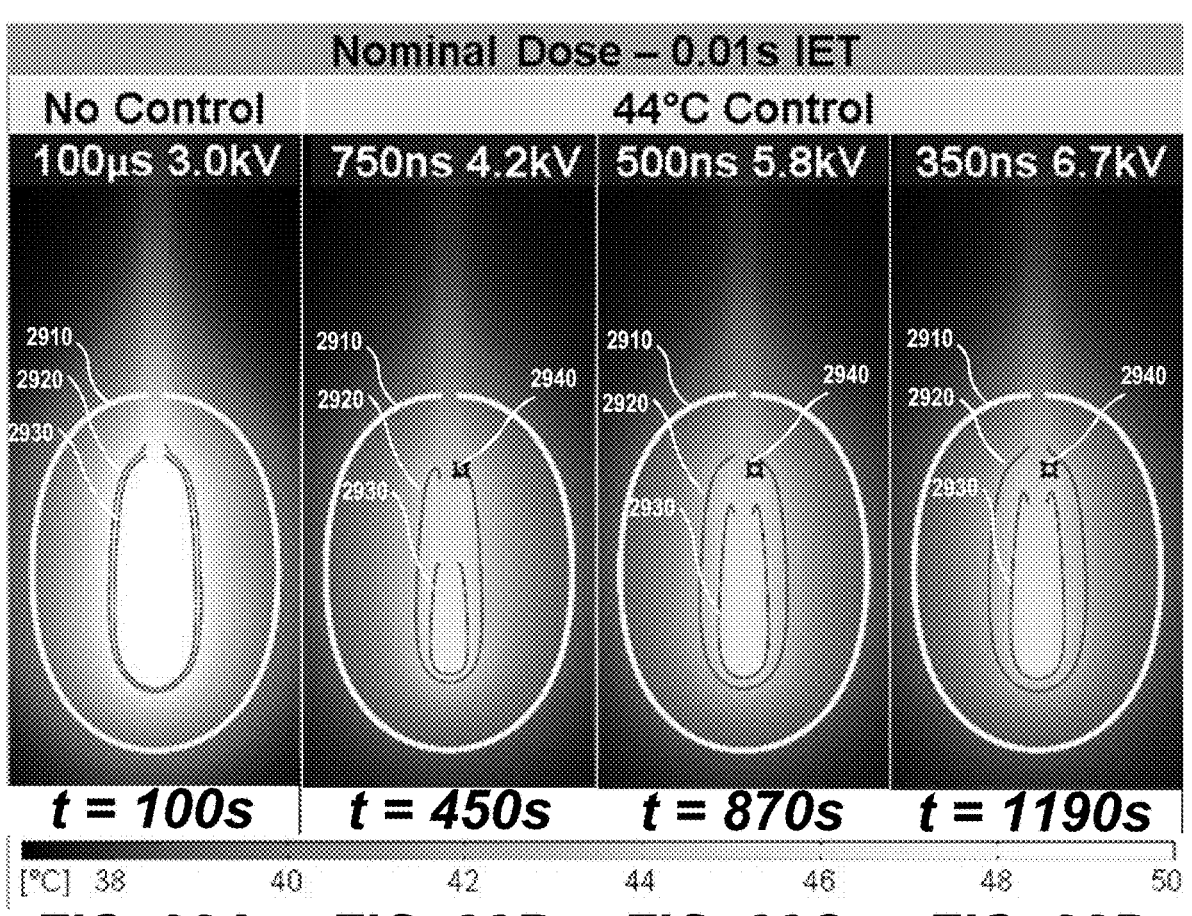
FIGS. 28A to 28E illustrate predicted ablation zones for simulated applicator and grounding pad (A+GP) treatments, according to embodiments of the present invention, as compared to conventional methods.
Figure 28E:
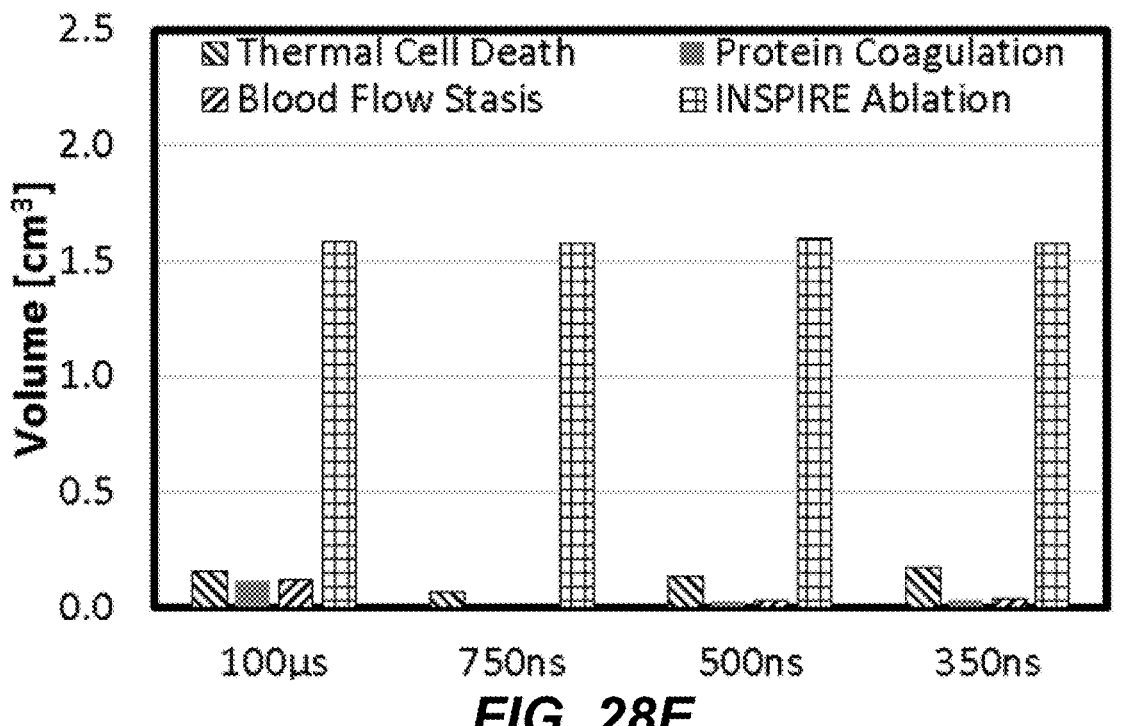

FIGS. 28A to 28E illustrate predicted ablation zones for simulated applicator and grounding pad (A+GP) treatments, according to embodiments of the present invention, as compared to conventional methods. FIG. 28A illustrates temperature distribution at the end (t=100 s) of a 3 kV 0.01 s NK-IRE treatment and the predicted ablation zone 2910 corresponding an electric field threshold of 500V/cm. FIGS. 28B to 28D illustrate temperature distributions, predicted ablation 2910, and thermal cell death 2920, protein coagulation 2930, and blood flow stasis zones at the end of 0.01 s pulsed electrical treatments, according to embodiments described herein, with 750 ns 4.2 kV pulses (t=450 s, 698V/cm), as illustrated in FIG. 28B, 500 ns 5.8 kV pulses (t=870 s, 953V/cm) as illustrated in FIG. 28C, and 50 ns 6.7 kV pulses (t=1190 s, 1110V/cm), as illustrated in FIG. 28D, when 44° C. temperature control was implemented. FIG. 28E illustrates predicted volumes associated with each form of cell death at the end of 0.01 s IET treatments for NK-IRE (100 us) without temperature control and pulsed electrical therapy (350, 500, 750 ns) treatments, according to embodiments of the present invention, with 44° C. temperature control. In FIGS. 28B to 28D, reference designator 2940 indicates the approximate location of the temperature acquisition for controlling energy delivery.

Figures 29A, 29B, 29C, 29D:
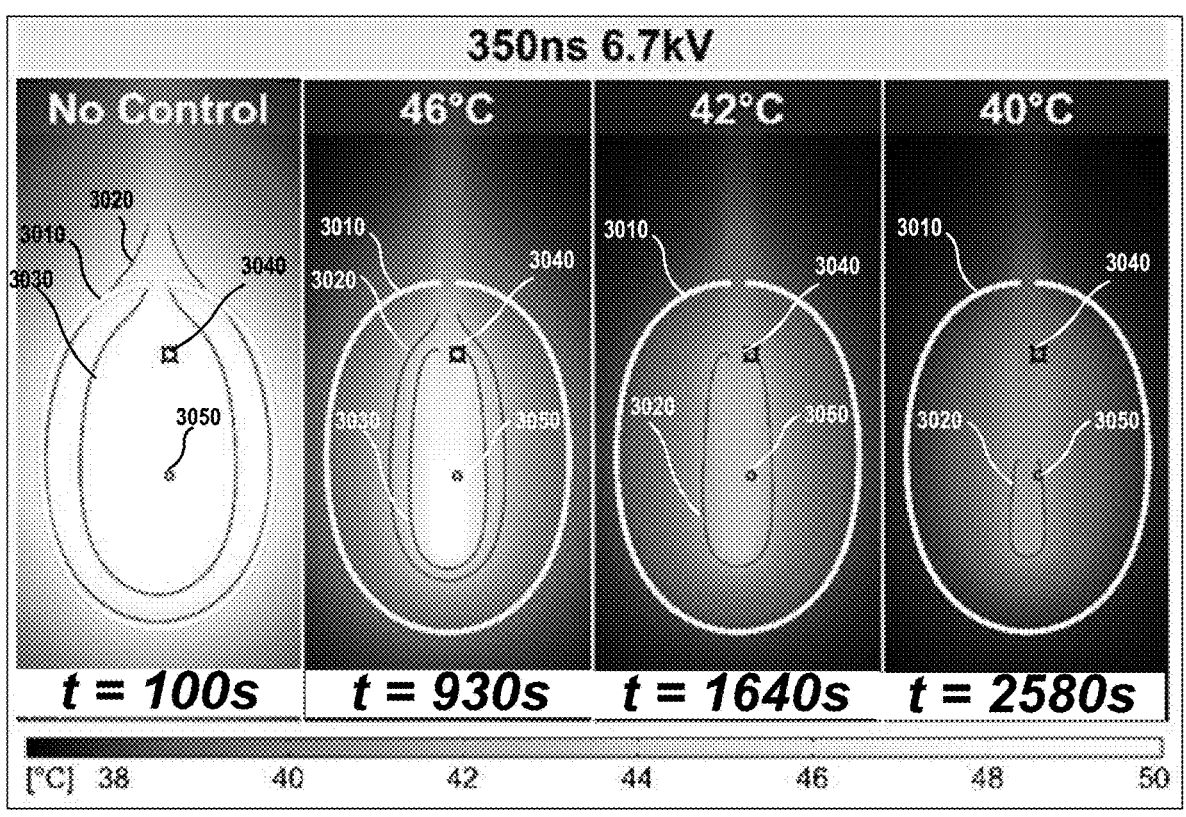
FIGS. 29A to 29F illustrate predicted ablation zones for simulated applicator and grounding pad (A+GP) treatments, according to embodiments of the present invention, as compared to conventional methods.
Figure 29E:
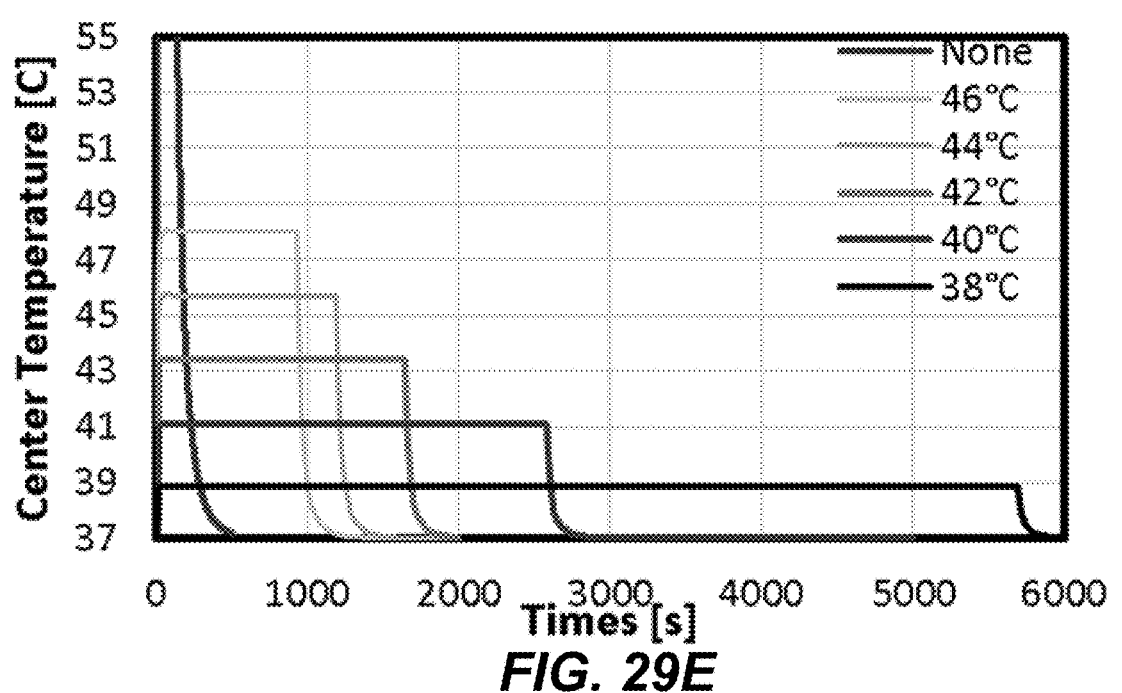
Figure 29F:
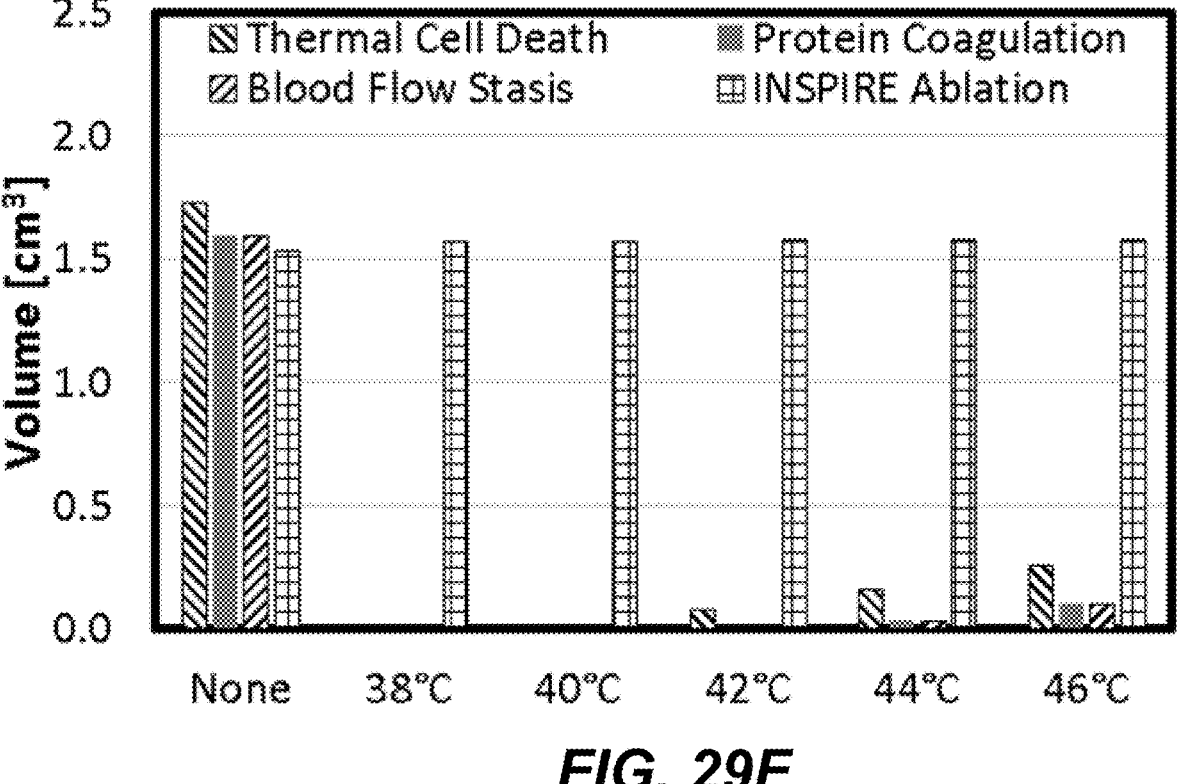

FIGS. 29A to 29E illustrate predicted ablation zones for simulated applicator and grounding pad (A+GP) treatments, according to embodiments of the present invention, as compared to conventional methods. To create an equivalent electric field induced cell death volume (1.58 cm³) with 0.01 s IET treatments according to embodiments of the present invention, the 350 ns (1109V/cm), 500 ns (953V/cm), and 750 ns (698V/cm) protocols utilized simulated voltages of 6.7 kV, 5.8 kV, and 4.2 kV. As NK-IRE treatments are currently administered without temperature feedback, this scenario was investigated for 350 ns electric therapy treatments according to embodiments of the present invention, with 6.7 kV pulses administered at a nominal rate of 100 μs/s (as illustrated in FIG. 29A) as well as with active temperature control utilizing a simulated temperature sensor at the electrode-insulator interface (as illustrated in FIGS. 29B-29D) similar to those presented experimentally. It was found that peak tissue temperatures above 100° C. (as illustrated in FIG. 29E) were induced without active temperature control yielding 1.54 cm³ electric field induced cell death, 1.73 cm³ thermal death, 1.59 cm³ protein coagulation, and 1.54 cm³ blood flow stasis volumes (as illustrated in FIG. 29F).

FIG. 29A illustrates temperature distribution at the end (t=100 s) of a 6.7 kV 0.01 s pulsed electric therapy when energy was delivered at a rate of 100 μs/s without temperature control. The predicted ablation zone 3010 corresponds to an electric field threshold of 1109V/cm. FIGS. 29B to 29D illustrate temperature distributions, predicted electric field induced cell death 3010, and thermal cell death 3020, protein coagulation 3030, and blood flow stasis zones at the end of 0.01 s 350 ns treatments according to embodiments of the present invention with temperature control set points of 46° C. (t=930 s) (as illustrated by FIG. 29B), 42° C. (t=1640 s) (as illustrated by FIG. 29C), 40° C. (t=2580 s) (as illustrated by FIG. 29D). FIG. 290E is a graph illustrating transient temperature profiles measured at the center of the exposed electrode (reference designator 3050 in FIGS. 29A to 29D) for each temperature control set point indicating that transient temperatures in this location were higher than the set point. FIG. 29F is a graph illustrating predicted volumes associated with each form of cell death at the end of 0.01 s IET 350 ns treatments without temperature control and with 38-46° C. temperature control set points. In FIGS. 29A to 29D, reference designator 3040 indicates the approximate location of the temperature acquisition for controlling energy delivery while reference designator 3030 indicates the location of temperature measurements at the center of the electrode.

A parametric analysis was conducted to determine the temperature set point necessary to induce an equivalent thermal cell death volume between nominal NK-IRE (0.16 cm$^3$) and 350 ns treatments according to embodiments of the present invention (e.g., INSPIRE) (FIGS. 29B-29F). It was found that this was achieved when the temperature at the insulator-electrode interface was maintained at 44° C. The temperature controlled treatments according to embodiments of the present invention utilized sequentially higher voltages to maintain the IRE ablation volume (1.6 cm$^3$) as pulse width was decreased and the simulated 750 ns (FIG. 28B), 500 ns (FIG. 28C), and 350 ns (FIG. 28D) treatments required 450 s, 870 s, and 1190 s to complete, respectively. These temperature controlled treatments according to embodiments of the present invention induced similar predicted thermal cell death volumes (0.07-0.17 cm$^3$) to NK-IRE, however, smaller volumes undergoing protein coagulation and blood flow stasis were predicted (FIG. 28E) for all temperature controlled treatments according to embodiments of the present invention.

Finally, it was of interest to determine if all temperature controlled treatments according to embodiments of the present invention with 0.001 s IET doses ($\frac{1}{10}^{th}$ NK-IRE) could produce ablation volumes equivalent to nominal NK-IRE treatments. It was found that, for this dose, 500 ns (2475 V/cm) and 2000 ns (1464 V/cm) treatments would require the application of pulses with amplitudes of 15200V and 8900V, respectively. Without temperature control enabled, these treatments required 10 s (100 µs/s) to complete with predicted thermal cell death volumes of 0.71 cm$^3$ and 0.27 cm$^3$, respectively. With temperature control enabled at 44° C. these treatments required 578 s and 203 s and induced thermal cell death volumes of 0.10 cm$^3$ and 0.02 cm$^3$, respectively.

NK-IRE is generally considered to be a non-thermal ablation modality in the context that the mechanism is not dependent on local tissue temperatures. This has been confirmed in vitro for temperatures between 2 and 37° C. for treatments employing 100 µs duration pulses, as described herein. However, a temperature dependence has been demonstrated for pulses between 1 and 8 microseconds and confirmed for pulses shorter than one microsecond, as described herein. Interestingly, the baseline temperature appears to play a large role. This indicates that pulse width, voltage, dose, and local tissue temperatures are important drivers in ablative outcomes for pulses in proximity of the cell membrane charging time. Though shorter pulses may utilize significantly greater electric fields to induce lethal effects, there is a continued interest in utilizing pulses with durations in the 250 to 2000 ns range to alleviate challenges (e.g. induction of muscle contractions) associated with 100 µs duration pulses used clinically in NK-IRE. There are, however, a cascading series of engineering challenges associated with the transition to (sub)microsecond duration electrical pulses. Of importance is that clinical pulse generation systems must be compatible with current clinical workflows necessitating the development of protocols which can be administered within a 30-60 minute window and achieve sufficient ablation volumes to warrant clinical use.

As NK-IRE is typically utilized for the treatment of 1-3 cm tumors, this translates to the use of voltages capable of achieving these volumes in a single applicator placement or sufficiently brief protocols, which enable the use of multiple sequential applicator placements.

Unlike NK-IRE, the ablation diameters induced by nanosecond duration pulses according to embodiments of the present invention continued to increase for doses between 0.001 and 0.1 s. There is therefore some complexity regarding optimal treatment strategies. This can be generalized as a choice between lower doses with higher voltages, moderate doses with moderate voltages, and higher doses and lower voltages. This is complicated by the potential for each of these strategies to induce thermal injury which is generally contraindicated for clinical cases selected for NK-IRE.

Energy delivery rates and electrical current are primary drivers of the Joule heating phenomena responsible for inducing thermal injury. When energy delivery rates were matched to NK-IRE (100 µs/s), simulated thermal damage volumes greater than the ablation volumes according to the present invention were calculated for 350 ns 0.01 s protocols (e.g., FIGS. 30A-30F). In these simulations the electrical current was temperature dependent and calculated between 18.5 and 21.3 A, which is similar to the initial currents targeted in clinical applications. Unfortunately, tissue conductivities and impedances are generally unknown a priori and dynamic current increases of 12-15 A are routinely reported clinically making it challenging to select a single energy delivery profile suitable for broad patient populations and applicator configurations. Trial and error selection of energy delivery rates, electrode exposures, and pulse widths is part of the standard operating procedure for NK-IRE, however, as nanosecond pulse duration protocols will necessitate the use of greater voltages, active feedback and dynamic energy delivery rates may be necessary to avoid the induction of unwanted thermal injury.

Active temperature control for pulsed electric field protocols has been demonstrated herein. This is important as even the lowest dose evaluated here (0.001 s) would utilize between 4.2 and 23.8 minutes (2000 and 350 ns pulses) if only a single waveform according to the present invention could be administered per cardiac cycle (~1 Hz). With cardiac synchronization in this scenario, the moderate (0.01 s) and high dose (0.1 s) 350 ns treatments according to the present invention would require 4 and 40 hours to complete. The use of active temperature feedback allows for an optimization minimizing both the induction of thermal injury and clinical treatment times. Utilizing a temperature set point of 44° C., the embodiments of the present invention described herein found moderate dose (0.01 s) treatments with 2000 ns to 350 ns pulses would require between 7.5 and 19.8 minutes (e.g., FIGS. 29A-29E), respectively. This computational analysis indicates that temperature controlled protocols according to embodiments of the present invention are clinically feasible assuming that 4.2-6.7 kV electrical pulses can be administered without inducing technical, clinical, or biological complications (e.g. tachycardia, muscle contractions, or arcing).

Figure 30:
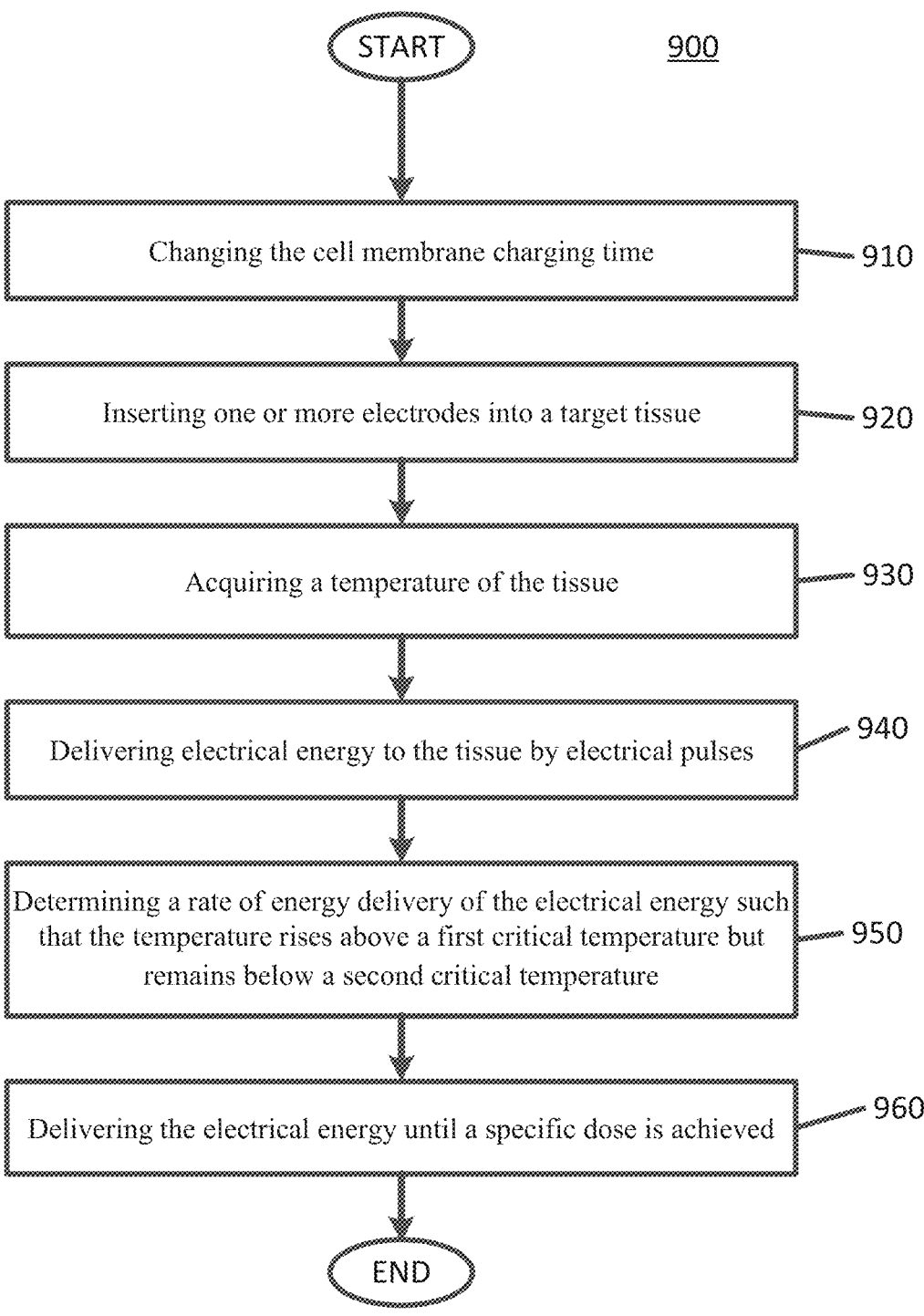
FIG. 30 illustrates operations for a method of treatment, according to embodiments of the present invention.

FIG. 30 illustrates operations 900 for a method of treatment, according to embodiments described herein. The operations 900 may begin at block 910 in which the cell membrane charging time is changed. Alternatively, the cell membrane charging time may be altered during subsequent operations (e.g. during block 940). The changing of the cell membrane charging time may be accomplished by one or more methods as described herein.

The operations 900 may continue with block 920 in which one or more electrodes are inserted into target tissue. The one or more electrodes may be similar, for example, to the electrodes discussed herein with respect to FIGS. 5A-5E, but the present invention is not limited thereto.

The operations 900 may continue with block 930 in which a temperature is acquired for the target tissue. The one or more temperature sensors may be similar, for example, to the temperature and/or thermal sensors discussed herein with respect to FIGS. 5A-5E, but the present invention is not limited thereto.

The operations 900 may continue with block 940 in which electrical energy is delivered to the target tissue by a plurality of electrical pulses. In some embodiments, the plurality of electrical pulses may be delivered by a particular waveform. The waveform selected may be, for example, one of the waveforms discussed with respect to FIGS. 6A, 6B and 7, though the embodiments described herein are not limited thereto.

The operations 900 may continue with block 950 in which a rate of energy delivery of the electrical energy is determined such that the temperature rises above a first critical temperature but remains below a second critical temperature. In some embodiments, the electrical pulses may be delivered from a high voltage power supply and/or capacitor bank. In some embodiments, a delay between ones of the plurality of electrical pulses is selected based on a temperature reading from the one or more temperature sensors. In some embodiments, the width of ones of the plurality of the electrical pulses is selected based on a measurement or observation. In some embodiments, the specific dose is changed based on a new delay between ones of the plurality of electrical pulses or based on a new width of ones of the plurality of electrical pulses or based on a new amplitude of ones of the plurality of electrical pulses.

The operations 900 may continue with block 960 in which the electrical energy is delivered until a specific dose is achieved.

The operations 900 may provide a method of electroporation and/or electrothermal therapy that is more effective than conventional treatments.

Though specific embodiments have been described herein, it will be understood by one of ordinary skill in the art that other embodiments are possible without deviating from the scope of the invention.

According to embodiments described herein, a method of modifying or killing cells by changing the cell membrane charging time to make cells more susceptible to the influence of electric fields.

In some embodiments, the cell membrane charging time is changed by modifying the electrical properties of the extracellular environment, intracellular environment, components of the intracellular environment, the cell membrane, or components of the cell membrane.

In some embodiments, the cell membrane charging time is changed by modifying the molecular or chemical properties of the extracellular environment, intracellular environment, components of the intracellular environment, the cell membrane, or components of the cell membrane.

In some embodiments, the cell membrane charging time is changed by modifying the temperature of the extracellular environment, intracellular environment, components of the intracellular environment, the cell membrane, or components of the cell membrane.

In some embodiments, the cell membrane charging time is changed by modifying the pH of the extracellular environment, intracellular environment, components of the intracellular environment, the cell membrane, or components of the cell membrane.

In some embodiments, components of the cell membrane includes hydrophilic head groups, hydrophobic tail groups, carbohydrates, cholesterols, receptors, protein channels, surface proteins, globular proteins, transmembrane proteins, integral proteins, lipid anchored proteins, peripheral proteins, voltage gated proteins, ion channels, proton pumps, guanine nucleotide-binding protein-coupled receptors, hydrophilic pores, hydrophobic pores, phospholipid molecules, the cytoskeleton, enzymes, hormones, focal adhesion groups, cell junctions, integrins, cadherins, cilia, filopoidia, microvilli, and/or the like.

In some embodiments, components of the extracellular environment include blood, blood plasma, extracellular fluid, cerebrospinal fluid, extracellular matrix, interstitial matrix, basement membrane, connective tissue, bone, tendon, ligament, proteins, collagen, elastin, fibronectin, laminin, enzymes, glycoproteins, fibrous proteins, polysaccharides, and/or the like.

In some embodiments, components of the intracellular environment include the cytoskeleton, organelles, the nucleus, the cytoplasm, proteins, DNA, and/or RNA.

In some embodiments, electric, magnetic, electromagnetic, thermal, radiation, ultrasound, and/or optical energy is used to modify the membrane charging time.

In some embodiments, chemicals or molecules are used to modify the cell membrane charging time including molecules for fatty acid supplementation (e.g., oleic acid, myristoleic acid, sapienic acid, vaccenic acid, linoleic acid, linolenic acid, alpha linolenic acid, linoelacidic acid, palmitic acid, palmitoleic acid, lauric acid, arachidonic acid, arachidic acid, stearic acid, myristic acid, elaidic acid, erucic acid, eicosapentaenoic acid, docosahexaenoic acid, hexanoic acid, acrylic acid, caprylic acid, capric acid, behenic acid, lignoceric acid, cerotic acid, cholesterol, cholesterol esterase, cholesterol transferase, cholesterol oxidase, cholesteryl ester transfer protein, sterol, beta-sitosterol, sigmasterol, lanosterol, coprostanol, or lecithin), cholesterol or fatty acid synthesis and transport affecters (e.g., decarestrictine D, U1866A, sulfosuccinimidyl oleate sodium, sulfosuccinimidyl myristate), phospholipids (e.g., phosphatitic acid, phosphatidylethanolamine, phosphatidylcholine, phosphatidylserine, phosphatidylinositol, phosphatidylinositol phosphate, phosphatidylinositol biphosphate, phosphatidylinositol trisphosphate, sphingomyelin, cardiolipin, filipin), cholesterol effecting drugs (e.g., probucol, gemfibrozil, fenofibrate, nicotinic acid, hyodeoxycholic acid, GW 590735, cyclandelate), cyclodextrins (e.g., beta cyclodextrin, beta cyclodextrin hydrate, hydroxypropyl beta cyclodextrin, methyl beta cyclodextrin, 2-hydroxypropyl beta cyclodextrin, heptakis(2,6-di-O-methyl) beta cyclodextrin, triacetyl beta cyclodextrin, succinyl-(2-hydroxypropyl) beta cyclodextrin, acetyl beta cyclodextrin, succinyl beta cyclodextrin, betadex), and/or other lipophilic or amphiphilic small molecules (e.g., curcumin, perllic acid, melatonin, ibuprofen, acetaminophen, acetylsalicylic acid) which affect the cell membrane charging time.

In some embodiments, changing the charging time of the cell membrane changes the electric field distribution in the extracellular environment, intracellular environment, and/or the cell membrane.

In some embodiments, changing the charging time of the cell membrane changes the response of the transmembrane potential due to an external stimulus (e.g., electric pulse, chemical gradient).

In some embodiments, the application of the electric field results in immediate or delayed cell death.

In some embodiments, the cell membrane charging time is changed by adding extrinsic molecules to the extracellular environment, cell membrane, and/or intracellular environment.

In some embodiments, modifying the cell includes making changes to its genome and/or the expression of certain genes.

In some embodiments, modifying the cells includes making it easier for drugs, genes, nucleic acids (e.g., nucleic acids encoding genes), and/or molecules to cross the cell membrane.

In some embodiments, modifying the cells includes making them a target of the immune system In some embodiments, modifying the cells includes stimulating a local and/or systemic immune response.

In some embodiments, modifying the cells includes altering the structure and/or function a cytoskeleton, a nucleus, a mitochondria, an endoplasmic reticulum, and/or other organelles.

In some embodiments, killing the cells includes rupturing the cell membrane and/or causing immediate cell death.

In some embodiments, killing the cells includes inducing apoptosis and/or delayed cell death.

In some embodiments, killing the cells includes making them a target for immune cells.

In some embodiments, the tissue under treatment is heated to modify the cell membrane charging time then pulsed electric fields are delivered to induce immediate or delayed cell death.

In some embodiments, control algorithms are used to maintain a temperature above a first critical threshold In some embodiments, control algorithms are used to maintain a temperature below a second critical temperature.

In some embodiments, one or more electrode is inserted into tissue. Temperature is acquired at specific locations. Pulsed electrical energy is delivered to this tissue. An algorithm is used to determine the rate of energy delivery such that the tissue temperature rises above a first critical temperature but remains below a second critical temperature. Electrical energy is delivered until a specific dose is achieved.

In some embodiments, energy is delivered between a single electrode and a grounding pad.

In some embodiments, energy is delivered between multiple electrodes and a grounding pad.

In some embodiments, energy is delivered between two or more electrodes sequentially or simultaneously.

In some embodiments, the electrodes are internally cooled.

In some embodiments, the electrodes are internally heated.

In some embodiments, the electrical pulses are between 1 ns and 1000 μs in duration, optionally between 100 ns and 10 μs.

In some embodiments, the electrical pulses are between 1V and 100,000V in amplitude, optionally between 250V and 10,000V.

In some embodiments, the electrical pulses are positive polarity or negative polarity.

In some embodiments, the electrical pulses alternate between positive and negative polarity.

In some embodiments, a positive polarity electrical pulse is delivered, followed by a first delay, then a negative polarity pulse is delivered followed by a second delay.

In some embodiments, the first delay is the same as the second delay and is between 10 ns and 100 ms in duration, optionally between 100 ns and 100 μs.

In some embodiments, the first delay is shorter than the second delay where the first delay is between 10 ns and 100 μs and the second delay is between 10 μs and 10 s.

In some embodiments, the first delay remains constant, but the second delay changes based on an algorithm.

In some embodiments, temperature is measured internally to an electrode.

In some embodiments, temperature is measured at one or more locations along the electrode surface.

In some embodiments, temperature is measured at a location within the tissue under treatment.

In some embodiments, temperature is measured at a critical location such as at a tumor margin or adjacent to important structures such as nerves, vasculature, vessels, or healthy tissue.

In some embodiments, temperatures at multiple locations are used to determine energy delivery rates.

In some embodiments, the first critical temperature is between 36° C. and 65° C., optionally between 37° C. and 55° C.

In some embodiments, the second critical temperature is between 37° C. and 120° C., optionally between 45° C. and 95° C.

In some embodiments, the energy delivery rate is controlled by adjusting the duty cycle.

In some embodiments, the energy delivery rate is controlled by adjusting the width of the electrical pulses.

In some embodiments, the energy delivery rate is controlled by adjusting the delay between electrical pulses between 0.1 Hz and 10,000 Hz, optionally between 1 Hz and 1000 Hz.

In some embodiments, the energy delivery rate is controlled by adjusting the amount of time that energy is delivered per second between 1 ns/s and 1 s/s, optionally between 1 μs/s and 500 μs/s.

In some embodiments, the specific dose is calculated as the total number of pulses delivered which is between 1 and 100,000,000 pulses, optionally between 100 and 100,000.

In some embodiments, the specific dose is calculated as the number of pulses times the duration of each pulse which is between 1 μs and 10 s, optionally between 0.001 s and 0.5 s.

In some embodiments, the specific dose changes when the pulse width, delays between pulses, pulse amplitudes, or target temperatures are changed.

In some embodiments, the pulse width, delays between pulses, pulse amplitudes or target temperatures are changed manually due to the observation of a clinical response.

In some embodiments, the pulse width, delays between pulses, pulse amplitudes, or target temperatures are changed automatically due to a measurement.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely in hardware, entirely in software (including firmware, resident software, micro-code, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible non-transitory medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks. As used herein, "a processor" may refer to one or more processors.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the FIGS. illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the FIGS. For example, two blocks shown in succession may, in fact, be executed substantially concurrently, or the blocks may sometimes be executed in the reverse order, depending upon the functionality involved. Although some of the diagrams include arrows on communication paths to show a primary direction of communication, it is to be understood that communication may occur in the opposite direction to the depicted arrows. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Other methods, systems, articles of manufacture, and/or computer program products will be or become apparent to one with skill in the art upon review of the embodiments described herein. It is intended that all such additional systems, methods, articles of manufacture, and/or computer program products be included within the scope of the present disclosure. Moreover, it is intended that all embodiments disclosed herein can be implemented separately or combined in any way and/or combination.

The terminology used herein is for the purpose of describing particular embodiments only and is not intended to be limiting to other embodiments. As used herein, the singular forms "a," "an," and "the" are intended to include the plural forms as well, unless the context clearly indicates otherwise. It will be further understood that the terms "comprises," "comprising," "includes," and/or "including," "have," and/ or "having" (and variants thereof) when used herein, specify the presence of stated features, integers, steps, operations, elements, and/or components, but do not preclude the presence or addition of one or more other features, integers, steps, operations, elements, components, and/or groups thereof. In contrast, the term "consisting of" (and variants thereof) when used in this specification, specifies the stated features, integers, steps, operations, elements, and/or components, and precludes additional features, integers, steps, operations, elements and/or components. Elements described as being "to" perform functions, acts and/or operations may be configured to or otherwise structured to do so. As used herein, the term "and/or" includes any and all combinations of one or more of the associated listed items and may be abbreviated as "/".

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the various embodiments described herein.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall support claims to any such combination or subcombination.

When a certain example embodiment may be implemented differently, a specific process order may be performed differently from the described order. For example, two consecutively described processes may be performed substantially at the same time or performed in an order opposite to the described order.

Like numbers refer to like elements throughout. Thus, the same or similar numbers may be described with reference to other drawings even if they are neither mentioned nor described in the corresponding drawing. Also, elements that are not denoted by reference numbers may be described with reference to other drawings.

In the drawings and specification, there have been disclosed typical embodiments and, although specific terms are employed, they are used in a generic and descriptive sense only and not for purposes of limitation, the scope of the disclosure being set forth in the following claims.

What is claimed is:

1. A method of treatment comprising modifying and/or killing a cell by changing a cell membrane charging time to make the cell more susceptible to an influence of an electric field, wherein changing the cell membrane charging time comprises:

inserting one or more electrodes into or adjacent to tissue surrounding the cell;

acquiring a temperature of the tissue;

delivering, via the one or more electrodes, electrical energy to the tissue by a plurality of electrical pulses; and increasing the temperature of the tissue using the electrical energy delivered to the tissue, to thereby change the cell membrane charging time, wherein increasing the temperature of the tissue comprises dynamically controlling a rate of energy delivery of the electrical energy such that the temperature of the tissue rises above a first critical temperature and remains below a second critical temperature.

2. The method of claim 1, wherein changing the cell membrane charging time further comprises changing a response of a transmembrane potential due to the electrical pulses.

3. The method of claim 1, wherein modifying the cell comprises modifying a genome and/or a gene expression of the cell.

4. The method of claim 1, wherein modifying the cell comprises making it easier for drugs, nucleic acids, and/or molecules to cross the cell membrane.

5. The method of claim 1, wherein modifying the cell comprises making the cell a target of an immune system of a host of the cell.

6. The method of claim 1, wherein dynamically controlling the rate of energy delivery of the electrical energy such that the temperature of the tissue rises above the first critical temperature and remains below the second critical temperature comprises adjusting at least one of a time delay between ones of the electrical pulses, a width of one or more of the electrical pulses, or an amplitude of one or more of the electrical pulses.

7. The method of claim 1, wherein the temperature of the tissue is increased by at least 5° C. using the electrical energy.

8. The method of claim 1, wherein the rate of energy delivery of the electrical energy is dynamically controlled to increase the temperature of the tissue above the first critical temperature and to maintain the temperature of the tissue at a value between the first and second critical temperatures until an end of delivery of the electrical energy.

9. The method of claim 1, wherein the first critical temperature is between 37° C. and 55° C., and wherein the second critical temperature is between 45° C. and 95° C.

10. The method of claim 1, wherein dynamically controlling the rate of energy delivery of the electrical energy such that the temperature of the tissue rises above the first critical temperature and remains below the second critical temperature comprises adjusting a duty cycle of the electrical pulses.

11. The method of claim 1, wherein dynamically controlling the rate of energy delivery of the electrical energy such that the temperature of the tissue rises above the first critical temperature and remains below the second critical temperature comprises adjusting a width of at least one of the electrical pulses.

12. The method of claim 1, wherein one or more of the electrical pulses are between 250 V and 10,000 V in amplitude.

13. The method of claim 1, wherein the electrical pulses comprise a positive polarity electrical pulse, followed by a first time delay, then a negative polarity pulse followed by a second time delay.

14. The method of claim 13, wherein the first time delay is equal to the second time delay and is between 100 ns and 100 µs in duration.

15. The method of claim 13, wherein the first time delay is shorter than the second time delay, and wherein the first time delay is between 10 ns and 100 µs in duration, and the second time delay is between 10 µs and 10 seconds in duration.

16. The method of claim 13, wherein the first time delay is predetermined, and wherein the second time delay is selected based on the temperature of the tissue.

17. The method of claim 1, further comprising delivering the electrical energy until a specific dose is achieved, wherein the specific dose is calculated as a total number of the electrical pulses delivered, and wherein the total number of the electrical pulses delivered is between 100 and 100,000 pulses.

18. The method of claim 1, wherein dynamically controlling the rate of energy delivery of the electrical energy such that the temperature of the tissue rises above the first critical temperature and remains below the second critical temperature comprises sequentially increasing widths of at least two consecutive electrical pulses among the plurality of electrical pulses.

19. An apparatus for preventing, mitigating, and/or reducing tissue damage during a pulsed electric field therapy comprising a plurality of electrical pulses, the apparatus comprising circuitry configured to modify and/or kill a cell by changing a cell membrane charging time to make the cell more susceptible to an influence of an electric field, wherein the apparatus comprises:

one or more electrodes configured to deliver electrical energy, via the electrical pulses, to tissue surrounding the cell; and one or more temperature sensors configured to acquire a temperature of the tissue, wherein the apparatus is configured to increase the temperature of the tissue using the electrical energy delivered to the tissue, to thereby change the cell membrane charging time, and wherein the apparatus is configured to dynamically control a rate of energy delivery of the electrical energy such that the temperature of the tissue rises above a first critical temperature and remains below a second critical temperature.

20. A method of treatment comprising modifying and/or killing a cell by changing a cell membrane charging time to make the cell more susceptible to an influence of an electric field, wherein changing the cell membrane charging time comprises:

inserting one or more electrodes into or adjacent to tissue surrounding the cell;

delivering, via the one or more electrodes, electrical energy to the tissue by a plurality of electrical pulses; and increasing a temperature of the tissue using the electrical energy delivered to the tissue, to thereby change the cell membrane charging time, wherein a width of at least one of the electrical pulses is less than or equal to the cell membrane charging time.

* * * * *